US008138177B2

(12) United States Patent
Ando et al.

(10) Patent No.: US 8,138,177 B2
(45) Date of Patent: Mar. 20, 2012

(54) BENZIMIDAZOLONE DERIVATIVES AS CB2 RECEPTOR LIGANDS

(75) Inventors: Kazuo Ando, Aichi-Ken (JP); Makoto Kawai, Aichi-ken (JP); Tsutomu Masuda, Aichi-ken (JP); Hirofumi Omura, Aichi-ken (JP)

(73) Assignee: Pfizer Inc., New York, NY (US)

( * ) Notice: Subject to any disclaimer, the term of this patent is extended or adjusted under 35 U.S.C. 154(b) by 471 days.

(21) Appl. No.: 11/909,763

(22) PCT Filed: Mar. 2, 2006

(86) PCT No.: PCT/IB2006/000521
§ 371 (c)(1),
(2), (4) Date: Mar. 23, 2009

(87) PCT Pub. No.: WO2006/097808
PCT Pub. Date: Sep. 21, 2006

(65) Prior Publication Data
US 2009/0181957 A1 Jul. 16, 2009

Related U.S. Application Data

(60) Provisional application No. 60/662,183, filed on Mar. 15, 2005.

(51) Int. Cl.
A61K 31/541 (2006.01)
A61K 31/5377 (2006.01)
A61K 31/454 (2006.01)
C07D 413/02 (2006.01)
C07D 211/32 (2006.01)
C07D 471/02 (2006.01)

(52) U.S. Cl. .................. 514/228.2; 514/234.5; 514/322; 514/395; 514/234.2; 514/232.2; 546/199; 546/118; 544/139; 544/127; 544/62; 544/82; 548/304.4

(58) Field of Classification Search ............... 514/228.2, 514/234.5, 322, 395, 303, 234.2, 232.5; 546/199, 546/118; 544/139, 127, 62, 82; 548/304.4
See application file for complete search history.

(56) References Cited

U.S. PATENT DOCUMENTS

| 5,280,028 | A | 1/1994 | Flynn et al. |
| 5,300,512 | A * | 4/1994 | Flynn et al. .................. 514/305 |
| 6,069,152 | A | 5/2000 | Schaus et al. |
| 6,117,882 | A | 9/2000 | Schaus et al. |
| 2004/0116465 | A1 | 6/2004 | Cheng et al. |
| 2009/0298811 | A1 * | 12/2009 | Ando et al. ................. 514/217.1 |

FOREIGN PATENT DOCUMENTS

| EP | 0523013 | | 1/1993 |
| WO | 9318027 | * | 9/1993 |
| WO | WO/1993/18027 | | 9/1993 |
| WO | WO/2005/021539 | | 3/2005 |
| WO | WO/2005/021547 | | 3/2005 |
| WO | WO/2005/123718 | | 12/2005 |

OTHER PUBLICATIONS

Turconi et al., Journal of Medicinal Chemistry (1990), 33(8), 2101-8.*
Dumuis et al., Naunyn-Schmiedeberg's Archives of Pharmacology (1991), 343(3), 245-51.*
Schaus et al., Journal of Medicinal Chemistry (1998), 41(11), 1943-1955.*
Sparatore et al., Farmaco (1999), 54(4), 248-254.*
J. Pharmacol. Exp. Ther. Feb. 2004;308(2):446-53.
Proc. Natl. Acad. Sci. USA, Sep. 2, 2003:100(18):10529-33.
Br. J. Pharmacol, Aug. 2004; 142(8):1247-54.
Tapia et al, J. Med. Chem. Am. Chem. Soc., vol. 42, No. 15, pp. 2870-2880 (1999).
Schaus et al, J. Med. chem. Am. Chem. Soc., vol. 41, No. 11, pp. 1943-1955 (1998).

* cited by examiner

*Primary Examiner* — Janet Andres
*Assistant Examiner* — Niloofar Rahmani
(74) *Attorney, Agent, or Firm* — James T. Wasicak; Lucy X. Yang

(57) ABSTRACT

This invention relates to compounds of the formula (I): or pharmaceutically acceptable salts thereof, wherein: A, B, $R^1$, $R^2$ and $R^3$ are each as described herein, and compositions containing such compounds and the use of such compounds in the treatment of a condition mediated by CB2 receptor binding activity such as, but not limited to, inflammatory pain, nociceptive pain, neuropathic pain, fibromyalgia, chronic low back pain, visceral pain, acute cerebral ischemia, pain, chronic pain, acute pain, post herpetic neuralgia, neuropathies, neuralgia, diabetic neuropathy, HIV-related neuropathy, nerve injury, rheumatoid arthritic pain, osteoarthritic pain, back pain, cancer pain, dental pain, fibromyalgia, neuritis, sciatica, inflammation, neurodegenerative disease, cough, broncho constriction, irritable bowel syndrome (IBS), inflammatory bowel disease (IBD), colitis, cerebrovascular ischemia, emesis such as cancer chemotherapy-induced emesis, rheumatoid arthritis, asthma, Crohn's disease, ulcerative colitis, asthma, dermatitis, seasonal allergic rhinitis, gastroesophageal reflux disease (GERD), constipation, diarrhea, functional gastrointestinal disorder, cutaneous T cell lymphoma, multiple sclerosis, osteoarthritis, psoriasis, systemic lupus erythematosus, diabetes, glaucoma, osteoporosis, glomerulonephritis, renal ischemia, nephritis, hepatitis, cerebral stroke, vasculitis, myocardial infarction, cerebral ischemia, reversible airway obstruction, adult respiratory disease syndrome, chronic obstructive pulmonary disease (COPD), cryptogenic fibrosing alveolitis or bronchitis.

(I)

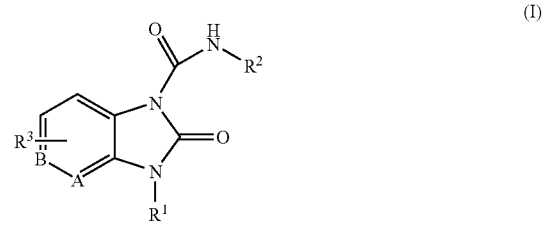

5 Claims, No Drawings

BENZIMIDAZOLONE DERIVATIVES AS CB2 RECEPTOR LIGANDS

BACKGROUND OF THE INVENTION

This invention relates to benzimidazolone derivatives. These compounds have selective cannabinoid(CB)2 receptor binding activity. The present invention also relates to a pharmaceutical composition, method of treatment and use, comprising the above derivatives for the treatment of disease conditions mediated by CB2 receptor binding activity.

In general, CB2 receptor ligands are found to be useful for the treatment of a variety of diseases, including inflammatory pain, nociceptive pain, neuropathic pain, fibromyalgia, chronic low back pain, visceral pain, rheumatoid arthritis, Crohn's disease, ulcerative colitis, asthma, dermatitis, seasonal allergic rhinitis, gastroesophageral reflux disease (GERD), constipation, diarrhea, functional gastrointestinal disorder, irritable bowel syndrome, cutaneous T cell lymphoma, multiple sclerosis, osteoarthritis, psoriasis, systemic lupus erythematosus, diabetes, glaucoma, osteoporosis, glomerulonephritis, renal ischemia, nephritis, hepatitis, cerebral stroke, vasculitis, myocardial infarction, cerebral ischemia, reversible airway obstruction, adult respiratory disease syndrome, chronic obstructive pulmonary disease (COPD), cryptogenic fibrosing alveolitis and bronchitis (see *J Pharmacol Exp Ther.* 2004 February; 308(2):446-53; *Proc Natl Acad Sci USA.* 2003 Sep. 2; 100(18):10529-33; *Br J. Pharmacol.* 2004 August; 142(8):1247-54). However, no compound having benzimidazolone backbone was known as CB2 ligands.

There is a need to provide new CB2 ligands that are good drug candidates. In particular, preferred compounds should bind potently to the CB2 receptor whilst showing little affinity for other receptors. They should be well absorbed from the gastrointestinal tract, be metabolically stable and possess favorable pharmacokinetic properties. When targeted against receptors in the central nervous system they should cross the blood brain barrier freely and when targeted selectively against receptors in the peripheral nervous system they should not cross the blood brain barrier. They should be non-toxic. Furthermore, the ideal drug candidate will exist in a physical form that is stable, non-hygroscopic and easily formulated.

SUMMARY OF THE INVENTION

In this invention, it has now been found out that the new class of benzimidazolone compounds show CB2 receptor binding activity and favorable properties as drug candidates, and thus are useful for the treatment of disease conditions mediated by CB2 binding activity such as inflammatory pain, nociceptive pain, neuropathic pain, fibromyalgia, chronic low back pain, visceral pain, acute cerebral ischemia, pain, chronic pain, acute pain, post herpetic neuralgia, neuropathies, neuralgia, diabetic neuropathy, HIV-related neuropathy, nerve injury, rheumatoid arthritic pain, osteoarthritic pain, back pain, cancer pain, dental pain, fibromyalgia, neuritis, sciatica, inflammation, neurodegenerative disease, cough, broncho constriction, irritable bowel syndrome (IBS), inflammatory bowel disease (IBD), colitis, cerebrovascular ischemia, emesis such as cancer chemotherapy-induced emesis, rheumatoid arthritis, Crohn's disease, ulcerative colitis, asthma, dermatitis, seasonal allergic rhinitis, GERD, constipation, diarrhea, functional gastrointestinal disorders, cutaneous T cell lymphoma, multiple sclerosis, osteoarthritis, psoriasis, systemic lupus erythematosus, diabetes, glaucoma, osteoporosis, glomerulonephritis, renal ischemia, nephritis, hepatitis, cerebral stroke, vasculitis, myocardial infarction, cerebral ischemia, reversible airway obstruction, adult respiratory disease syndrome, COPD, cryptogenic fibrosing alveolitis and bronchitis (hereinafter, referred as 'CB2 Diseases').

The present invention provides a compound of the following formula (I):

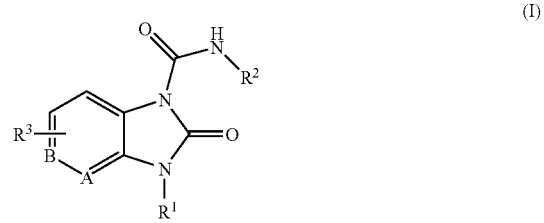

or a pharmaceutically acceptable salt thereof, wherein:
A is a carbon atom or a nitrogen atom;
B is a carbon atom or a nitrogen atom;
$R^1$ is a $C_1$-$C_4$ alkyl group substituted with 1 to 2 substituents independently selected from the group consisting of a $C_1$-$C_4$ alkyl group; a hydroxy group; a $C_1$-$C_4$ alkoxy group; a mercapt group; a $C_1$-$C_4$ alkylthio group; a $C_1$-$C_4$ alkylsulfinyl group; a $C_1$-$C_4$ alkylsulfonyl group; an amino group; a $C_1$-$C_4$ alkylamino group; a di($C_1$-$C_4$ alkyl)amino group; a ($C_1$-$C_4$ alkyl)($C_1$-$C_4$ alkylsulfonyl)amino group; a cycloalkyl group; a cycloalkyl group substituted with 1 to 3 substituents selected from the group consisting of a hydroxy group, a $C_1$-$C_4$ alkoxy group and a $C_1$-$C_4$ alkyl group; a heterocyclyl group; and a heterocyclyl group substituted with 1 to 3 substituents selected from the group consisting of a hydroxy group, a $C_1$-$C_4$ alkoxy group and a $C_1$-$C_4$ alkyl group;
$R^2$ is a cycloalkyl group; a cycloalkyl group substituted with 1 to 4 substituents selected from the group consisting of a hydroxy group, a $C_1$-$C_4$ hydroxyalkyl group, a $C_1$-$C_4$ alkoxy group, a $C_6$-$C_{10}$ aryloxy group, a mercapt group, a $C_1$-$C_4$ alkylthio group, a $C_6$-$C_{10}$ arylthio group, a carboxy group, a $C_1$-$C_4$ alkoxycarbonyl group, a $C_1$-$C_4$ alkyl group, a $C_2$-$C_4$ alkenyl group and a $C_2$-$C_4$ alkynyl group; a $C_6$-$C_{10}$ aryl group; a $C_6$-$C_{10}$ aryl group substituted with 1 to 3 substituents selected from the group consisting of a hydroxy group and a $C_1$-$C_4$ alkyl group; a heterocyclyl group; a heterocyclyl group substituted with 1 to 3 substituents selected from the group consisting of a hydroxy group and a $C_1$-$C_4$ alkyl group; a $C_1$-$C_{10}$ alkyl group; or a $C_1$-$C_{10}$ alkyl group substituted with 1 to 3 substituents independently selected from the group consisting of a cyano group, a hydroxy group, a trifluoromethyl group, a $C_2$-$C_4$ alkenyl group, a $C_2$-$C_4$ alkynyl group, a $C_1$-$C_4$ alkoxy group, a $C_6$-$C_{10}$ aryloxy group, a mercapt group, a $C_1$-$C_4$ alkylthio group, a $C_1$-$C_4$ alkylsulfinyl group, a $C_1$-$C_4$ alkylsulfonyl group, a $C_1$-$C_4$ alkylsulfonylamino group, a $C_6$-$C_{10}$ arylthio group, a carboxy group, a $C_1$-$C_4$alkyl-carbonyl group, a trifluoromethyl-carbonyl group, a $C_1$-$C_4$ alkoxy-carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl) amino-carbonyl group, a ($C_1$-$C_4$ hydroxyalkyl)($C_1$-$C_4$ alkyl)amino-carbonyl group, a heterocyclyl-carbonyl group, a cycloalkyl group, a heterocyclyl group, a $C_1$-$C_4$ alkyl-substituted heterocyclyl group and a $C_6$-$C_{10}$ aryl group; and $R^3$ is a hydrogen atom, a halogen atom, a hydroxy group, a $C_1$-$C_4$ alkyl group, $C_1$-$C_4$ haloalkyl group or a $C_1$-$C_4$ alkoxy group.

Also, the present invention provides the use of a compound of formula (I) or a pharmaceutically acceptable salt thereof, each as described herein, for the manufacture of a medicament for the treatment of a condition mediated by CB2 receptor binding activity.

Preferably, the present invention also provides the use of a compound of formula (I) or a pharmaceutically acceptable salt thereof, each as described herein, for the manufacture of a medicament for the treatment of diseases selected from CB2 Diseases.

Also, the present invention provides a pharmaceutical composition comprising a compound of formula (I) or a pharmaceutically acceptable salt thereof, each as described herein, together with a pharmaceutically acceptable carrier for said compound.

Also, the present invention provides a pharmaceutical composition comprising a compound of formula (I) or a pharmaceutically acceptable salt thereof, each as described herein, together with a pharmaceutically acceptable carrier for said compound and another pharmacologically active agent.

Further, the present invention provides a method of treatment of a condition mediated by CB2 receptor activity, in a mammalian subject, which comprises administering to a mammal in need of such treatment a therapeutically effective amount of a compound of formula (I) or a pharmaceutically acceptable salt thereof, each as described herein.

Examples of conditions mediated by CB2 receptor activity include, but are not limited to, CB2 Diseases.

The compounds of the present invention may show less toxicity, good absorption, distribution, good solubility, less protein binding affinity other than CB2 receptor, less drug-drug interaction, and good metabolic stability.

DETAILED DESCRIPTION OF THE INVENTION

In the compounds of the present invention:

Where $R^1$, $R^3$, one or more substituents of $R^1$ or one or more substituents of $R^2$ is the $C_1$-$C_4$ alkyl group, this $C_1$-$C_4$ alkyl group may be a straight or branched chain group, and examples include, but are not limited to, methyl, ethyl, propyl, isopropyl, butyl, isobutyl, sec-butyl and tert-butyl. Of these, methyl or ethyl is preferred; ethyl is more preferred for $R^1$; methyl is more preferred for $R^3$ and the substituents.

Where $R^2$ is the $C_1$-$C_{10}$ alkyl group, this $C_1$-$C_{10}$ alkyl group may be a straight or branched chain group, and examples include, but are not limited to, methyl, ethyl, propyl, isopropyl, butyl, isobutyl, sec-butyl, tert-butyl, pentyl, 2-methylbutyl, 1-ethylpropyl, 1,2-dimethylpropyl, 2,2-dimethylpropyl, hexyl, 2-methylpentyl, 1-propylpropyl, 1,2,2-trimethylpropyl, 1,3-dimethylbutyl, 1-ethyl-1-methylpropyl, heptyl, 2-methylhexyl, 1-propylbutyl, 1-isopropyl-2-methylpropyl, octyl, 2-methylheptyl, 1-butylbutyl, 1,1,3,3-tetramethylbutyl, nonyl, 2-methyloctyl, 1-butylpentyl, decyl, 2-methyldecyl and 1-pentylpentyl. Of these, $C_2$-$C_6$ alkyl is preferred; isobutyl, 1,2-dimethylpropyl, 2,2-dimethylpropyl and 1,2,2-trimethylpropyl are more preferred.

Where $R^3$, one or more substituents of $R^1$ or one or more substituents of $R^2$ is the $C_1$-$C_4$ alkoxy group, this $C_1$-$C_4$ alkoxy group represents the oxygen atom substituted with said $C_1$-$C_4$ alkyl group, and examples include, but are not limited to, a methoxy, ethoxy, propyloxy, isopropyloxy, butyloxy, isobutyloxy, sec-butyloxy and tert-butyloxy. Of these, methoxy is preferred.

Where one or more substituents of $R^1$ or one or more substituents of $R^2$ is the $C_1$-$C_4$ alkylthio group, this $C_1$-$C_4$ alkylthio group represents the sulfur atom substituted with said $C_1$-$C_4$ alkyl group, and examples include, but are not limited to, a methylthio, ethylthio, propylthio, isopropylthio, butylthio, isobutylthio, sec-butylthio and tert-butylthio. Of these, methylthio is preferred.

Where one or more substituents of $R^1$ or one or more substituents of $R^2$ is the $C_1$-$C_4$ alkylsulfinyl group, this $C_1$-$C_4$ alkylsulfinyl group represents the sulfinyl group substituted with said $C_1$-$C_4$ alkyl group, and examples include, but are not limited to, a methylsulfinyl, ethylsulfinyl, propylsulfinyl, isopropylsulfinyl, butylsulfinyl, isobutylsulfinyl, sec-butylsulfinyl and tert-butylsulfinyl. Of these, methylsulfinyl is preferred.

Where one or more substituents of $R^1$ or one or more substituents of $R^2$ is the $C_1$-$C_4$ alkylsulfonyl group, this $C_1$-$C_4$ alkylsulfonyl group represents the sulfonyl group substituted with said $C_1$-$C_4$ alkyl group, and examples include, but are not limited to, a methylsulfonyl, ethylsulfonyl, propylsulfonyl, isopropylsulfonyl, butylsulfonyl, isobutylsulfonyl, sec-butylsulfonyl and tert-butylsulfonyl. Of these, methylsulfonyl is preferred.

When one or more substituents of $R^2$ is the $C_1$-$C_4$ alkylsulfonylamino group, this $C_1$-$C_4$ alkylsulfonylamino group represents the amino group substituted with said $C_1$-$C_4$ alkylsulfonyl group, and examples include, but are not limited to, a methylsulfonylamino, ethylsulfonylamino, propylsulfonylamino, isopropylsulfonylamino, butylsulfonylamino, isobutylsulfonylamino, sec-butylsulfonylamino and tert-butylsulfonylamino. Of these, methylsulfonylamino is preferred.

Where one or more substituents of $R^1$ is the $C_1$-$C_4$ alkylamino group, this $C_1$-$C_4$ alkylamino group represents the amino group substituted with said $C_1$-$C_4$ alkyl group, and examples include, but are not limited to, methylamino, ethylamino, propylamino, isopropylamino, butylamino, isobutylamino, sec-butylamino and tert-butylamino. Of these, a $C_1$-$C_2$ alkylamino is preferred; methylamino is more preferred.

Where one or more substituents of $R^1$ is the di($C_1$-$C_4$ alkyl)amino group, this di($C_1$-$C_4$ alkyl)amino group represents the amino group disubstituted with said $C_1$-$C_4$ alkyl group, and examples include, but are not limited to, dimethylamino, N-methyl-N-ethylamino, diethylamino, dipropylamino, diisopropylamino, dibutylamino, diisobutylamino, and N,N-di(1-methylpropyl)amino. Of these, a di($C_1$-$C_3$alkyl)amino is preferred; dimethylamino and diethylamino are more preferred.

Where one or more substituents of $R^1$ is the ($C_1$-$C_4$ alkyl)($C_1$-$C_4$ alkylsulfonyl)amino group, this ($C_1$-$C_4$ alkyl)($C_1$-$C_4$ alkylsulfonyl)amino group represents the amino group substituted with said $C_1$-$C_4$ alkyl group and said $C_1$-$C_4$ alkylsulfonyl group, and examples include, but are not limited to, methyl(methylsulfonyl)amino, methyl(ethylsulfonyl)amino, ethyl(methylsulfonyl)amino and propyl(methylsulfonyl)amino. Of these, ($C_1$-$C_2$ alkylsulfonyl)($C_1$-$C_2$ alkyl)alkylamino is preferred; methyl(methylsulfonyl)amino is more preferred.

Where one or more substituents of $R^2$ is the $C_1$-$C_4$ hydroxyalkyl group, this $C_1$-$C_4$ hydroxyalkyl group represents said $C_1$-$C_4$ alkyl group substituted with hydroxy, and examples include, but are not limited to, hydroxymethyl, hydroxyethyl, hydroxypropyl, hydroxyisopropyl, and hydroxybutyl. Of these, a $C_1$-$C_2$ hydroxyalkyl is preferred; hydroxymethyl is more preferred.

Where one or more substituents of $R^2$ is the $C_1$-$C_4$ alkyl-carbonyl group, this $C_1$-$C_4$ alkyl-carbonyl group represents the carbonyl group substituted with said $C_1$-$C_4$ alkyl group, and examples include, but are not limited to, acetyl, ethylcarbonyl, propylcarbonyl, isopropylcarbonyl, butylcarbonyl, isobutylcarbonyl, sec-butylcarbonyl and tert-butylcarbonyl. Of these, acetyl is preferred.

Where one or more substituents of $R^2$ is the $C_1$-$C_4$ alkoxy-carbonyl group, this $C_1$-$C_4$ alkoxy-carbonyl group represents the carbonyl group substituted with said $C_1$-$C_4$ alkoxy group, and examples include, but are not limited to, a methoxycarbonyl, ethoxycarbonyl, propyloxycarbonyl, isopropyloxycarbonyl, butyloxycarbonyl, isobutyloxycarbonyl, sec-butyloxycarbonyl and tert-butyloxycarbonyl. Of these, methoxycarbonyl is preferred.

Where one or more substituents of $R^2$ is the $C_1$-$C_4$ hydroxyalkylamino-carbonyl group, this $C_1$-$C_4$ hydroxyalkylamino-carbonyl group represents the aminocarbonyl group substituted with said $C_1$-$C_4$ hydroxyalkyl group, and examples include, but are not limited to, a hydroxymethylaminocarbonyl, 2-hydroxyethylaminocarbonyl, 3-hydroxypropylaminocarbonyl, 4-hydroxybutylaminocarbonyl and 3-hydroxyisobutylaminocarbonyl. Of these, a $C_1$-$C_2$ hydroxyalkylaminocarbonyl is preferred; 2-hydroxyethylaminocarbonyl is more preferred.

Where one or more substituents of $R^2$ is the $C_1$-$C_4$ alkylamino-carbonyl group, this $C_1$-$C_4$ alkylamino-carbonyl group represents the aminocarbonyl group substituted with said $C_1$-$C_4$ alkyl group, and examples include, but are not limited to, methylaminocarbonyl, ethylaminocarbonyl, propylaminocarbonyl, isopropylaminocarbonyl, butylaminocarbonyl, isobutylaminocarbonyl, sec-butylaminocarbonyl and tert-butylaminocarbonyl. Of these, a $C_1$-$C_2$ alkylaminocarbonyl is preferred; methylamino carbonyl is more preferred.

Where one or more substituents of $R^2$ is the di($C_1$-$C_4$ alkyl) amino-carbonyl group, this di($C_1$-$C_4$ alkyl)amino-carbonyl group represents the carbonyl group substituted with said di($C_1$-$C_4$ alkyl)amino group, and examples include, but are not limited to, a dimethylaminocarbonyl, N-methyl-N-ethylaminocarbonyl, diethylaminocarbonyl, dipropylaminocarbonyl, diisopropylaminocarbonyl, dibutylaminocarbonyl, diisobutylaminocarbonyl, and N,N-di(1-methylpropyl) aminocarbonyl. Of these, a di($C_1$-$C_3$alkyl)amino-carbonyl is preferred; dimethylaminocarbonyl and diethylaminocarbonyl are more preferred.

Where one or more substituents of $R^2$ is the ($C_1$-$C_4$ hydroxyalkyl) ($C_1$-$C_4$ alkyl)amino-carbonyl group, this ($C_1$-$C_4$ hydroxyalkyl) ($C_1$-$C_4$ alkyl)amino-carbonyl group represents the aminocarbonyl group substituted with said $C_1$-$C_4$ hydroxyalkyl group and said $C_1$-$C_4$ alkyl group, and examples include, but are not limited to, a N-hydroxymethyl-N-methylaminocarbonyl, N-methyl-N-(2-hydroxyethyl)aminocarbonyl, N-methyl-N-(3-hydroxypropyl)aminocarbonyl, N-methyl-N-(2-methyl-2-hydroxyethyl)aminocarbonyl, and N-methyl-N-(4-hydroxybutyl)aminocarbonyl. Of these, N-hydroxymethyl-N-methylaminocarbonyl and N-methyl-N-(2-hydroxyethyl)aminocarbonyl are preferred.

Where $R^2$ or one or more substituents of $R^2$ is the $C_6$-$C_{10}$ aryl group, this $C_6$-$C_{10}$ aryl group may be phenyl, 1-naphtyl or 2-naphtyl. Of these, 1-naphtyl is preferred.

Where one or more substituents of $R^2$ is the $C_2$-$C_4$ alkenyl group, this $C_2$-$C_4$ alkenyl group may be a straight or branched chain group, and examples include, but are not limited to, a vinyl, 1-propenyl, 2-propenyl, 1-methyl-1-propenyl, and 3-butenyl. Of these, $C_2$-$C_3$ alkenyl is preferred; vinyl is more preferred.

Where one or more substituents of $R^2$ is the $C_2$-$C_4$ alkynyl group, this $C_2$-$C_4$ alkynyl group may be a straight or branched chain group, and examples include, but are not limited to, ethynyl, 1-propynyl, 2-propynyl, 1-butynyl, and 3-butynyl. Of these, $C_2$-$C_3$ alkynyl is preferred; ethynyl is more preferred.

Where one or more substituents of $R^2$ is the $C_6$-$C_{10}$ aryloxy group, this represents the oxygen atom substituted with the said $C_6$-$C_{10}$ aryl group, and examples include, but are not limited to, phenoxy, 1-naphtyloxy or 2-naphtyloxy. Of these, phenoxy is preferred.

Where one or more substituents of $R^2$ is the $C_6$-$C_{10}$ arylthio group, this represents the sulfur atom substituted with said $C_6$-$C_{10}$ aryl group, and examples include, but are not limited to, phenylthio, 1-naphtylthio or 2-naphtylthio. Of these, phenylthio is preferred.

Where $R^2$, one or more substituents of $R^1$ or one or more substituents of $R^2$ is the cycloalkyl group, this may be a cycloalkyl group having three to 8 carbon atoms, and examples include, but are not limited to, a cyclopropyl, cyclobutyl, cyclopenthyl, cyclohexyl, cycloheptyl and cyclooctyl. These groups may be fused with the said aryl group or the alkyl group to form the bicyclic or tricyclic ring, and examples include, but are not limited to, 1,2,3,4-tetrahydronaphthalenyl, 2,3-dihydro-1H-indenyl, adamantly, 2,6,6-trimethylbicyclo[3.1.1]hept-3-yl], 6,6-dimethylbicyclo[3.1.1]hept-2-yl and bicyclo[2.2.1] hept-2-yl. Of these, $C_3$-$C_5$ cycloalkyl is preferred; cyclopropyl is more preferred.

Where $R^3$ is the halogen atom, they may be a fluorine, chlorine, bromine or iodine atom. Of these, a fluorine atom is preferred.

Where $R^2$, one or more substituents of $R^1$ or one or more substituents of $R^2$ is the heterocyclyl group, this may be a 3, 4, 5, or 6-membered ring containing at least one hetero atom selected from N, O and S, and examples include, but not limited to, oxiranyl, 1-pyrrolidinyl, 2-pyrrolidinyl, 1-imidazolidinyl, 2-tetrahydrofuranyl, 1-piperidinyl, 2-piperidinyl, 1-piperazinyl, 4-tetrahydropyranyl, 4-morpholinyl, 4-thiomorpholinyl, 2-thienyl, 2-furyl, 2-thiazolyl, 2-oxazolyl, 5-tetrazolyl, 2-pyridyl, 3-pyridyl, 4-pyridyl, 2-pyrazyl, 2-pyrimidinyl, 1,2,4-oxadiazol-5-yl and 1,3,4-oxadiazol-2-yl. These groups may be fused with the said aryl group or each other to form the bicyclic ring, and examples include, but are not limited to, quinolinyl, isoquinolinyl, chromanyl and isochromanyl. Of these, bicyclic heterocyclyl group is preferred for $R^2$; monocyclic saturated heterocyclyl group is preferred for the substituent of $R^1$; N-containing 3 to 5 membered heterocyclyl group is preferred for the substituent of $R^2$; chromanyl is more preferred for $R^2$; 4-morpholinyl and 4-thiomorpholinyl are more preferred for the substituent of $R^1$; 5-tetrazolyl is more preferred for the substituent of $R^2$.

Where one or more substituents of $R^2$ is the heterocyclyl-carbonyl group, this represents the carbonyl group substituted with said heterocyclyl group, and examples include, but not limited to, 1-pyrrolidinylcarbonyl, 1-piperidinylcarbonyl, 4-tetrahydropyranylcarbonyl, 4-morpholinylcarbonyl and 4-thiomorpholinylcarbonyl. Of these, N-containing 5 to 6 membered heterocyclyl-carbonyl is preferred; 1-pyrrolidinylcarbonyl and 4-morpholinylcarbonyl are more preferred.

Where one or more substituents of $R^2$ is the $C_1$-$C_4$ alkyl-substituted heterocyclyl group, this represents the heterocyclyl group substituted with said $C_1$-$C_4$ alkyl group, and examples include, but not limited to, 2-methyl-1-pyrrolidinyl, 1-methyl-2-pyrrolidinyl, 1-methyl-2-tetrahydrofuranyl, 2-methyl-1-piperidinyl, 1-methyl-2-piperidinyl, 2-methyl-1-piperazinyl, 2-methyl-4-tetrahydropyranyl, 2-methyl-4-morpholinyl, 2-methyl-4-thiomorpholinyl, 2-methyl-4-pyridyl, 1-methyl-5-tetrazolyl, 2-methyl-5-tetrazolyl and 2-methylchromanyl. Of these, $C_1$-$C_2$ alkyl-substituted heterocyclyl group; 1-methyl-5-tetrazolyl and 2-methyl-5-tetrazolyl are more preferred.

Where $R^3$ is the $C_1$-$C_4$ haloalkyl group, this represents said $C_1$-$C_4$ alkyl group substituted with 1 to 8 halogen atom(s), and examples include, but not limited to, trifluoromethyl, difluoromethyl, pentafluoroethyl, 2,2,2-trifluoroethyl, 2-chloromethyl, 1,1-difluoroethyl, 3,3,3-trifluoropropyl and 4,4,-trifluorobutyl. Of these, $C_1$-$C_2$ fluoroalkyl is preferred; trifluoromethyl and 2,2,2-trifluoroethyl are more preferred.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

Preferred compounds of the present invention are those compounds of formula (I) or a pharmaceutically acceptable salt thereof, each as described herein, in which:

(A) A is a carbon atom or a nitrogen atom; B is a carbon atom or a nitrogen atom; $R^1$ is a $C_1$-$C_4$ alkyl group substituted with 1 to 3 substituents independently selected from the group consisting of a $C_1$-$C_4$ alkyl group; a hydroxy group; a $C_1$-$C_4$ alkoxy group; an amino group; a $C_1$-$C_4$ alkylamino group; a di($C_1$-$C_4$ alkyl)amino group; a ($C_1$-$C_4$ alkyl)($C_1$-$C_4$ alkylsulfonyl)amino group; a cycloalkyl group; a cycloalkyl group substituted with 1 to 3 substituents selected from the group consisting of a hydroxy group, a $C_1$-$C_4$ alkoxy group and a $C_1$-$C_4$ alkyl group; a heterocyclyl group; and a heterocyclyl group substituted with 1 to 3 substituents selected from the group consisting of a hydroxy group, a $C_1$-$C_4$ alkoxy group and a $C_1$-$C_4$ alkyl group; $R^2$ is a cycloalkyl group substituted with 1 to 3 substituents selected from the group consisting of a hydroxy group, a $C_1$-$C_4$ hydroxyalkyl group, a carboxy group and a $C_1$-$C_4$ alkoxy-carbonyl group; a heterocyclyl group; a heterocyclyl group substituted with 1 to 3 substituents selected from the group consisting of a hydroxy group and a $C_1$-$C_4$ alkyl group; or a $C_1$-$C_{10}$ alkyl group substituted with 1 to 3 substituents independently selected from the group consisting of a cyano group, a hydroxy group, a trifluoromethyl group; a $C_2$-$C_4$ alkenyl group, a $C_2$-$C_4$ alkynyl group, a $C_1$-$C_4$ alkoxy group, a $C_6$-$C_{10}$ aryloxy group, a mercapt group, a $C_1$-$C_4$ alkylthio group, a $C_1$-$C_4$ alkylsulfinyl group, a $C_1$-$C_4$ alkylsulfonyl group, a $C_1$-$C_4$ alkylsulfonylamino group, a $C_6$-$C_{10}$ arylthio group, a carboxy group, a $C_1$-$C_4$ alkyl-carbonyl group, a trifluoromethyl-carbonyl group, a $C_1$-$C_4$ alkoxy-carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl)amino-carbonyl group, a ($C_1$-$C_4$ hydroxyalkyl)($C_1$-$C_4$ alkyl)amino-carbonyl group, a heterocyclyl-carbonyl group, a cycloalkyl group, a heterocyclyl group, a $C_1$-$C_4$ alkyl-substituted heterocyclyl group and a $C_6$-$C_{10}$ aryl group; and $R^3$ is a hydrogen atom, a halogen atom, a $C_1$-$C_4$ alkyl group or a $C_1$-$C_4$ alkoxy group;

(B) A is a carbon atom or a nitrogen atom; B is a carbon atom or a nitrogen atom; $R^1$ is a $C_1$-$C_2$ alkyl group substituted with 1 to 3 substituents independently selected from the group consisting of a $C_1$-$C_4$ alkyl group; a hydroxy group; a $C_1$-$C_2$ alkoxy group; an amino group; a $C_1$-$C_4$ alkylamino group; a di($C_1$-$C_4$ alkyl)amino group; a ($C_1$-$C_4$ alkyl)($C_1$-$C_4$ alkylsulfonyl)amino group; a cycloalkyl group; a cycloalkyl group substituted with 1 to 3 substituents selected from the group consisting of a hydroxy group, a $C_1$-$C_4$ alkoxy group and a $C_1$-$C_4$ alkyl group; a heterocyclyl group; and a heterocyclyl group substituted with 1 to 3 substituents selected from the group consisting of a hydroxy group, a $C_1$-$C_4$ alkoxy group and a $C_1$-$C_4$ alkyl group; $R^2$ is a $C_1$-$C_6$ alkyl group substituted with 1 to 2 substituents independently selected from the group consisting of a hydroxy group, a trifluoromethyl group, a $C_1$-$C_4$ alkylsulfonyl group, a $C_1$-$C_4$ alkylsulfonylamino group, a $C_1$-$C_4$alkyl-carbonyl group, a trifluoromethyl-carbonyl group, a $C_1$-$C_4$ alkoxy-carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl)amino-carbonyl group, a ($C_1$-$C_4$ hydroxyalkyl)($C_1$-$C_4$ alkyl)amino-carbonyl group, a heterocyclyl-carbonyl group and a $C_1$-$C_4$ alkyl-substituted heterocyclyl group; and $R^3$ is a hydrogen atom, a fluorine atom or a $C_1$-$C_2$ alkyl group;

(C) A is a carbon atom or a nitrogen atom; B is a carbon atom or a nitrogen atom; $R^1$ is an ethyl group substituted with 1 to 3 substituents independently selected from the group consisting of a methyl group; a methoxy group; an amino group; a methylamino group; a dimethylamino group; methyl(methylsulfonyl)amino; 4-morphonyl group; and 4-thiomorphonyl group; $R^2$ is a $C_1$-$C_6$ alkyl group substituted with 1 to 2 substituents independently selected from the group consisting of a hydroxy group, a trifluoromethyl group, a mercapt group, a carboxy group, a $C_1$-$C_4$ alkoxy-carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl)amino-carbonyl group, a ($C_1$-$C_4$ hydroxyalkyl)($C_1$-$C_4$ alkyl)amino-carbonyl group, a heterocyclyl-carbonyl group and a $C_1$-$C_4$ alkyl-substituted heterocyclyl group; and $R^3$ is a hydrogen atom, a fluorine atom or a $C_1$-$C_2$ alkyl group;

(D) A is a carbon atom or a nitrogen atom; B is a carbon atom; $R^1$ is an ethyl group substituted with 1 to 3 substituents independently selected from the group consisting of a methyl group; a methoxy group; an amino group; a methylamino group; a dimethylamino group; methyl(methylsulfonyl)amino; 4-morphonyl group; and 4-thiomorphonyl group; $R^2$ is a cycloalkyl group substituted with 1 to 3 substituents selected from the group consisting of a hydroxy group, a carboxy group and a $C_1$-$C_4$ alkoxy-carbonyl group; a heterocyclyl group; a heterocyclyl group substituted with 1 to 3 substituents selected from the group consisting of a hydroxy group and a $C_1$-$C_4$ alkyl group; or a $C_1$-$C_{10}$ alkyl group substituted with 1 to 3 substituents independently selected from the group consisting of a cyano group, a hydroxy group, a $C_2$-$C_4$ alkenyl group, a $C_2$-$C_4$ alkynyl group, a $C_1$-$C_4$ alkoxy group, a $C_6$-$C_{10}$ aryloxy group, a mercapt group, a $C_1$-$C_4$ alkylthio group, a $C_1$-$C_4$ alkylsulfinyl group, a $C_1$-$C_4$ alkylsulfonyl group, a $C_6$-$C_{10}$ arylthio group, a carboxy group, a $C_1$-$C_4$ alkoxy-carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl)amino-carbonyl group, a ($C_1$-$C_4$ hydroxyalkyl)($C_1$-$C_4$ alkyl)amino-carbonyl group, a heterocyclyl-carbonyl group, a cycloalkyl group, a heterocyclyl group, a $C_1$-$C_4$ alkyl-substituted heterocyclyl group and a $C_6$-$C_{10}$ aryl group; and $R^3$ is a hydrogen atom, a halogen atom, a $C_1$-$C_4$ alkyl group or a $C_1$-$C_4$ alkoxy group;

(E) A is a carbon atom or a nitrogen atom; B is a carbon atom; $R^1$ is an ethyl group substituted with 1 to 3 substituents independently selected from the group consisting of a methyl group; a methoxy group; an amino group; a methylamino group; a dimethylamino group; methyl(methylsulfonyl)amino; 4-morphonyl group; and 4-thiomorphonyl group; $R^2$ is a $C_1$-$C_6$ alkyl group substituted with 1 to 2 substituents independently selected from the group consisting of a hydroxy group, a $C_1$-$C_4$ alkylsulfonyl group, a $C_1$-$C_4$ alkoxy-carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl)amino-carbonyl group, a ($C_1$-$C_4$ hydroxyalkyl)($C_1$-$C_4$ alkyl)amino-carbonyl group, a heterocyclyl-carbonyl group and a $C_1$-$C_4$ alkyl-substituted heterocyclyl group; and $R^3$ is a hydrogen atom, a fluorine atom or a $C_1$-$C_2$ alkyl group;

(F) A is a carbon atom or a nitrogen atom; B is a carbon atom; $R^1$ is an ethyl group substituted with 1 to 3 substituents independently selected from the group consisting of a methyl group; a methoxy group; an amino group; a methylamino group; a dimethylamino group; methyl(methylsulfonyl)amino; 4-morphonyl group; and 4-thiomorphonyl group; $R^2$ is a $C_1$-$C_6$ alkyl group substituted with 1 to 2 substituents independently selected from the group consisting of a hydroxy group, an amino carbonyl group, a $C_1$-$C_2$ alkylamino-carbonyl group, a di($C_1$-$C_2$ alkyl)amino-carbonyl group, and a $C_1$-$C_2$ alkyl-substituted heterocyclyl group; and $R^3$ is a hydrogen atom, a fluorine atom or a $C_1$-$C_2$ alkyl group.

Preferred class of compounds of the present invention are those compounds of formula (I) or a pharmaceutically acceptable salt thereof, each as described herein, in which:

(a) A is a carbon atom;
(b) A is a nitrogen atom;
(c) B is a carbon atom;
(d) B is a nitrogen atom;
(e) $R^1$ is a $C_1$-$C_4$ alkyl group substituted with 1 to 3 substituents independently selected from the group consisting of a $C_1$-$C_4$ alkyl group; a hydroxy group; a $C_1$-$C_4$ alkoxy group; an amino group; a $C_1$-$C_4$ alkylamino group; a di($C_1$-$C_4$ alkyl)amino group; a ($C_1$-$C_4$ alkyl)($C_1$-$C_4$ alkylsulfonyl) amino group; a cycloalkyl group; a cycloalkyl group substituted with 1 to 3 substituents selected from the group consisting of a hydroxy group, a $C_1$-$C_4$ alkoxy group and a $C_1$-$C_4$ alkyl group; a heterocyclyl group; and a heterocyclyl group substituted with 1 to 3 substituents selected from the group consisting of a hydroxy group, a $C_1$-$C_4$ alkoxy group and a $C_1$-$C_4$ alkyl group;
(f) $R^1$ is a $C_1$-$C_2$ alkyl group substituted with 1 to 3 substituents independently selected from the group consisting of a $C_1$-$C_4$ alkyl group; a hydroxy group; a $C_1$-$C_2$ alkoxy group; an amino group; a $C_1$-$C_4$ alkylamino group; a di($C_1$-$C_4$ alkyl)amino group; a ($C_1$-$C_4$ alkyl)($C_1$-$C_4$ alkylsulfonyl) amino group; a cycloalkyl group; a cycloalkyl group substituted with 1 to 3 substituents selected from the group consisting of a hydroxy group, a $C_1$-$C_4$ alkoxy group and a $C_1$-$C_4$ alkyl group; a heterocyclyl group; and a heterocyclyl group substituted with 1 to 3 substituents selected from the group consisting of a hydroxy group, a $C_1$-$C_4$ alkoxy group and a $C_1$-$C_4$ alkyl group;
(g) $R^1$ is an ethyl group substituted with 1 to 3 substituents independently selected from the group consisting of a methyl group; a methoxy group; an amino group; a methylamino group; a dimethylamino group; methyl(methylsulfonyl)amino; 4-morphonyl group; and 4-thiomorphonyl group;
(h) $R^2$ is a cycloalkyl group substituted with 1 to 3 substituents selected from the group consisting of a hydroxy group, a $C_1$-$C_4$ hydroxyalkyl group, a carboxy group and a $C_1$-$C_4$ alkoxy-carbonyl group; a heterocyclyl group; a heterocyclyl group substituted with 1 to 3 substituents selected from the group consisting of a hydroxy group and a $C_1$-$C_4$ alkyl group; or a $C_1$-$C_{10}$ alkyl group substituted with 1 to 3 substituents independently selected from the group consisting of a cyano group, a hydroxy group, a trifluoromethyl group, a $C_2$-$C_4$ alkenyl group, a $C_2$-$C_4$ alkynyl group, a $C_1$-$C_4$ alkoxy group, a $C_6$-$C_{10}$ aryloxy group, a mercapt group, a $C_1$-$C_4$ alkylthio group, a $C_1$-$C_4$ alkylsulfinyl group, a $C_1$-$C_4$ alkylsulfonyl group, a $C_1$-$C_4$ alkylsulfonylamino group, a $C_6$-$C_{10}$ arylthio group, a carboxy group, a $C_1$-$C_4$ alkoxy-carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl)amino-carbonyl group, a ($C_1$-$C_4$ hydroxyalkyl)($C_1$-$C_4$ alkyl)amino-carbonyl group, a heterocyclyl-carbonyl group, a cycloalkyl group, a heterocyclyl group, a $C_1$-$C_4$ alkyl-substituted heterocyclyl group and a $C_6$-$C_{10}$ aryl group;
(i) $R^2$ is a $C_1$-$C_6$ alkyl group substituted with 1 to 2 substituents independently selected from the group consisting of a hydroxy group, a $C_1$-$C_4$ alkylsulfonyl group, a $C_1$-$C_4$ alkoxy-carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl)amino-carbonyl group, a ($C_1$-$C_4$ hydroxyalkyl)($C_1$-$C_4$ alkyl)amino-carbonyl group, a heterocyclyl-carbonyl group and a $C_1$-$C_4$ alkyl-substituted heterocyclyl group;
(j) $R^2$ is a $C_1$-$C_6$ alkyl group substituted with 1 to 2 substituents independently selected from the group consisting of a hydroxy group, an amino carbonyl group, a $C_1$-$C_2$ alkylamino-carbonyl group, a di($C_1$-$C_2$ alkyl)amino-carbonyl group, and a $C_1$-$C_2$ alkyl-substituted heterocyclyl group;
(k) $R^3$ is a hydrogen atom, a halogen atom, a $C_1$-$C_4$ alkyl group or a $C_1$-$C_4$ alkoxy group;
(l) $R^3$ is a hydrogen atom, a fluorine atom or a $C_1$-$C_2$ alkyl group.

Of these classes of compounds, any combination among (a) to (i) is also preferred.

One embodiment of the invention provides a compound selected from the group consisting of:

N-[(1S,2S)-1-(Aminocarbonyl)-2-methylbutyl]-3-(2-morpholin-4-ylethyl)-2-oxo-2,3-dihydro-1H-benzimidazole-1-carboxamide;

N-{(1S,2S)-[(Dimethylamino)carbonyl]-2-methylbutyl}-3-(2-morpholin-4-ylethyl)-2-oxo-2,3-dihydro-1H-benzimidazol-1-carboxamide;

N-[(1S)-1-(Aminocarbonyl)2,2-dimethylpropyl]-3-(2-morpholin-4-ylethyl)-2-oxo-2,3-dihydro-1H-benzimidazole-1-carboxamide;

N-{(1S)-2,2-Dimethyl-1-[(methylamino)carbonyl]propyl-3-(2-morpholin-4-ylethyl)-2-oxo-2,3-dihydro-1H-benzimidazole-1-carboxamide;

N-{(1S)-1-[(Dimethylamino)carbonyl]-2,2-dimethylpropyl}-3-(2-morpholin-4-ylethyl)-2-oxo-2,3-dihydro-1H-benzimidazole-1-carboxamide;

N-[(1S)-1-(Aminocarbonyl)-2,2-dimethylpropyl]-2-oxo-3-[2-(tetrahydro-2H-pyran-4-yl)ethyl]-2,3-dihydro-1H-benzimidazole-1-carboxamide;

N-[(1S)-1-(Aminocarbonyl)-2,2-dimethylpropyl]-3-(cyclopropylmethyl)-2-oxo-2,3-dihydro-1H-benzimidazol e-1-carboxamide;

N-[(1S)-1-(Aminocarbonyl)-2,2-dimethylpropyl]-3-(3-methylbutyl)-2-oxo-2,3-dihydro-1H-benzimidazole-1-carboxamide;

N-[(1S)-1-(Aminocarbonyl)-2,2-dimethylpropyl]-3-[(1-methylpiperidin-2-yl)methyl]-2-oxo-2,3-dihydro-1H-benzimidazole-1-carboxamide;

N-[(1S)-1-(Aminocarbonyl)-2,2-dimethylpropyl]-4-methyl-3-(2-morpholin-4-ylethyl)-2-oxo-2,3-dihydro-1H-benzimidazole-1-carboxamide;

N-[(1S)-1-(Aminocarbonyl)-2,2-dimethylpropyl]-3-(3-methylbutyl)-2-oxo-2,3-dihydro-1H-imidazo[4,5-c]pyridine-1-carboxamide;

N-[(1S)-1-(Aminocarbonyl)-2,2-dimethylpropyl]-3-[2-(dimethylamino)ethyl]-4-methyl-2-oxo-2,3-dihydro-1H-benzimidazole-1-carboxamide;

N-[(1S)-1-(Aminocarbonyl)-2-methylpropyl]-3-[2-(dimethylamino)ethyl]-4-methyl-2-oxo-2,3-dihydro-1H-benzimidazole-1-carboxamide;

N-((1S)-1-{[(2-Hydroxyethyl)amino]carbonyl}-2,2-dimethylpropyl)-3-(2-morpholin-4-ylethyl)-2-oxo-2,3-dihydro-1H-benzimidazole-1-carboxamide;

N-[(1S)-1-(Aminocarbonyl)-2,2-dimethylpropyl]-3-(2-morpholin-4-ylethyl)-2-oxo-2,3-dihydro-1H-imidazo[4,5-b]pyridine-1-carboxamide;

N-[(1S)-1-(Aminocarbonyl)-2-methylpropyl]-3-(2-morpholin-4-ylethyl)-2-oxo-2,3-dihydro-1H-benzimidazole-1-carboxamide;

N-[(1 S,2S)-1-(hydroxymethyl)-2-methylbutyl]-3-(2-morpholin-4-ylethyl)-2-oxo-2,3-dihydro-1H-benzimidazole-1-carboxamide;

N-[(1S)-1-(hydroxymethyl)-2,2-dimethylpropyl]-3-(2-morpholin-4-ylethyl)-2-oxo-2,3-dihydro-1H-benzimidazole-1-carboxamide;

N-[(1S)-1-(hydroxymethyl)-3-methylbutyl]-3-(2-morpholin-4-ylethyl)-2-oxo-2,3-dihydro-1H-benzimidazole-1-carboxamide;

N-{1-[(dimethylamino)carbonyl]-1,3-dimethylbutyl}-3-(2-morpholin-4-ylethyl)-2-oxo-2,3-dihydro-1H-benzimidazole-1-carboxamide;

N-[(1S)-1-(Aminocarbonyl)-2,2-dimethylpropyl]-4-chloro-3-(2-morpholin-4-ylethyl)-2-oxo-2,3-dihydro-1H-benzimidazole-1-carboxamide;

N-[(1S)-1-(Aminocarbonyl)-2,2-dimethylpropyl]-3-[(4-hydroxytetrahydro-2H-pyran-4-yl)methyl]-2-oxo-2,3-dihydro-1H-benzimidazole-1-carboxamide;

N-[(1S)-1-(Aminocarbonyl)-2,2-dimethylpropyl]-3-[2-(4-hydroxytetrahydro-2H-pyran-4-yl)ethyl]-2-oxo-2,3-dihydro-1H-benzimidazole-1-carboxamide;

N-[(1S)-1-(Aminocarbonyl)-2,2-dimethylpropyl]-3-[2-(methylsulfonyl)ethyl]-2-oxo-2,3-dihydro-1H-benzimidazole-1-carboxamide;

N-[(1S)-1-cyano-2,2-dimethylpropyl]-3-(2-morpholin-4-ylethyl)-2-oxo-2,3-dihydro-1H-benzimidazole-1-carboxamide;

N-[(1S)-(aminocarbonyl)-2,2-dimethylpropyl]-3-(2-hydroxy-2-methylpropyl)-2-oxo-2,3-dihydro-1H-benzimidazole-1-carboxamide;

N-[(1S)-1-(aminocarbonyl)-2,2-dimethylpropyl]-5-methyl-3-(2-morpholin-4-ylethyl)-2-oxo-2,3-dihydro-1H-imidazo[4,5-b]pyridine-1-carboxamide;

N-[(1S)-1-(aminocarbonyl)-2-methylpropyl]-5-methyl-3-(2-morpholin-4-ylethyl)-2-oxo-2,3-dihydro-1H-imidazo[4,5-b]pyridine-1-carboxamide;

N-[(1S)-2,2-dimethyl-1-(2-methyl-2H-tetrazol-5-yl) propyl]-3-(2-morpholin-4-ylethyl)-2-oxo-2,3-dihydro-1H-benzimidazole-1-carboxamide;

N-[(1S)-1-(aminocarbonyl)-2,2-dimethylpropyl]-3-(2-methoxy-2-methylpropyl)-2-oxo-2,3-dihydro-1H-benzimidazole-1-carboxamide;

N-[(1S)-2,2-dimethyl-1-(1-methyl-1H-tetrazol-5-yl)propyl]-3-(2-morpholin-4-ylethyl)-2-oxo-2,3-dihydro-1H-benzimidazole-1-carboxamide;

N-[(1S)-2,2-dimethyl-1-(2-methyl-2H-tetrazol-5-yl)propyl]-3-(3-hydroxy-3-methylbutyl)-2-oxo-2,3-dihydro-1H-benzimidazole-1-carboxamide; and N-[(1S)-2,2-dimethyl-1-(2-methyl-2H-tetrazol-5-yl) propyl]-3-[2-(methylsulfonyl)ethyl]-2-oxo-2,3-dihydro-1H-benzimidazole-1-carboxamide.

Another embodiment of the invention provides a compound selected from the group consisting of:

4-[3-({[2,2-dimethyl-1-(2-methyl-2H-tetrazol-5-yl)propyl]amino}carbonyl)-7-methyl-2-oxo-2,3-dihydro-1H-benzimidazol-1-yl]-2-methylbutan-2-aminium formate and 1-[3-({[2,2-dimethyl-1-(2-methyl-2H-tetrazol-5-yl)propyl]amino}carbonyl)-7-methyl-2-oxo-2,3-dihydro-1H-benzimidazol-1-yl]-2-methylpropan-2-aminium formate.

Pharmaceutically acceptable salts of a compound of formula (I) include the acid addition and base salts (including disalts) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002). A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising a compound of the invention and one or more pharmaceutically acceptable solvent molecules, for example, ethanol. The term 'hydrate' is employed when said solvent is water.

Pharmaceutically acceptable solvates in accordance with the invention include hydrates and solvates wherein the solvent of crystallization may be isotopically substituted, e.g. $D_2O$, $d_6$-acetone, $d_6$-DMSO Included within the scope of the invention are complexes such as clathrates, drug-host inclusion complexes wherein, in contrast to the aforementioned solvates, the drug and host are present in stoichiometric or non-stoichiometric amounts.

Also included are complexes of the drug containing two or more organic and/or inorganic components which may be in stoichiometric or non-stoichiometric amounts. The resulting complexes may be ionised, partially ionised, or non-ionised. For a review of such complexes, see *J Pharm Sci,* 64 (8),1269-1288 by Haleblian (August 1975).

Hereinafter all references to a compound of formula (I) include references to salts and complexes thereof and to solvates and complexes of salts thereof.

The term "compound of the invention" or "compounds of the invention" refers to, unless indicated otherwise, a compound of formula (I) as hereinbefore defined, polymorphs, prodrugs, and isomers thereof (including optical, geometric and tautomeric isomers) as hereinafter defined and isotopically-labeled compounds of formula (I).

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985). Some examples of prodrugs in accordance with the invention include:

(i) where the compound of formula (I) contains an alcohol functionality (—OH), an ether thereof, for example, replacement of the hydrogen with $(C_1-C_6)$alkanoyloxymethyl;

(ii) where the compound of formula (I) contains carboxy group, an ester thereof, for example, replacement of the OH of the carboxy with $C_1-C_8$ alkyl; and (ii) where the compound of formula (I) contains a primary or secondary amino functionality (—$NH_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topgraphy (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

All of the compounds of the formula (I) can be prepared by the procedures described in the general methods presented below or by the specific methods described in the Examples section and the Preparations section, or by routine modifications thereof. The present invention also encompasses any one or more of these processes for preparing the compounds of formula (I), in addition to any novel intermediates used therein.

General Synthesis

The compounds of the present invention may be prepared by a variety of processes well known for the preparation of compounds of this type, for example as shown in the following Methods A to D.

The following Method A illustrate the preparation of compounds of formula (I). Methods B through D illustrate the preparation of various intermediates.

Unless otherwise indicated, $R^1$, $R^2$, $R^3$, A and B in the following Methods are as defined above. The term "protecting group", as used hereinafter, means a hydroxy, carboxy or amino-protecting group which is selected from typical hydroxy, carboxy or amino-protecting groups described in *Protective Groups in Organic Synthesis* edited by T. W. Greene et al. (John Wiley & Sons, 1999). All starting materials in the following general syntheses may be commercially available or obtained by conventional methods known to those skilled in the art, such as Meth-Cohn, O.; Smith, D. I. *J. C. S., Perkin Trans.* 1, 1982, 261; Vernin, G.; Domlog, H.; Siv, C.; Metzger, J. *J. Heterocyclic Chem.* 1981, 18, 85; Emily, M. S. et al. *Tetrahedron* 2001, 57, 5303-5320; Kubo, K. et al. *J. Med. Chem.* 1993, 36, 1772-1784; Israel, M.; Jones, L. C. *J. Heterocyclic Chem.* 1971, 8, 797; Sebok, R; Levai, A.; Timar, T. *Heterocyclic Commun.* 1998, 4, 547-552.); and the disclosures of which are incorporated herein by references.

Method A

This illustrates the preparation of compounds of formula (I).

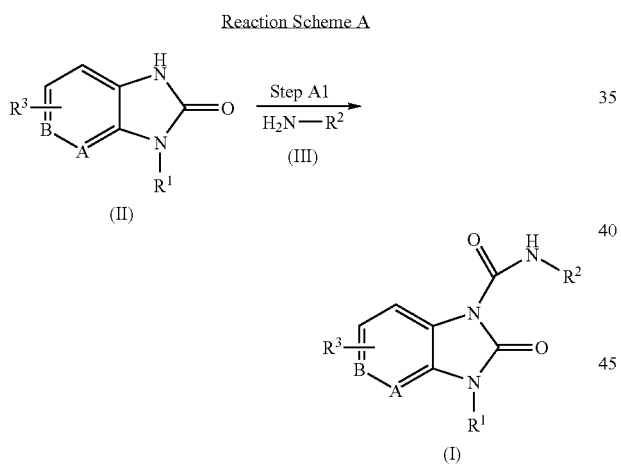

Step A1

In this step, the desired compound of formula (I) of the present invention is prepared by carbonylation of the compound of formula (II) with the compound of formula (III). The compound of formula (II) is commercially available or can be prepared according to the Methods B and C set forth below. The compound of formula (III) is commercially available.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; aromatic hydrocarbons, such as benzene, toluene and nitrobenzene; ethers, such as diethyl ether, diisopropyl ether, tetrahydrofuran and dioxane; and amides, such as N,N-dimethylformamide and N,N-dimethylacetamide. Of these solvents, dichloromethane is preferred.

There is likewise no particular restriction on the nature of the carbonylating agents used, and any carbonylating agent commonly used in reactions of this type may equally be used here. Examples of such carbonylating agents include, but are not limited to: an imidazole derivative such as N,N'-carbonyldiimidazole (CDI); a chloroformate such as trichloromethyl chloroformate and 4-nitrophenyl chloroformate; urea; and triphosgene. Of these, 4-nitrophenyl chloroformate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 5 minutes to about 24 hours will usually suffice.

Method B

This illustrates the preparation of compounds of formula (II).

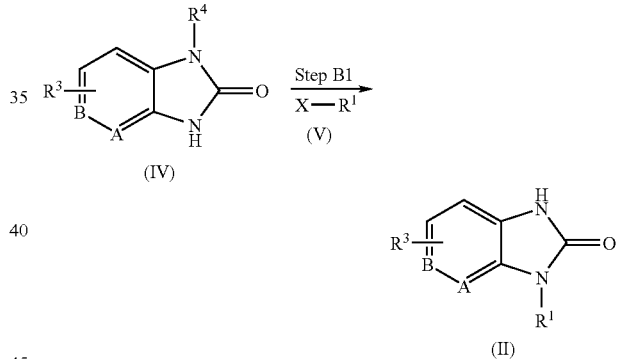

In Reaction Scheme B, $R^4$ is an amide-protecting group; X is a leaving group.

The term "amide-protecting group", as used herein, signifies a protecting group capable of being cleaved by chemical means, such as hydrogenolysis, hydrolysis, electrolysis or photolysis and such amide-protecting groups are described in Protective Groups in Organic Synthesis edited by T. W. Greene et al. (John Wiley & Sons, 1999). Typical amide-protecting groups include, but are not limited to, allyl, isopropenyl, t-butyl, methoxymethyl, benzyloxy and t-butyldimethylsilyl. Of these groups, isopropenyl is preferred.

The term "leaving group", as used herein, signifies a group capable of being substituted by nucleophilic groups, such as a hydroxy group, amines or carboanions and examples of such leaving groups include halogen atoms, a alkylsulfonyl group and a phenylsulfonyl group. Of these, a bromine atom, a chlorine atom and a methylsulfonyl group are preferred.

Step B1

In this step, the compound of formula (II) is prepared by the nucleophilic substitution (B1-a) with the compound of formula (V) followed by deprotection (B1-b). The compound of formula (IV) is commercially available or can be prepared according to the methods described in Israel, M.; Jones, L. C. *J. Heterocyclic Chem.* 1971, 8, 797. The compound of formula (V) is commercially available.

(B1-a) Nucleophilic Substitution

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; nitriles, such as acetonitrile and benzonitrile; and sulfoxides, such as dimethyl sulfoxide and sulfolane. Of these solvents, N,N-dimethylformamide is preferred.

The reaction is carried out in the presence of a base. There is likewise no particular restriction on the nature of the bases used, and any base commonly used in reactions of this type may equally be used here. Examples of such bases include: alkali metal hydrides, such as lithium hydride, sodium hydride and potassium hydride; and alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, sodium hydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 50° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours, will usually suffice.

(B1-b) Deprotection

The deprotection method is described in detail by T. W. Greene et al. [*Protective Groups in Organic Synthesis*, 494-653, (1999)], the disclosures of which are incorporated herein by reference. The following exemplifies a typical method involving the protecting group is isopropenyl.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: ethers, such as diethyl ether, diisopropyl ether, tetrahydrofuran and dioxane; water; and alcohols, such as methanol, ethanol, propanol, 2-propanol and butanol. Of these solvents, water or alcohols are preferred.

The reaction is carried out in the presence of excess amount of an acid. There is likewise no particular restriction on the nature of the acids used, and any acid commonly used in reactions of this type may equally be used here. Examples of such acids include, but are not limited to: acids, such as hydrochloric acid, sulfuric acid or trifluoroacetic acid. Of these, hydrochloric acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 25° C. to about 120° C. The time required for the reaction may also vary widely, depending on many factors, notably the reaction temperature and the nature of the starting materials and solvent employed. However, provided that the reaction is effected under the preferred conditions outlined above, a period of from about 15 minutes to about 12 hours, will usually suffice.

Method C

This illustrates the preparation of compounds of formula (II).

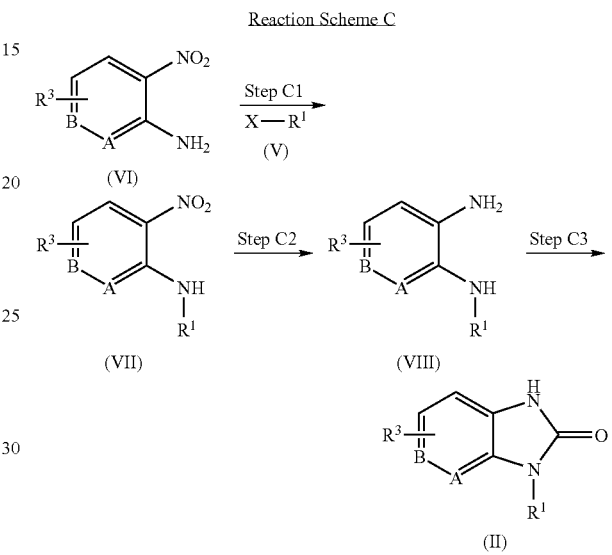

In Reaction Scheme C, X is as defined above.

Step C1

In this step, the compound of formula (VII) is prepared by the nucleophilic substitution of the compound of formula (VI) with the compound of formula (V). The compound of formula (VI) is commercially available or can be prepared according to the methods described in Kubo, K. et al. *J. Med. Chem.* 1993, 36, 1772-1784. The compound of formula (V) is commercially available. The reaction may be carried out under the same conditions as described in Step B1-a of Method B.

Step C2

In this step, the compound of formula (VIII) is prepared by the reduction of the nitro group.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; aromatic hydrocarbons, such as benzene and toluene; alcohols, such as methanol, ethanol, propanol, 2-propanol and butanol; and esters, such as ethyl acetate. Of these solvents, tetrahydrofuran is preferred.

The reaction is carried out in the presence of a reducing agent. There is likewise no particular restriction on the nature of the reducing agents used, and any reducing agent commonly used in reactions of this type may equally be used here. Examples of such reducing agents include: hydride compounds such as lithium aluminum hydride, sodium borohydride and diisobutyl aluminum hydride; combinations of hydrogen gas and a catalyst such as palladium-carbon, platinum and Raney nickel; and a combination of metals, such as zinc and iron, and acids, such as hydrochloric acid, acetic acid and acetic acid-ammonium chloride complex. Of these, lithium aluminum hydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 25° C. to about 120° C. The time required for the reaction may also vary widely, depending on many factors, notably the reaction temperature and the nature of the starting materials and solvent employed. However, provided that the reaction is effected under the preferred conditions outlined above, a period of from about 15 minutes to about 24 hours will usually suffice.

Step C3

In this step, the compound of formula (II) is prepared by the formation of the cyclic urea of the compound of formula (VIII).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; aromatic hydrocarbons, such as benzene, toluene and nitrobenzene; ethers, such as diethyl ether, diisopropyl ether, tetrahydrofuran and dioxane; and amides, such as N,N-dimethylformamide and N,N-dimethylacetamide. Of these solvents, tetrahydrofuran is preferred.

There is likewise no particular restriction on the nature of the carbonylating agents used, and any carbonylating agent commonly used in reactions of this type may equally be used here. Examples of such carbonylating agents include, but are not limited to: an imidazole derivative such as N,N'-carbonyldiimidazole (CDI); a chloroformate such as trichloromethyl chloroformate and 4-nitrophenyl chloroformate; urea; and triphosgene. Of these, CDI or urea is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 12 hours will usually suffice.

Method D

This illustrates the preparation of compounds of formula (II).

Reaction Scheme D

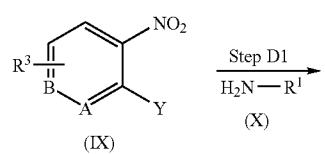

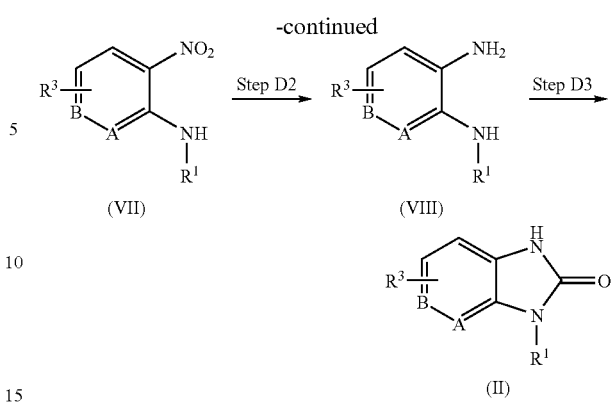

In Reaction Scheme C, Y is a chlorine atom or fluorine atom.

Step D1

In this step, the compound of formula (VII) is prepared by the nucleophilic substitution of the compound of formula (IX) with the compound of formula (X). The compound of formula (IX) is commercially available or can be prepared according to the methods described in Orjales, A. et al. *J. Med. Chem.* 1999, 42, 2870-2880. The compound of formula (X) is commercially available.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: halogenated hydrocarbons, such as dichloromethane, chloroform, carbon tetrachloride and 1,2-dichloroethane; aromatic hydrocarbons, such as benzene, toluene and nitrobenzene; ethers, such as diethyl ether, diisopropyl ether, tetrahydrofuran and dioxane; alcohols, such as methanol, ethanol, propanol, 2-propanol and butanol; and amides, such as N,N-dimethylformamide and N,N-dimethylacetamide. Of these solvents, tetrahydrofuran is preferred.

The reaction is carried out in the presence of a base. There is likewise no particular restriction on the nature of the bases used, and any base commonly used in reactions of this type may equally be used here. Examples of such bases include: alkali metal alkoxides, such as sodium methoxide, sodium ethoxide and potassium t-butoxide; alkali metal carbonates, such as lithium carbonate, sodium carbonate and potassium carbonate; amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU); and alkali metal hydrogencarbonates, such as lithium hydrogencarbonate, hydrogen sodium carbonate and potassium hydrogencarbonate. Of these, potassium carbonate is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −20° C. to about 120° C. The time required for the reaction may also vary widely, depending on many factors, notably the reaction temperature and the nature of the starting materials and solvent employed. However, provided that the reaction is effected under the preferred conditions outlined above, a period of from about 1 hour to about 36 hours will usually suffice.

In this reaction, microwave can be employed to accelerate the reaction. In the case of employing microwave, the reaction at a temperature may be from about 50° C. to about 220° C. and the reaction time from about 5 minutes to about 6 hours will usually suffice.

Steps D2 and D3

The reactions may be carried out under the same conditions as described in Steps C2 and C3.

The compounds of formula (I), and the intermediates above-mentioned preparation methods can be isolated and purified by conventional procedures, such as distillation, recrystallization or chromatographic purification.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a pharmaceutical composition or formulation in association with one or more pharmaceutically acceptable carriers or excipients. The term "carrier" or "excipient" is used herein to describe any ingredient other than the compound(s) of the invention. The choice of carrier or excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as, for example, tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include, for example, suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in *Expert Opinion in Therapeutic Patents*, 11 (6), 981-986 by Liang and Chen (2001).

For tablet dosage forms, depending on dose, the drug may make up from about 1 wt % to about 80 wt % of the dosage form, more typically from about 5 wt % to about 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from about 1 wt % to about 25 wt %, preferably from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 wt % to about 10 wt %, preferably from about 0.5 wt % to about 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "*Pharmaceutical Dosage Forms: Tablets, Vol. 1*", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, *Pharmaceutical Technology On-line*, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from about 3 to about 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, *J Pharm Sci*, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from about 1 µg to about 20 mg of the compound of the invention per actuation and the actuation volume may vary from about 1 µl to about 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from about 1 to about 100 pg of the compound of formula (I). The overall daily dose will typically be in the range about 50 pg to about 20 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in. WO 91/11172, WO 94/02518 and WO 98/55148.

Kit-of-Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range of about 0.05 mg to about 100 mg depending, of course, on the mode of administration, preferred in the range of about 0.1 mg to about 50 mg and more preferred in the range of about 0.5 mg to about 20 mg. For example, oral administration may require a total daily dose of from about 1 mg to about 20 mg, while an intravenous dose may only require from about 0.5 mg to about 10 mg. The total daily dose may be administered in single or divided doses.

These dosages are based on an average human subject having a weight of about 65 kg to about 70 kg. The physician will readily be able to determine doses for subjects whose weight falls outside this range, such as infants and the elderly.

Combination

As discussed above, a compound of the invention exhibits CB2 receptor binding activity. A CB2 ligand of the present invention may be usefully combined with another pharmacologically active compound, or with two or more other pharmacologically active compounds, particularly in the treatment of the cancer, inflammatory diseases, immunomodulatory diseases and gastrointestinal disorder. For example, a CB2 ligands, particularly a compound of the formula (I), or a pharmaceutically acceptable salt thereof, as defined above, may be administered simultaneously, sequentially or separately in combination with one or more agents selected from:

(i) 5-$HT_3$ antagonists, e.g. dolasetron, palonosetron, alosetron, azasetron and ramosetron, mitrazapine, granisetron, tropisetron, E-3620, ondansetron and indisetron;

(ii) 5-$HT_4$ agonists, e.g. tegaserod, mosapride, cinitapride and oxtriptane;

(iii) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine Modulon® (trimebutine malate), Imodium® (loperamide) and pentazocine;

(iv) tricyclic antidepressants, e.g. imipramine, amitriptyline, clomipramine, amoxapine and lofepramine;

(v) somatostatin analogues, e.g. octreotide, AN-238 and PTR-3173;

(vi) anticholinergics, e.g. dicyclomine and hyoscyamine, ipratropium bromide, ipratropium, tiotropium bromide;

(vii) laxatives, e.g. Trifyba®, Fybogel®, Konsyl®, Isogel®, Regulan®, Celevac® and Normacol®;

(viii) fiber products, e.g. Metamucil®;

(ix) antispasmodics, e.g.: mebeverine;

(x) dopamine antagonists, e.g. metoclopramide, domperidone and levosulpiride;

(xi) cholinergics, e.g. neostigmine, pilocarpine, carbachol (xii) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xiii) Cl Channel activator: e.g. lubiprostone;

(xiv) selective serotonin reuptake inhibitors, e.g. sertraline, escitalopram, fluoxetine, nefazodone, fluvoxamine, citalopram, milnacipran, paroxetine, venlafaxine, tramadol, sibutramine, duloxetine, desvenlafaxine and depoxetine;

(xv) GABA agonists, e.g. gabapentin, topiramate, cinolazepam, clonazepam, progabide, brotizolam, zopiclone, pregabalin and eszopiclone;

(xvi) tachykinin (NK) antagonists, particularly NK-3, NK-2 and NK-1 antagonists, e.g.: nepadutant, saredutant, talnetant, (αR,9R)-7-[3,5-bis(trifluoromethyl)benzyl]-8,9,10, 11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl] ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl] methylamino]-2-phenyl-piperidine (2S,3S).

(xvii) α2 agonists, e.g. clonidine, medetomidine, lofexidine, moxonidine, tizanidine, guanfacine, guanabenz, talipexole and dexmedetomidine;

(xviii) benzodiazepine agonists, e.g. diazepam, zaleplon, zolpidem, haloxazolam, clonazepam, prazepam, quazepam, flutazolam, triazolam, lormetazepam, midazolam, tofisopam, clobazam, flunitrazepam and flutoprazepam;

(xix) prostaglandin analogues, e.g. Prostaglandin, misoprostol, treprostinil, esoprostenol, latanoprost, iloprost, beraprost, enprostil, ibudilast and ozagrel;

(xx) histamine $H_3$ agonists, e.g. R-alpha-methylhistamine and BP-294;

(xxi) anti-gastric agents, e.g. Anti-gastrin vaccine, itriglumide and Z-360;

(xxii) disease modifying anti-rheumatic drugs (DMARDs), e.g. methotrexate, leflunomide, penicillamine aurothiopropanol sulfonate, sulfasalazine, mesalamine, olsalazine, balsalazide, Hylan G-F 20, glucosamine, chondroitin sulfate, hydroxychloroquine and diacerein.

(xxiii) Tumor Necrosis Factor-Alpha (TNF-α) modulators, e.g. etanercept, infliximab, adalimumab, CDP-870, pegsunercept, ISIS-104838, RDP-58 and thalidomide;

(xxiv) interleukin-based therapies, e.g. anakinra, atlizumab, RGN-303, denileukindiftitox, ilodecakin, oprelvekin and mepolizumab;

(xxv) nonsteroidal antiinflammatory drugs (NSAIDs), e.g. piroxicam, naproxen, indomethacin, ibuprofen, diclofenac, ketorolac, flurbiprofen, aspirin, diflusinal, etodolac, fenbufen, fenoprofen, flufenisal, ketoprofen, meclofenamic acid, mefenamic acid, nabumetone, oxaprozin, phenylbutazone, sulindac, tolmetin and zomepirac;

(xxvi) selective COX-2 Inhibitors, e.g. celecoxib, rofecoxib, valdecoxib, etoricoxib, lumiracoxib and LAS-34475;

(xxvii) Centrally Acting Analgesics, e.g. tramadol and oxymorphone ER;

(xxviii) immunosupressives, e.g. cyclosporine, tacrolimus, rapamycin, azathioprine and mycophenolate mofetil;

(xxix) Multiple Sclerosis(MS) treatments, e.g. interferonβ-1b, interferonβ-1a, glatiramer acetate, mitoxantrone, cyclophosphamide, MBP-8298, AG-284, tiplimotide, BX-471, E-2007, recombinant glial growth factor-2 and natalizumab;

(xxx) Monoclonal Antibodies, e.g. natalizumab, daclizumab, alemtuzumab, omalizumab, TNX-100 and SGN-40;

(xxxi) insulin secretagogues, e.g. glyburide, glipizide, repaglinide and glimiperide;

(xxxii) biguanides, e.g. metformin;

(xxxiii) alpha-glucosidase inhibitors, e.g. acarbose, voglibose and miglitol;

(xxxiv) PPAR γ agonists, e.g. pioglitazone and rosiglitazone;

(xxxv) antibiotics, e.g. sulfacetamide, erythromycin, gentamicin, tobramycin, ciprofloxacin and ofloxacin (xxxvi) cell adhesion molecule inhibitors, e.g. alicaforsen, MLN-02, alefacept, efalizumab, R-411 and IVL-745;

(xxxvii) anti-allergy drugs, e.g. levocabastine, olopatadine, cromolyn, lodoxamide, pheniramine, ketotifen, mizolastine and epinastine;

(xxxviii) opthalmologic anti-virals, e.g. adenine arabinoside and idoxuridine;

(xxxix) glaucoma treatments, e.g. timolol, metipranolol, carteolol, betaxolol, levobunolol, brimonidine, iopidine, dorzolamide, epinephrine and dipivefrin;

(xl) alkylating anti-tumor agents, e.g. busulfan, carboplatin, chlorambucil, cisplatin, cyclophosphamide, dacarbazine, ifosfamide, mechlorethamine, melphalan, procarbazine, thiotepa, and uracil mustard;

(xli) nitrosoureas, e.g. carmustine, lumustine and streptozocin;

(xlii) antimetabolites, e.g. 5-fluorouracil, 6-mercaptopurine, capecitabine, cytosine arabinoside, floxuridine, fludarabine, gemcitabine, methotrexate, thioguanine and azathioprine;

(xliii) antitumor biotics, e.g. dactinomycin, daunorubicin, doxorubicin, idarubicin, mitomycin-C, and mitoxantrone;

(xliv) anti-microtuble agents, e.g. vinblastine, vincristine, vindesine, vinorelbine, paclitaxel and docetaxel;

(xlv) vitamine derivatives, e.g., calcipotriol and tacalcitol;

(xlvi) leukotriene antagonists, e.g. montelukast, zafirlukast and pranlukast;

(xlvii) β2 Agonists, e.g. albuterol, levalbuterol, salmeterol, formotero and arformoterol;

(xlviii) corticosteroids, e.g. prednisone, ciclesonide, budesonide, fluticasone, methylprednisolone, hydrocortisone and BP-1011;

(xlix) methylxanthines, e.g. theophylline, aminophylline and doxofylline; and (l) asthma and/or COPD treatments, e.g. roflumilast, tiotropium, israpafant, N-acetylcysteine and α1-antitrypsin.

(li) a vanilloid receptor agonist (e.g. resinferatoxin) or antagonist (e.g. capsazepine);

(lii) an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid; and (liii) a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid.

Method for Assessing Biological Activities:

The CB2 receptor binding affinity and other biological activities of the compounds of this invention are determined by the following procedures.

Rat CB2 Binding

Rat spleen cells were placed in tissue preparation buffer [5 mM Tris-HCl (pH7.4 at 25° C.) and 2 mM EDTA] and homogenized using a hand held Polytron PT1200CL disrupter set at 25,000 rpm for 30 seconds on ice, then kept on ice for 15 min. The homogenates were centrifuged at 1,000×g at 4° C. for 10 min. The supernatant was recovered and centrifuged at 40,000×g at 4° C. for 10 min. The pellets were then resuspended in 50 mM Tris-HCl (pH7.4 at 25° C.). This suspension was centrifuged once more in the same manner. The final pellet was resuspended in TME buffer (25 mM Tris-HCl (pH7.4), 5 mM $MgCl_2$, 1 mM EDTA, 0.5% BSA), aliquoted and stored at −80° C. until assayed. An aliquot was used for the determination of protein concentration using BCA™ protein assay kit (PIERCE) and the measurement was made on Wallac 1420 ARVOsx multilabel counter with BSA as a standard.

For the binding experiments, 20 μl of test compounds were incubated with 20 μl of [$^3$H] CP55,940 (Perkin Elmer, final 1 nM) and 160 μl of membrane homogenate (1 μg protein/tube) for 60 minutes at 37° C. Nonspecific binding was determined by 1 μM CP55,940 (TOCRIS Cookson Inc) at the final concentration. All incubations were harvested by vacuum filtration through GF/B fiber filters pre-soaked in 5% BSA in TME buffer using Uni-Filter cell harvester (Packard). Filters were rinsed with wash buffer (25 mM Tris-HCl (pH7.4), 5 mM $MgCl_2$, 1 mM EDTA) and then dried up at 50° C. for 30 min. The radioactivity was measured by scintillation counting using Top-Count Microplate Scintillation Counter (Packard). Rat CB1 binding affinities were also determined by a method similar to the above by using rat whole brains.

All compounds of Examples showed selective CB2 receptor affinity.

Human CB2 Binding

Human CB2 transfected Chinese hamster ovary K1 (CHO-K1) cells were established and grown to 60-80% confluence. The collected cell pastes were washed with cold PBS, suspended in 50 mM Tris-HCl (pH7.4 at 25° C.) containing protease inhibitor cocktail and homogenized using a hand held Polytron PT 1200 disruptor set at 25,000 rpm for 30 seconds on ice. The homogenates were centrifuged at 1,000×g at 4° C. for 10 min. The supernatant was recovered and centrifuged at 40,000×g at 4° C. for 10 min. The pellets were then resuspended in 50 mM Tris-HCl (pH7.4 at 25° C.). This suspension was centrifuged once more in the same manner. The final pellet was resuspended in TME buffer (25 mM Tris-HCl (pH7.4), 5 mM $MgCl_2$, 1 mM EDTA, 0.5% BSA), aliquoted and stored at −80° C. until assayed. An aliquot was used for the determination of protein concentration using BCA™ protein assay kit (PIERCE) and the measurement was made on Wallac 1420 ARVOsx multilabel counter with BSA as a standard.

For the binding experiments, 20 µl of test compounds were incubated with 20 µl of [$^3$H] CP55,940 (Perkin Elmer, final 1 nM) and 160 µl of membrane homogenate (1 µg protein/tube) for 60 minutes at 37° C. Nonspecific binding was determined by 1 µM CP55,940 (TOCRIS Cookson Inc) at the final concentration. All incubations were harvested by vacuum filtration through GF/B fiber filters pre-soaked in 5% BSA in TME buffer using Uni-Filter cell harvester (Packard). Filters were rinsed with wash buffer (25 mM Tris-HCl (pH7.4), 5 mM $MgCl_2$, 1 mM EDTA) and then dried up at 50° C. for 30 min. The radioactivity was measured by scintillation counting using Top-Count Microplate Scintillation Counter (Packard). Human CB1 binding affinities were also determined by a method similar to the above by using Human CB1 transfected Chinese hamster ovary-K1 (CHO-K1) cells, [$^3$H] SR141716A (Amersham Bioscience) and AM251 (TOCRIS Cookson Inc).

All compounds of Examples showed selective CB2 receptor affinity.

Agonist-Induced cAMP Change in Human CB2 Transfected CHO-K1 Cells

Human CB2 transfected Chinese hamster ovary-K1 (CHO-K1) cells were established and grown to 60-80% confluence. The medium was changed to F-12 medium containing 10% dialysed FBS, and the cells were incubated overnight. On the day of the assay, the cells were harvested with PBS/1 mM EDTA, centrifuged and washed with PBS. Cell pellets were resuspended in the incubation buffer (F-12 medium, 20 mM HEPES, 1 mM IBMX, 0.1 mM Ro-20-1724) at the concentration of 1×10$^5$ cells/ml and pre-incubated for 15 min at room temperature. The agonist samples were diluted from 10 mM stock solution in DMSO and dispensed into 96-well half-area plates (12.5 µl/well) with assay buffer (F-12, 20 mM HEPES). The reaction was initiated by adding the cells (25 µl/well) into the well containing forskolin (12.5 µl/well, final 5 µM) and diluted compounds. After incubation for 30 minutes at 37° C., cAMP-XL665 conjugated, and then the anti-cAMP-cryptase conjugate was added to the lysate (25 µl/well each). After further incubation for 60 minutes at room temperature, measurements were made on the Wallac 1420 ARVOsx multilabel counter (Excitation 320 nm, Emission 665 nm/620 nm, delay time 50 µs, window time 400 µs). Data analysis was made based on the ratio of fluorescence intensity of each well at 620 nm and 665 nm. The equation "sigmoidal dose-response" was used for the determination of $EC_{50}$ and Emax values.

Human Dofetilide Binding

Human HERG transfected HEK293S cells were prepared and grown in-house. The collected cells were suspended in 50 mM Tris-HCl (pH 7.4 at 4° C.) and homogenized using a hand held Polytron PT 1200 disruptor set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM $MgCl_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac).

Binding assays were conducted in a total volume of 200 µl in 96-well plates. Twenty µl of test compounds were incubated with 20 µl of [$^3$H]-dofetilide (Amersham, final 5 nM) and 160 µl of membrane homogenate (25 pg protein) for 60 minutes at room temperature. Nonspecific binding was determined by 10 µM dofetilide at the final concentration. Incubation was terminated by rapid vacuum filtration over 0.5% presoaked GF/B Betaplate filter using Skatron cell harvester with 50 mM Tris-HCl, 10 mM KCl, 1 mM $MgCl_2$, pH 7.4 at 4° C. The filters were dried, put into sample bags and filled with Betaplate Scint. Radioactivity bound to filter was counted with Wallac Betaplate counter.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.5 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consisted of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media was removed and test compound solution (10 µM) in buffer was added to the apical compartment. The inserts were moved to wells containing fresh basolateral buffer at 1 hr. Drug concentration in the buffer was measured by LC/MS analysis.

Flux rate (F, mass/time) was calculated from the slope of cumulative appearance of substrate on the receiver side and apparent permeability coefficient ($P_{app}$) was calculated from the following equation.

$$P_{app}(cm/sec) = (F*VD)/(SA*MD)$$

where SA is surface area for transport (0.3 cm$^2$), VD is the donor volume (0.3 ml), MD is the total amount of drug on the donor side at t=0. All data represent the mean of 2 inserts. Monolayer integrity was determined by Lucifer Yellow transport.

Half-Life in Human Liver Microsomes (HLM)

Test compounds (1 μM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

Half-life=ln 2/k

TNBS-Induced Chronic Colonic Allodynia in the Rat

Male IGS (Sprague-Dawley) rats, 240-270 g (7 weeks, Charles River Japan) are used. Environment conditions are controlled at a 12-h light/dark cycle with lights on at 07:00 and an ambient temperature of 23+/−2° C. Rats are housed under this condition for 4 days before the surgery. Each group is used a group of 6-8 rats. Rats are fasted for 24 hours before use. After weighing and administration of the anesthetic (Ketamine/Xylazine), the animal is placed in the dorsal decubitus position. The abdomen is shaved and disinfected with 10% povidoneiodine solution (isodine). A 2-cm long median laparotomy is conducted by making the incision 3 cm from the sternum. The cecum is then found, grasped with the fingers, removed from the abdominal cavity and placed on a compress that has been previously moistened with isotonic saline. TNBS (Fluka; 50 mg/kg; 1.5 ml/kg in 30% EtOH) is injected into the proximal colon (1 cm from the cecum). Sham group's animal undergoes the same surgery but TNBS is not injected. After injection, the intestines are put back into the abdominal cavity. The muscle wall is sutured with silk, using two cross-stitches. The skin is also sutured. After 7 days from the surgery, the balloon (5 cm in length) is inserted through the anus and kept in position (tip of balloon is 5 cm from the anus) by taping the catheter to the base of the tail. The animals are individually placed without restraint in cages for distention session. The balloon is progressively inflated by step of 5 mm Hg, from 0 to 70 mm Hg, each step of inflation lasting 30 s. Each cycle of colonic distention is controlled by a standard barostat (G&J Electronic Inc. CANADA). The pain threshold corresponds to the pressure that produced the first abdominal contraction. The abdominal contraction corresponds to waves of contraction of oblique musculature with inward turning of the hindlimb, or to humpbacked position, or to squashing of the lower abdomen against the floor (Wesselmann U et al., (1998) Neurosci Lett 246: 73-76). To determine the basal colonic threshold, two cycles of distention are performed on the same animal with an interval of >10 min before compound administration. The 1st distention is conducted to acclimate the rat to the colonic distention. The baseline is determined by the second distention. The effect of a test compound on the colonic threshold is investigated at X min post dosing. If necessary, the time course of effect of a test compound may be studied at different times.

Distribution of the treatment groups is as follows:

|  | Injection of TNBS | Treatment |
|---|---|---|
| Sham control group | No | Vehicle |
| TNBS control group | Yes | Vehicle |
| Treated group | Yes | Test compound |

The data are expressed as median threshold (mmHg) required to induce abdominal contractions in each group (vertical bars represent 1st and 3rd quartiles). Data are analyzed using Kruskal-Wallis test followed by Mann-Whitney U-test.

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 $F_{254}$ precoated TLC plates or Merck $NH_2$ gel (an amine coated silica gel) $F_{254s}$ precoated TLC plates), mass spectrometry, nuclear magnetic resonance spectra (NMR), infrared absorption spectra (1R) or microanalysis. Yields are given for illustrative purposes only. Workup with a cation-exchange column was carried out using SCX cartridge (Varian Bond-Elute), which was preconditioned with methanol. Flash column chromatography was carried out using Merck silica gel 60 (63-200 μm), Wako silica gel 300HG (40-60 μm), Fuji Silysia NH gel (an amine coated silica gel) (30-50 μm), Biotage KP-SIL (32-63 μm) or Biotage AMINOSILICA (an amine coated silica gel) (40-75 μm). Preparative TLC was carried out using Merck silica gel 60 $F_{254}$ precoated TLC plates (0.5 or 1.0 mm thickness). Low-resolution mass spectral data (EI) were obtained on an Integrity (Waters) mass spectrometer. Low-resolution mass spectral data (ESI) were obtained on ZMD™ or ZQ™ (Waters) and mass spectrometer. NMR data were determined at 270 MHz (JEOL JNM-LA 270 spectrometer), 300 MHz (JEOL JNM-LA300 spectrometer) or 600 MHz (Bruker AVANCE 600 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, bs=broad singlet, etc. IR spectra were measured by a Fourier transform infrared spectrophotometer (Shimazu FTIR-8300). Chemical symbols have their usual meanings; bp (boiling point), mp (melting point), rt (room temperature), L (liter(s)), mL (milliliter(s)), g (gram(s)), mg (milligram(s)), mol (moles), mmol (millimoles), eq. (equivalent(s)), quant. (quantitative yield). Following abbreviations may be used in examples: CDI (N,N'-carbonyldiimidazole), DMF (N,N-dimethylformamide), DMSO (dimethylsulfoxide), EDAPC (1-ethyl-3-(3-dimethylaminopropyl)carbodiimide hydrochloride), EtOH (ethanol), HOBt (1-Hydroxy-1H-benzotriazole), MeOH (methanol), and THF (tetrahydrofuran). Rt means retention time measured by LC/MS (Waters 2790) under the following condition;

Column: Xterra, C18, sum, 4.6×50 mm (40° C.)
flow: 2.0 mL/min
Gradient: Water/MeOH/1% $HCO_2H$ aq.=90/5/5 to 0/95/5
Total run time: 2.5 minutes.

Example 1

N-[(1S,2S)-1-(Aminocarbonyl)-2-methylbutyl]-3-(2-morpholin-4-ylethyl)-2-oxo-2,3-dihydro-1H-benzimidazole-1-carboxamide hydrochloride

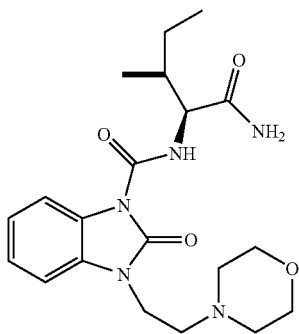

Step 1. N-(2-Morpholin-4-ylethyl)-2-nitroaniline

To a mixture of 1-fluoro-2-nitrobenzene (6 g, 43.0 mmol) and potassium carbonate (12 g, 86 mmol) in THF (80 mL) was added 4-(2-aminoethyl)morpholine (6.8 mL, 52.0 mmol) at 0° C. The mixture was stirred for 25 h at rt. Then the mixture was filtered through a pad of Celite and concentrated in vacuo. The residue was purified by column chromatography on silica gel eluting with hexane/ethyl acetate (2/1) to afford 10.4 g (97%) of the title compound.

$^1$H-NMR (270 MHz, CDCl$_3$) δ 8.50 (bs, 1H), 8.18 (dd, J=8.6, 1.49 Hz, 1H), 7.47-7.41 (m, 1H), 6.82 (d, J=8.6 Hz, 1H), 6.67-6.62 (m, 1H), 3.78-3.74 (m, 4H), 3.40-3.34 (m, 2H), 2.73 (t, J=6.1 Hz, 2H), 2.55-2.52 (m, 4H).

MS (ESI) m/z 252 (M+H)$^+$.

Step 2. N-(2-Morpholin-4-ylethyl)benzene-1,2-diamanine

To a solution of N-(2-morpholin-4-ylethyl)-2-nitroaniline (10 g, 42 mmol) in THF (100 mL) was added 10% Pd/C (1 g). The flask was evacuated and flushed with H$_2$ gas and this process was repeated three times. The flask was filled with H$_2$ gas (4 atm) and stirred for 4 h at rt. Then the reaction mixture was filtered through a pad of Celite and concentrated in vacuo to give the title compound (crude; 9.0 g)

$^1$H-NMR (300 MHz, CDCl$_3$) δ 6.82-6.64 (m, 4H), 3.71 (t, J=4.6 Hz, 4H), 3.40 (bs, 2H), 3.19-3.15 (m, 2H), 2.69-2.65 (m, 2H), 2.48 (t, J=4.6 Hz, 4H).

MS (ESI) m/z 222 (M+H)$^+$.

Step 3. 1-(2-Morpholin-4-ylethyl)-1,3-dihydro-2H-benzimidazol-2-one

To a solution of N-(2-morpholin-4-ylethyl)benzene-1,2-dimanine in THF (100 mL) was added CDI (10 g, 62 mmol) and the mixture was stirred at rt. After 23 h, the mixture was evaporated in vacuo and to the residue was added water (100 mL) at 0° C. The mixture was extracted with ethyl acetate (100 mL×2) and the combined organic layers were washed with water (50 mL), brine (50 mL), dried over sodium sulfate, filtered and concentrated in vacuo. The residue was purified by column chromatography on silica gel eluting with dichloromethane/methanol (30/1) to afford 8.5 g (83%) of the title compound.

$^1$H-NMR (300 MHz, CDCl$_3$) δ 10.4 (s, 1H), 7.13-7.01 (m, 4H), 4.03 (t, J=6.8 Hz, 2H), 3.70 (t, J=4.6 Hz, 4H), 2.72 (t, J=6.8 Hz, 2H), 2.57 (t, J=4.6 Hz, 4H).

MS (ESI) m/z 248 (M+H)$^+$, 246 (M−H)$^−$.

IR (KBr) ν$_{max}$ 2851, 1697, 1491, 1402, 1117 cm$^1$.

mp 131.0° C.

Step 4. N-[(1S 2S)-1-(Aminocarbonyl)-2-methylbutyl]-3-(2-morpholin-4-ylethyl)-2-oxo-2,3-dihydro-1H-benzimidazole-1-carboxamide hydrochloride To a solution of 1-(2-morpholin-4-ylethyl)-1,3-dihydro-2H-benzimidazol-2-one (530 mg, 2.1 mmol) in dichloromethane (8 mL) were added triethylamine (1.0 mL, 7.0 mmol) and 4-nitrophenyl chloroformate (470 mg, 2.3 mmol) at 0° C. and the mixture was stirred for 3 h at rt. Then to this mixture was added a mixture of L-isoleucinamide hydrochloride (430 mg, 2.6 mmol) and triethylamine (0.6 mL, 4.3 mmol) in dichloromethane (4 mL) at 0° C. and stirred rt. After 22 h, the reaction was quenched by addition of water (50 mL) and extracted with dichloromethane (50 mL×2). The combined organic layers were washed with water (20 mL×3), brine (20 mL) and dried over sodium sulfate, filtered and concentrated. The residue was purified by column chromatography on silica gel eluting with hexane/ethyl acetate (1/4) to afford 600 mg (70%) of free form of the title compound. The obtained compound was dissolved in ethyl acetate (1 mL) and to this solution was added 4N HCl in ethyl acetate (0.4 mL) to form white solid which was filtered and dried in vacuo to give the title compound (600 mg).

$^1$H-NMR (300 MHz, CDCl$_3$) δ 10.91 (bs, 1H), 9.00 (d, J=8.1 Hz, 1H), 8.06 (d, J=7.8 Hz, 1H), 7.68 (s, 1H), 7.50 (d, J=8.1 Hz, 1H), 7.31-7.18 (m, 3H), 4.38-4.30 (m, 3H), 4.04-3.99 (m, 2H), 3.78-3.70 (m, 2H), 3.65-3.57 (m, 2H), 3.53-3.45 (m, 2H), 3.21-3.17 (m, 2H), 1.89-1.83 (m, 1H), 1.56-1.45 (m, 1H), 1.17-1.03 (m, 1H), 0.94 (d, J=6.9 Hz, 3H), 0.89 (t, J=7.2 Hz, 3H).

MS (ESI) m/z 404 (M+H)$^+$.

Anal. calcd. for C$_{20}$H$_{29}$N$_5$O$_4$ (+0.8H$_2$O, 1.0HCl): C, 52.87; H, 7.01; N, 15.41; O, 16.90; Cl, 7.80. Found: C, 53.00; H, 7.23; N, 15.01.

Example 2

Methyl N-{[3-(2-Morpholin-4-ylethyl)-2-oxo-2,3-dihydro-1H-benzimidazole-1-yl]carbonyl}-L-isoleucinate

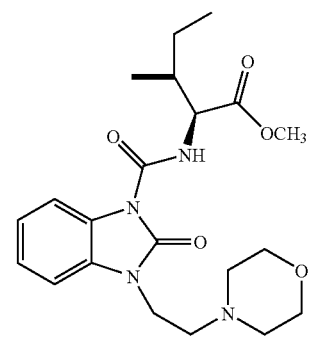

The titled compound was prepared according to the procedure described in Step 4 of example 1 from methyl L-isoleucinate hydrochloride.

$^1$H-NMR (300 MHz, CDCl$_3$) δ 9.29 (d, J=8.1 Hz, 1H), 8.20-8.17 (m, 1H), 7.24-7.13 (m, 2H), 7.05-7.02 (m, 1H), 4.62 (dd, J=8.1, 4.8 Hz, 1H), 4.02 (t, J=6.9 Hz, 2H), 3.78 (s, 3H), 3.69-3.66 (m, 4H), 2.70 (t, J=6.6 Hz, 2H), 2.54 (bs, 4H), 2.12-2.05 (m, 1H), 1.61-1.48 (m, 1H), 1.35-1.24 (m, 1H), 1.03 (d, J=6.9 Hz, 3H), 0.97 (t, J=7.2 Hz, 3H).

MS (ESI) m/z 419 (M+H)$^+$.

Example 3

N-{(1S,2S)-1-[(Dimethylamino)carbonyl]-2-methylbutyl}-3-(2-morpholin-4-ylethyl)-2-oxo-2,3-dihydro-1H-benzimidazol-1-carboxamide

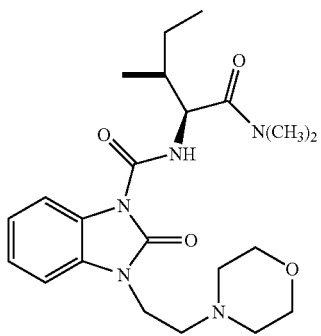

Step 1. N-{[3-(2-Morpholin-4-ylethyl)-2-oxo-2,3-dihydro-1H-benzimidazol-1-yl]carbonyl}-L-isoleucine hydrochloride A suspension of methyl N-{[3-(2-morpholin-4-ylethyl)-2-oxo-2,3-dihydro-1H-benzimidazol-1-yl]carbonyl}-L-isoleucinate (Example 2) in 4N HCl (4 mL) and acetic acid (4 mL) was refluxed for 24 h. Then it was cooled to rt and evaporated to dryness. Recrystallization from ethyl acetate and hexane followed by filtration gave 510 mg (81%) of the title compound as white solid.

$^1$H-NMR (300 MHz, DMSO-d$_6$) δ 9.08 (d, J=8.1 Hz, 1H), 8.35 (bs, 1H), 8.05 (d, J=7.2 Hz, 1H), 7.53 (d, J=7.5 Hz, 1H), 7.29 (t, J=7.5 Hz, 1H), 7.21 (t, J=7.2 Hz, 1H), 4.43-4.39 (m, 3H), 4.07-3.95 (m, 2H), 3.30-3.05 (m, 10H), 2.00-1.95 (m, 1H), 1.53-1.44 (m, 1H), 1.28-1.15 (m, 1H), 0.95 (s, 3H), 0.93 (s, 3H).

MS (ESI) m/z 405 (M+H)$^+$.

IR (KBr) ν$_{max}$ 1732, 1639, 1387, 1184 cm$^{-1}$

[α]$_D^{27}$ +24.0° (c 0.275, methanol).

Step 2. N-{(1S,2S)-[(Dimethylamino)carbonyl]-2-methylbutyl}-3-(2-morpholin-4-ylethyl)-2-oxo-2,3-dihydro-1H-benzimidazole-1-carboxamide To a solution of N-{[3-(2-morpholin-4-ylethyl)-2-oxo-2,3-dihydro-1H-benzimidazol-1-yl]carbonyl}-L-isoleucine hydrochloride (Step 1, 62 mg, 0.14 mmol) in DMF (1 mL) was added CDI (27 mg, 0.17 mol) at rt. After 2 h, to the mixture was added aq. dimethylamine (40%, 20 μL) and stirred for further 14 h. Then to the mixture was added water (10 mL). The mixture was extracted with ethyl acetate (20 mL×2) and the combined organic layers were washed with brine (10 mL), dried over sodium sulfate, filtered and concentrated. The residue was purified by preparative TLC eluting with dichloromethane/methanol (10/1) to afford 33 mg (54%) of the title compound.

$^1$H-NMR (300 MHz, DMSO-d$_6$) δ 9.14 (d, J=8.4 Hz, 1H), 8.02 (d, J=7.5 Hz, 1H), 7.35 (d, J=7.8 Hz, 1H), 7.24 (t, J=7.2 Hz, 1H), 7.15 (t, J=7.8 Hz, 1H), 4.83 (dd, J=8.4, 6.3 Hz, 1H), 4.02 (t, J=6.0 Hz, 2H), 3.49 (t, J=4.8 Hz, 4H), 3.12 (s, 3H), 2.87 (s, 3H), 2.63-2.58 (m, 2H), 2.46-2.43 (m, 4H), 1.85-1.75 (m, 1H), 1.57-1.48 (m, 1H), 1.17-1.07 (m, 1H), 0.93 (d, J=6.6 Hz, 3H), 0.87 (t, J=7.5 Hz, 3H).

MS (ESI) m/z 432 (M+H)$^+$.

Example 4

N-[(1S)-1-(Aminocarbonyl)2,2-dimethylpropyl]-3-(2-morpholin-4-ylethyl)-2-oxo-2,3-dihydro-1H-benzimidazole-1-carboxamide

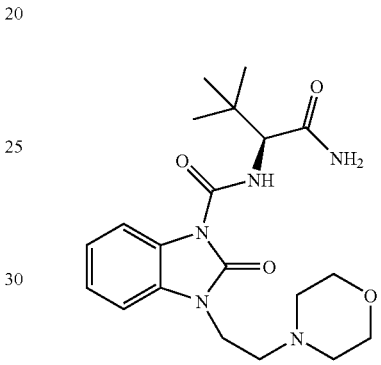

Step 1. Benzyl [(1S)-1-(aminocarbonyl)-2,2-dimethylpropyl]carbamate

To a solution of N-[(benzyloxy)carbonyl]-tert-leucine (prepared according to the procedure in the literature; Emily, M. S. et al. *Tetrahedron* 2001, 57, 5303-5320.; 3.7 g, 14 mmol) in DMF (80 mL) were added ammonium chloride (900 mg, 17 mmol), triethylamine (5.9 mL, 42 mmol), HOBt (2.8 g, 18 mmol) and EDAPC (3.1 g, 18 mmol) and stirred at rt. After 17 h, the reaction mixture was quenched by addition of saturated aqueous sodium bicarbonate (100 mL) and extracted with ethyl acetate (100 mL×3). The combined organic layers were washed with water (100 mL×3), brine (50 mL), dried over sodium sulfate, filtered and concentrated in vacuo. The residue was purified by column chromatography on silica gel eluting with hexane/ethyl acetate (2/1-1/1) to afford 3.0 g (82%) of the title compound.

MS (ESI) m/z 265 (M+H)$^+$.

Step 2. tert-Leucinamide

To a solution of benzyl [(1S)-1-(aminocarbonyl)-2,2-dimethylpropyl]carbamate (Step 1, 3.7 g, 14 mmol) in THF (40 mL) was added 10% Pd/C (710 mg). The flask was evacuated and flushed with H$_2$ gas and this process was repeated three times. The flask was filled with H$_2$ gas (4 atm) and stirred for 3 h at rt. Then the reaction mixture was filtered through a pad of Celite and concentrated in vacuo to give the title compound as white solid (crude; 1.8 g)

$^1$H-NMR (300 MHz, DMSO-d$_6$) δ 6.59 (bs, 1H), 5.92 (bs, 1H), 3.12 (s, 1H), 1.02 (s, 1H).

MS (ESI) m/z 131 (M+H)$^+$.

Step 3. N-[(1S)-1-(Aminocarbonyl)-2,2-dimethyl-propyl]-3-(2-morpholin-4-ylethyl)-2-oxo-2,3-dihydro-1H-benzimidazole-1-carboxamide hydrochloride The title compound was prepared according to the procedure described in Step 4 of Example 1 from L-tert-leucinamide.

$^1$H-NMR (270 MHz, CDCl$_3$, the value of free form of the title compound) δ 9.45 (d, J=7.8 Hz, 1H), 8.19-8.16 (m, 1H), 7.25-7.14 (m, 2H), 7.05 (d, J=7.6 Hz, 1H), 5.83 (bs, 1H), 5.53 (bs, 1H), 4.22 (d, J=8.1 Hz, 1H), 4.02 (t, J=6.8 Hz, 2H), 3.68 (t, J=4.6 Hz, 4H), 2.73-2.68 (m, 2H), 2.60-2.49 (m, 4H), 1.15 (s, 9H).

MS (ESI) m/z 404 (M+H)$^+$.

Anal. calcd. for C$_{20}$H$_{29}$N$_5$O$_4$ (+1.0H$_2$O, 1.0HCl): C, 52.45; H, 7.043; N, 15.29; O, 17.47; Cl, 7.74. Found: C, 52.41; H, 7.21; N, 14.98.

[α]$_D^{25}$ +29.5° (c 0.325, methanol).

Example 5

Methyl 3-methyl-N-{[3-(2-morpholin-4-ylethyl)-2-oxo-2,3-dihydro-1H-benzimidazol-1-yl]carbonyl}-L-valinate

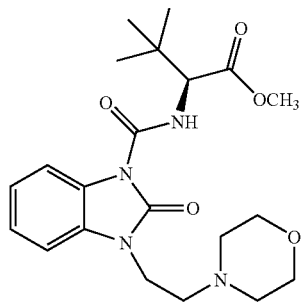

The title compound was prepared according to the procedure described in Step 4 of Example 1 from methyl L-tert-leucinate. The obtained compound was further purified by recrystallization from hexane/ethyl acetate.

$^1$H-NMR (300 MHz, CDCl$_3$) δ 9.40 (d, J=8.4 Hz, 1H), 8.20-8.17 (m, 1H), 7.25-7.08 (m, 3H), 4.44 (d, J=8.4 Hz, 1H), 4.10-3.99 (m, 2H), 3.77 (s, 3H), 3.73-3.65 (m, 4H), 2.77-2.66 (m, 2H), 2.62-2.52 (m, 4H), 1.09 (s, 9H).

MS (ESI) m/z 419 (M+H)$^+$.

Anal. calcd. for C$_{21}$H$_{30}$N$_4$O$_5$ (+0.5H$_2$O): C, 59.00; H, 7.31; N, 13.11; O, 20.58. Found: C, 59.24; H, 7.23; N, 13.15.

IR (KBr) ν$_{max}$ 1728, 1553, 1398, 1159 cm$^1$.

Example 6

N-{(1S)-2,2-Dimethyl-[(methylamino)carbonyl]propyl-3-(2-morpholin-4-ylethyl)-2-oxo-2,3-dihydro-1H-benzimidazole-1-carboxamide

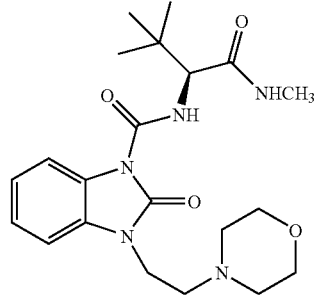

The title compound was prepared according to the procedure described in Example 3 from Methyl 3-methyl-N-{[3-(2-morpholin-4-ylethyl)-2-oxo-2,3-dihydro-1H-benzimidazol-1-yl]carbonyl}-L-valinate (Example 5) and aqueous methylamine (40%).

$^1$H-NMR (270 MHz, CDCl$_3$) δ 9.43 (d, J=8.4 Hz, 1H), 8.18-8.15 (m, 1H), 7.25-7.07 (m, 3H), 5.85-5.75 (bs, 1H), 4.15 (d, J=8.4 Hz, 1H), 4.10-3.95 (m, 2H), 3.75-3.62 (m, 4H), 2.84 (d, J=4.59 Hz, 3H), 2.78-2.45 (m, 6H), 1.12 (s, 9H).

MS (ESI) m/z 418 (M+H)$^+$.

Example 7

N-{(1S)-1-[(Dimethylamino)carbonyl]-2,2-dimethyl-propyl}-3-(2-morpholin-4-ylethyl)-2-oxo-2,3-dihydro-1H-benzimidazole-1-carboxamide

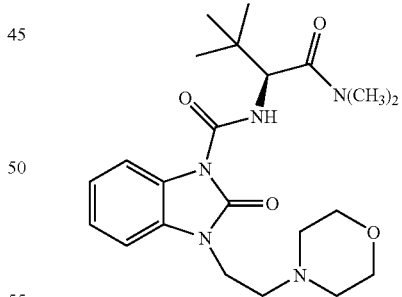

The title compound was prepared according to the procedure described in Example 3 from Methyl-3-methyl-N-{[3-(2-morpholin-4-ylethyl)-2-oxo-2,3-dihydro-1H-benzimidazol-1-yl]carbonyl}-L-valinate (Example 5).

$^1$H-NMR (270 MHz, CDCl$_3$) δ 9.48 (d, J=9.2 Hz, 1H), 8.18-8.15 (m, 1H), 7.23-7.12 (m, 2H), 7.03 (d, J=7.6 Hz, 1H), 4.93 (d, J=9.2 Hz, 1H), 4.05-3.99 (m, 2H), 3.69-3.66 (m, 4H), 3.23 (s, 3H), 3.00 (s, 3H), 2.74-2.66 (m, 2H), 2.58-2.48 (m, 4H), 1.11 (s, 9H)

MS (ESI) m/z 432 (M+H)$^+$.

Example 8

N-[(1S,2S)-1-(Aminocarbonyl)-2-methylbutyl]-2-oxo-3-(2-piperidin-1-ylethyl)-2,3-dihydro-1H-benzimidazole-1-carboxamide hydrochloride

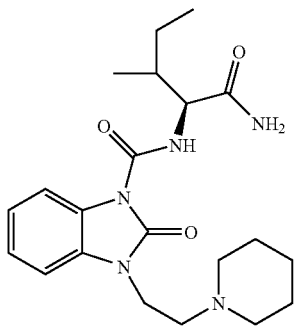

Step 1. 1-(2-Piperidin-1-ylethyl)-1,3-dihydro-2H-benzimidazol-2-one

The title compound was prepared according to the procedure described in Steps 1 to 3 of Example 1 from 1-(2-aminoethyl)piperidine.

$^1$H-NMR (300 MHz, CDCl$_3$) δ 10.82-10.72 (m, 1H), 7.07-7.04 (m, 4H), 4.06-4.01 (m, 2H), 2.71-2.65 (m, 2H), 2.55-2.50 (m, 4H), 1.62-1.58 (m, 4H), 1.45-1.43 (m, 2H).

MS (ESI) m/z 246 (M+H)$^+$.

Step 2. N-[(1S,2S)-1-(Aminocarbonyl)-2-methylbutyl]-2-oxo-3-(2-piperidin-1-ylethyl)-2,3-dihydro-1H-benzimidazole-1-carboxamide hydrochloride The title compound was prepared according to the procedure described in Steps 4 of Example 1 from 1-(2-Piperidin-1-ylethyl)-1,3-dihydro-2H-benzimidazol-2-one (Step 1).

$^1$H-NMR (270 MHz, CDCl$_3$) δ 12.47 (bs, 1H), 9.06 (d, J=8.1 Hz, 1H), 8.10 (d, J=7.6 Hz, 1H), 7.53 (d, J=7.6 Hz, 1H), 7.24-7.11 (m, 2H), 6.48 (bs, 1H), 5.69 (bs, 1H), 4.55-4.53 (m, 2H), 4.42 (dd, J=8.1, 5.4 Hz, 1H), 3.80-3.50 (m, 2H), 3.40-3.10 (m, 2H), 2.86-2.65 (m, 2H), 2.26-1.48 (m, 7H), 1.34-1.17 (m, 2H), 1.05 (d, J=7.0 Hz, 3H), 0.97 (t, J=7.3 Hz, 3H).

MS (ESI) m/z 402.4 (M+H)$^+$.

Anal. calcd. for C$_{21}$H$_{31}$N$_5$O$_3$ (+0.5H$_2$O, 1HCl, 0.2 C$_4$H$_8$O$_2$): C, 56.36; H, 7.51; N, 15.07; O, 13.43; Cl, 7.63. Found: C, 56.28; H, 7.72; N, 14.96.

mp 217.1° C.

Example 9

N-[(1S,2S)-1-methylbutyl]-4-methoxy-3-(2-morpholin-4-ylethyl)-2-oxo-2,3-dihydro-1H-benzimidazole-1-carboxamide hydrochloride

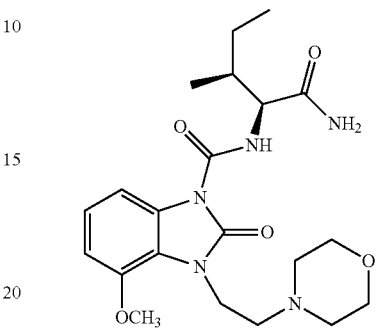

Step 1. 2-Bromo-N-(2-methoxy-6-nitrophenyl)acetamide

To a flask was added sodium hydride (60% dispersion in mineral oil, 610 mg, 15 mmol) and hexane (2 mL) at 0° C. The supernatant liquid was decanted and the residue was dried under reduced pressure. To this was added THF (20 mL) and a solution of 2-methoxy-6-nitroaniline (2 g, 12 mmol, Kubo, K. et al. *J. Med. Chem.* 1993, 36, 1772-1784) in THF (20 mL) at 0° C. and stirred at rt for 2 h. To this mixture was added bromoacetyl bromide (1.2 mL, 14 mmol) at 0° C. and stirred at rt for 3 h. Then the reaction mixture was quenched by addition of water (100 mL) and extracted with ethyl acetate (100 mL×2). The combined organic layers were washed with brine (100 mL), dried over sodium sulfate, filtered and concentrated in vacuo. The residue was purified by column chromatography on silica gel eluting with hexane/ethyl acetate (2/1-1/1) to afford 2.9 g (85%) of the title compound.

$^1$H-NMR (300 MHz, CDCl$_3$) δ 8.62 (bs, 1H), 7.56 (dd, J=8.2, 1.1 Hz, 1H), 7.34 (dd, J=8.4, 8.2 Hz, 1H), 7.19 (dd, J=8.4, 1.1 Hz, 1H), 4.04 (s, 2H), 3.96 (s, 3H).

Step 2. N-(2-Methoxy-6-nitrophenyl)-2-morpholin-4-ylacetamide

To a solution of 2-bromo-N-(2-methoxy-6-nitrophenyl)acetamide (Step 1, 8.8 g, 30 mmol) in THF (240 mL) was added morpholin (11 mL, 122 mmol) at 0° C. and warmed to rt. After 2.5 h, the reaction mixture was quenched by addition of water (200 mL) and extracted with ethyl acetate (200 mL×2). The combined organic layers were washed with water (200 mL), brine (100 mL) dried over sodium sulfate, filtered and concentrated in vacuo. The residue was purified by column chromatography on silica gel eluting with hexane/ethyl acetate (2/1) to afford 6.7 g (75%) of the title compound.

$^1$H-NMR (270 MHz, CDCl$_3$) δ 9.51 (bs, 1H), 7.53 (dd, J=8.4, 8.1 Hz, 1H), 7.29 (dd, J=8.4, 8.1 Hz, 1H), 7.17 (dd, J=8.4, 1.1 Hz, 1H), 3.94 (s, 3H), 3.84-3.81 (m, 4H), 3.18 (s, 2H), 2.68-2.65 (m, 4H).

MS (ESI) m/z 296 (M+H)$^+$, 294 (M−H)$^−$.

Step 3. 3-Methoxy-N²-(2-morpholin-4-ylethyl)benzene-1,2-diamine

To a suspension of lithium aluminum hydride (5.2 g, 136 mmol) in THF (35 mL) was added a solution of N-(2-methoxy-6-nitrophenyl)-2-morpholin-4-ylacetamide (Step 2, 6.7 g, 23 mmol) in THF (40 mL) at 0° C. and stirred at reflux for 2 h. Then to this mixture was added water (5.2 mL) followed by addition of 15% sodium hydroxide (5.2 mL), water (15.6 mL) at 0° C. The mixture was diluted with ethyl acetate (100 mL) and stirred for 3 h at rt. The resultant mixture was filtered and concentrated in vacuo. The residue was purified by column chromatography on silica gel eluting with dichloromethane/methanol (30/1) to afford 2.5 g (44%) of the title compound.
¹H-NMR (300 MHz, CDCl₃) δ 6.82 (t, J=8.1 Hz, 1H), 6.39-6.31 (m, 2H), 3.79 (s, 3H), 3.77-3.69 (m, 4H), 3.02-2.98 (m, 2H), 2.53-2.50 (m, 6H).
MS (ESI) m/z 252 (M+H)⁺.

Step 4. 7-Methoxy-1-(2-morpholin-4-ylethyl)-1,3-dihydro-2-H-benzimidazol-2-one

The title compound was prepared according to the procedure described in Step 3 of Example 1 from 3-Methoxy-N²-(2-morpholin-4-ylethyl)benzene-1,2-diamine (Step 3).
¹H-NMR (300 MHz, CDCl₃) δ 8.98 (bs, 1H), 6.98 (dd, J=8.3, 7.9 Hz, 1H), 6.72 (dd, J=7.9, 0.7 Hz, 1H), 6.63 (d, J=8.2 Hz, 1H), 4.21 (t, J=7.1 Hz, 2H), 3.90 (s, 3H), 3.71-3.68 (m, 4H), 2.71 (t, J=7.1 Hz, 2H), 2.58-2.55 (m, 4H).
MS (ESI) m/z 278 (M+H)⁺.

Step 5. N-[(1S,2S)-1-(Aminocarbonyl)-2-methylbutyl]-4-methoxy-3-(2-morpholin-4-ylethyl)-2-oxo-2,3-dihydro-1H-benzimidazole-1-carboxamide hydrochloride The title compound was prepared according to the procedure described in Step 4 of Example 1 from 7-Methoxy-1-(2-morpholin-4-ylethyl)-1,3-dihydro-2-H-benzimidazol-2-one (Step 4) and L-isoleucinamide.
¹H-NMR (300 MHz, CDCl₃) δ 12.70 (bs, 1H), 9.12 (d, J=8.1 Hz, 1H), 7.84 (d, J=8.4 Hz, 1H), 7.19 (bs, 1H), 7.09 (t, J=8.4 Hz, 1H), 6.74 (d, J=8.4 Hz, 1H), 5.69 (bs, 1H), 4.69-4.55 (m, 2H), 4.44 (dd, J=8.4, 4.5 Hz, 4H), 4.37-4.03 (m, 5H), 3.94 (s, 3H), 3.60-3.40 (m, 2H), 3.30-3.15 (m, 1H), 3.10-2.40 (m, 2H), 2.27-2.16 (m, 1H), 1.67-1.54 (m, 1H), 1.36-1.16 (m, 1H), 1.06 (d, J=6.9 Hz, 3H), 0.97 (t, J=7.5 Hz, 3H).
MS (ESI) m/z 434 (M+H)⁺.
Anal. calcd. for C₂₁H₃₁N₅O₅ (+0.5H₂O, 1HCl, 0.1 C₄H₈O₂): C, 52.69; H, 6.98; N, 14.36; O, 18.70, Cl, 7.27. Found: C, 52.33; H, 7.20; N, 14.01.

Example 10

N-[(1S)-1-(Aminocarbonyl)-2,2-dimethylpropyl]-2-oxo-3-[2-(tetrahydro-2H-pyran-4-yl)ethyl]-2,3-dihydro-1H-benzimidazole-1-carboxamide

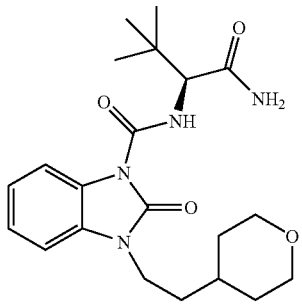

Step 1. 1-[2-(Tetrahydro-2H-pyran)-4-ylethyl]-1,3-dihydro-2H-benzimidazol-2-one

The title compound was prepared according to the procedure described in Steps 1 to 3 of Example 1 from 2-(tetrahydro-2H-pyran-4-yl)ethanamine.
MS (ESI) m/z 247 (M+H)⁺, 245 (M–H)⁻.

Step 2. N-[(1S)-1-(Aminocarbonyl)-2,2-dimethylpropyl]-2-oxo-3-[2-(tetrahydro-2H-pyran-4-yl)ethyl]-2,3-dihydro-1H-benzimidazole-1-carboxamide The title compound was prepared according to the procedure described in Step 4 of Example 1 from 1-(2-(Tetrahydro-2H-pyran-4-ylethyl)-1,3-dihydro-2H-benzimidazol-2-one (Step 1).
¹H-NMR (270 MHz, CDCl₃) δ 9.45 (d, J=8.1 Hz, 1H), 8.17 (d, J=7.56 Hz, 1H), 7.25-7.14 (m, 2H), 7.00 (dd, J=8.1, 1.6 Hz, 1H), 5.99 (bs, 1H), 5.23 (bs, 1H), 4.24 (d, J=8.1 Hz, 1H), 4.00-3.88 (m, 4H), 3.38 (t, J=11.6 Hz, 2H), 1.77-1.69 (m, 4H), 1.64-1.53 (m, 1H), 1.45-1.30 (m, 2H), 1.15 (s, 9H).
MS (ESI) m/z 403 (M+H)⁺.
Anal. calcd. for C₂₁H₃₀N₄O₄ (+0.1H₂O): C, 62.39; H, 7.53; N, 13.86; O, 16.23. Found: C, 62.21; H, 7.59; N, 13.70.

Example 11

N-[(1S)-(Aminocarbonyl)-2,2-dimethylpropyl]-3-(cyclopropylmethyl)-2-oxo-2,3-dihydro-1H-benzimidazole-1-carboxamide

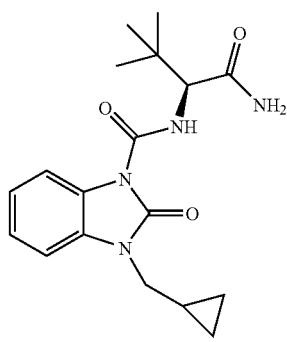

Step 1. 1-(cyclopropylmethyl)-1,3-dihydro-2H-benzimidazol-2-one

The title compound was prepared according to the procedure described in Steps 1 to 3 of Example 1 from 1-cyclopropylmethanamine.
¹H-NMR (300 MHz, CDCl₃) δ 7.15-7.03 (m, 4H), 3.79 (d, J=7.0 Hz, 2H), 1.30-1.21 (m, 1H), 0.59-0.50 (m, 2H), 0.48-0.39 (m, 2H).
MS (ESI) m/z 189 (M+H)⁺.

Step 2. N-[(1S)-1-(Aminocarbonyl)-2,2-dimethylpropyl]-3-(cyclopropylmethyl)-2-oxo-2,3-dihydro-1H-benzimidazole-1-carboxamide The title compound was prepared according to the procedure described in step 4 of Example 1 from 1-(cyclopropylmethyl)-1,3-dihydro-2H-benzimidazol-2-one (Step 1).

$^1$H-NMR (270 MHz, CDCl$_3$) δ 9.48 (d, J=7.8 Hz, 1H), 8.17 (d, J=7.83 Hz, 1H), 7.25-7.13 (m, 2H), 7.10-7.06 (m, 1H), 5.96 (bs, 1H), 5.65 (bs, 1H), 4.23 (d, J=7.8 Hz, 1H), 3.79 (d, J=7.02 Hz, 2H), 1.33-1.21 (m, 1H), 1.15 (s, 9H), 0.62-0.55 (m, 2H), 0.50-0.42 (m, 2H).

MS (ESI) m/z 345 (M+H)$^+$.

Anal. calcd. for $C_{18}H_{24}N_3O_3$ (+0.1H$_2$O): C, 62.45; H, 7.05; N, 16.18; O, 14.33. Found: C, 62.26; H, 7.06; N, 16.08.

Example 12

N-[(1S)-8-(Aminocarbonyl)-2,2-dimethylpropyl]-3-(3-methylbutyl)-2-oxo-2,3-dihydro-1H-benzimidazole-1-carboxamide

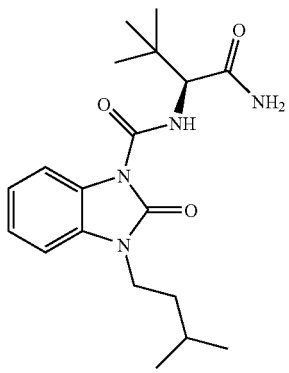

Step 1.
1-(3-methylbutyl)1,3-dihydro-2H-benzimidazol-2-one

The title compound was prepared according to the procedure described in the literature (Meth-Cohn, O.; Smith, D. I. J.C.S. Perkin Trans. 1, 1982, 261-270.; Vernin G. et al. J. Heterocyclic Chem. 1981, 18, 85-89.) from 1-bromo-3-methylbutane.

$^1$H-NMR (300 MHz, CDCl$_3$) δ9.86 (br, 1H), 7.14-6.98 (m, 4H), 3.94-3.88 (m, 2H), 1.72-1.62 (m, 3H), 1.00 (d, J=6.1 Hz, 6H).

Step 2 N-[(1S)-1-(Aminocarbonyl)-2,2-dimethylpropyl]-3-(3-methylbutyl)-2-oxo-2,3-dihydro-1H-benzimidazole-1-carboxamide To a solution of 1-(3-methylbutyl)1,2-dihydro-2H-benzimidazol-2-one (Step 1, 140 mg, 0.69 mmol) in dichloromethane (2.5 mL) were added triethylamine (0.32 mL, 2.3 mmol) and 4-nitrophenyl chloroformate (150 mg, 0.76 mmol) at 0° C. and the mixture was stirred for 4 h at rt. Then to this mixture was added a solution of L-tert-leucinamide (steps 1 and 2 in example 4, 99 mg, 0.76 mmol) in dichloromethane (2 mL) at 0° C. and stirred rt. After 22 h, the reaction was quenched by addition of water (20 mL) and extracted with ethyl acetate (30 mL×2). The combined organic layers were washed with water (20 mL×3), brine (20 mL) and dried over sodium sulfate, filtered and concentrated. The residue was purified by column chromatography on silica gel eluting with hexane/ethyl acetate (3/1-1/1) to afford 240 mg (96%) of the titled compound. The obtained product was further purified by recrystallization from hexane/ethyl acetate to give 220 mg of the title compound.

$^1$H-NMR (270 MHz, CDCl$_3$) δ 9.48 (d, J=7.8 Hz, 1H), 8.16 (d, J=7.56 Hz, 1H), 7.25-7.12 (m, 2H), 7.03-7.00 (m, 1H), 6.01 (bs, 1H), 5.72 (bs, 1H), 4.24 (d, J=7.8 Hz, 1H), 3.99-3.81 (m, 2H), 1.71-1.61 (m, 3H), 1.15 (s, 9H), 1.00 (d, J=6.2 Hz, 6H).

MS (ESI) m/z 361 (M+H)$^+$.

Anal. calcd. for $C_{19}H_{28}N_4O_3$: C, 63.31; H, 7.83; N, 15.54; O, 13.32. Found: C, 62.94; H, 7.86; N, 15.62.

Example 13

N-[(1S)-1-(Aminocarbonyl)-2,2-dimethylpropyl]-3-(3,3-dimethylbutyl)-2-oxo-2,3-dihydro-1H-benzimidazole-1-carboxamide

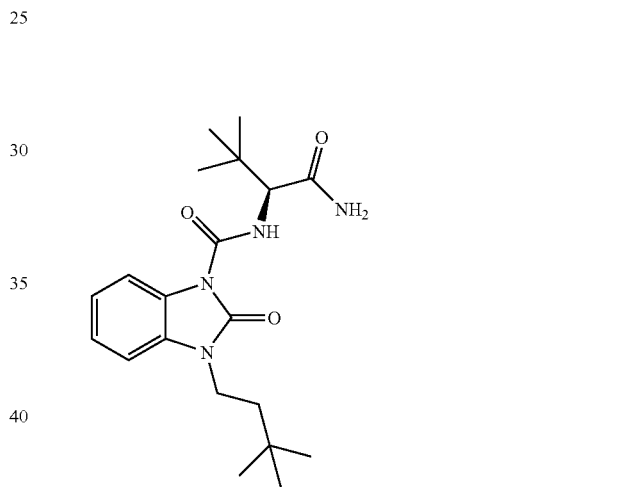

Step 1. 1-(3,3-dimethylbutyl)1,2-dihydro-2H-benzimidazol-2-one

The title compound was prepared according to the procedure described in the literature (Meth-Cohn, O.; Smith, D. I. J.C.S. Perkin Trans. 1, 1982, 261-270.; Vernin G. et al. J. Heterocyclic Chem. 1981, 18, 85-89.) from 1-bromo-3,3-dimethylbutane.

$^1$H-NMR (300 MHz, CDCl$_3$) δ9.7-9.5 (br, 1H), 7.14-6.96 (m, 4H), 3.94-3.88 (m, 2H), 1.71-1.63 (m, 2H), 1.04 (s, 9H).

Step 2. N-[(1S)-1-(Aminocarbonyl)-2 2-dimethylpropyl]-3-(3,3-dimethylbutyl)-2-oxo-2,3-dihydro-1H-benzimidazole-1-carboxamide The title compound was prepared according to the procedure described in Step 2 of Example 12 from 1-(3-methylbutyl)1,2-dihydro-2H-benzimidazol-2-one (Step 1).

$^1$H-NMR (270 MHz, CDCl$_3$) δ 9.47 (d, J=8.1 Hz, 1H), 8.16 (dd, J=7.8, 1.4 Hz, 1H), 7.27-7.12 (m, 2H), 6.99 (dd, J=7.3, 1.6 Hz, 1H), 6.01 (bs, 1H), 5.74 (bs, 1H), 4.25 (d, J=8.1 Hz, 1H), 3.99-3.81 (m, 2H), 1.70-1.62 (m, 2H), 1.15 (s, 9H), 1.04 (s, 9H).

MS (ESI) m/z 375 (M+H)$^+$.

Anal. calcd. for $C_{20}H_{30}N_4O_3$ (+0.1H$_2$O): C, 63.84; H, 8.09; N, 14.89; O, 13.18. Found: C, 63.47; H, 8.10; N, 14.89.

Example 14

N-[(1S)-1-(Aminocarbonyl)-2,2-dimethylpropyl]-3-[(1-methylpiperidin-2-yl)methyl]-2-oxo-2,3-dihydro-1H-benzimidazole-1-carboxamide hydrochloride

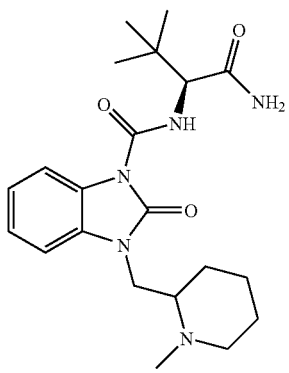

Step 1. 1-[(1-methylpiperidin-2-yl)methyl]-1,3-dihydro-2H-benzimidazol-2-one

The title compound was prepared according to the procedure described in Steps 1 to 3 of Example 1 from 1-(1-methylpiperidin-2-yl)methanamine.

MS (ESI) m/z 246 (M+H)$^+$.

Step 2. N-[(1S)-1-(Aminocarbonyl)-2,2-dimethylpropyl]-3-[(1-methylpiperidin-2-yl)methyl]-2-oxo-2,3-dihydro-1H-benzimidazole-1-carboxamide hydrochloride The title compound was prepared according to the procedure described in Step 4 of Example 1 from 1-[(1-methylpiperidin-2-yl)methyl]-1,3-dihydro-2H-benzimidazol-2-one.

$^1$H-NMR (300 MHz, CDCl$_3$) δ 9.26-9.21 (m, 2H), 8.11 (d, J=8.4 Hz, 2H), 7.41-7.14 (m, 6H), 6.13-5.95 (m, 2H), 5.61-5.56 (m, 2H), 4.71-4.52 (m, 4H), 4.26 (d, J=8.4 Hz, 2H), 3.30-3.28 (m, 4H), 2.96 (s, 3H), 2.91 (s, 3H), 2.18-1.80 (m, 14H), 1.14 (s, 18H).

MS (ESI) m/z 402 (M+H)$^+$.

Anal. calcd. for $C_{21}H_{31}N_5O_3$ (+0.8H$_2$O, 1.5HCl): C, 53.60; H, 7.30; N, 14.88; O, 12.92; Cl, 11.30. Found: C, 53.99; H, 7.61; N, 14.86.

Example 15

N-[(1S)-1-(Aminocarbonyl)-2,2-dimethylpropyl]-4-methyl-3-(2-morpholin-4-ylethyl)-2-oxo-2,3-dihydro-1H-benzimidazole-1-carboxamide

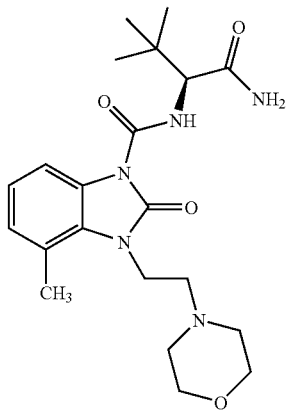

Step 1.
2-Methyl-N-(2-morpholin-4-ylethyl)-6-nitroaniline

A solution of 2-chloro-3-nitrotoluene (180 mg, 1.0 mmol), 4-(2-aminoethyl)morpholine (0.54 mL, 4.1 mmol) and triethylamine (0.43 mL, 3.1 mmol) was heated to 180° C. by microwave for 20 min. The resultant mixture was purified by column chromatography on silica gel eluting with hexane/ethyl acetate(8/1-3/1) to afford 160 mg (59%) of the title compound.

MS (ESI) m/z 266 (M+H)$^+$.

Step 2. 7-Methyl-1-(2-morpholin-4-ylethyl)-1,3-dihydro-2H-benzimidazol-2-one

The title compound was prepared according to the procedure described in Steps 2 to 3 of Example 1 from 2-Methyl-N-(2-morpholin-4-ylethyl)-6-nitroaniline (Step 1).

$^1$H-NMR (300 MHz, CDCl$_3$) δ 9.10 (bs, 1H), 6.98-6.91 (m, 2H), 6.85-6.82 (m, 1H), 4.24-4.19 (m, 2H), 3.72-3.69 (m, 4H), 2.70-2.65 (m, 2H), 2.60 (s, 3H), 2.58-2.55 (m, 4H).

MS (ESI) m/z 262 (M+H)$^+$.

Step 3. N-[(1S)-1-(Aminocarbonyl)-2,2-dimethylpropyl]-4-methyl-3-(2-morpholin-4-ylethyl)-2-oxo-2,3-dihydro-1H-benzimidazole-1-carboxamide The title compound was prepared according to the procedure described in Step 4 of example 1 from 7-methyl-1-(2-morpholin-4-ylethyl)-1,3-dihydro-2H-benzimidazol-2-one (Step 2).

$^1$H-NMR (300 MHz, CDCl$_3$) δ 9.58 (d, J=7.8 Hz, 1H), 8.10 (d, J=7.8 Hz, 1H), 7.05 (t, J=7.8 Hz, 1H), 6.96 (d, J=7.8 Hz, 1H), 5.91 (bs, 1H), 5.60 (bs, 1H), 4.29-4.18 (m, 3H), 3.73-3.65 (m, 4H), 2.75-2.64 (m, 2H), 2.60 (s, 3H), 2.63-2.45 (m, 4H), 1.15 (s, 9H).

MS (ESI) m/z 418 (M+H)$^+$.

47

Anal. calcd. for $C_{21}H_{31}N_5O_4$ (+0.5$H_2O$, 0.1 $C_4H_8O_2$): C, 59.04; H, 7.59; N, 16.09; O, 17.27. Found: C, 58.99; H, 7.35; N, 15.88.

Example 16

N-[(1S)-1-(Aminocarbonyl)-2,2-dimethylpropyl]-5-methyl-3-(2-morpholin-4-ylethyl)-2-oxo-2,3-dihydro-1H-benzimidazole-1-carboxamide hydrochloride

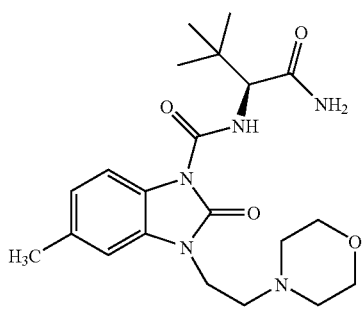

Step 1. 6-methyl-1-(2-morpholin-4-ylethyl)-1,3-dihydro-2H-benzimidazol-2-one The title compound was prepared according to the procedure described in Steps 1 to 3 of Example 1 from 3-fluoro-4-nitrotoluene.

MS (ESI) m/z 262 (M+H)$^+$, 260 (M–H)$^-$.

Step 2. N-[(1S)-1-(Aminocarbonyl)-2,2-dimethylpropyl]-5-methyl-3-(2-morpholin-4-ylethyl)-2-oxo-2,3-dihydro-1H-benzimidazole-1-carboxamide hydrochloride The title compound was prepared according to the procedure described in Step 4 of Example 1 from 6-methyl-1-(2-morpholin-4-ylethyl)-1,3-dihydro-2H-benzimidazol-2-one (Step 1).

$^1$H-NMR (300 MHz, DMSO-d$_6$) δ 11.47 (bs, 1H), 9.09 (d, J=9.0 Hz, 1H), 7.90 (d, J=7.5 Hz, 1H), 7.70 (s, 1H), 7.37 (s, 1H), 7.22 (s, 1H), 7.00 (d, J=7.5 Hz, 1H), 4.43-4.32 (m, 2H), 4.25 (d, J=9.0 Hz, 1H), 4.07-3.95 (m, 2H), 3.88-3.72 (m, 2H), 3.68-3.52 (m, 2H), 3.51-3.42 (m, 2H), 3.27-3.10 (m, 2H), 2.38 (s, 3H), 1.00 (s, 9H).

MS (ESI) m/z 418 (M+H)$^+$.

Anal. calcd. for $C_{21}H_{31}N_5O_4$ (+1.0$H_2O$, 1.0HCl): C, 53.44; H, 7.26; N, 14.84; O, 16.95; Cl, 7.51. Found: C, 53.77; H, 7.32; N, 14.64.

Example 17

N-[(1S)-1-(Aminocarbonyl)-2,2-dimethylpropyl]-3-(3-methylbutyl)-2-oxo-2,3-dihydro-1H-imidazo[4,5-c]pyridine-1-carboxamide

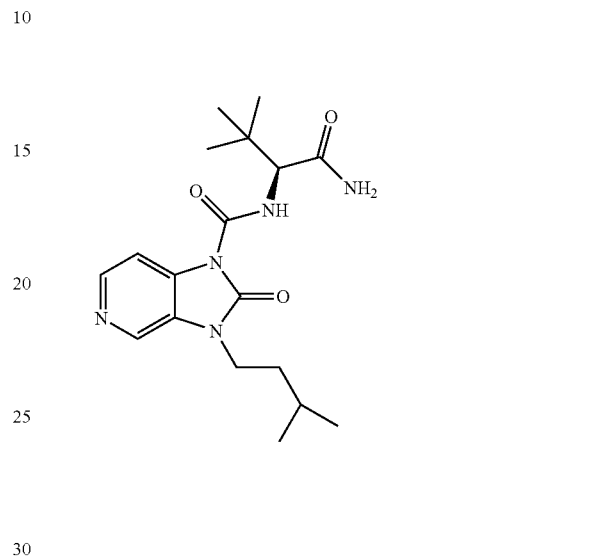

Step 1. 3-(3-methylbutyl)-1,3-dihydro-2H-imidazo[4,5-c]pyridine-2-one

The title compound was prepared according to the procedure described in the literature (Meth-Cohn, O.; Smith, D. I. J.C.S. Perkin Trans. 1, 1982, 261-270.; Vernin G. et al. J. Heterocyclic Chem. 1981, 18, 85-89.) from 1-bromo-3-methylbutane and 1-isopropenyl-1,3-dihydro-2H-imidazo[4,5-c]pyridin-2-one (Israel, M.; Jones, L. C. J. Heterocyclic Chem. 1971, 8, 797.

$^1$H-NMR (300 MHz, CDCl$_3$) δ 10.15 (br, 1H), 8.33 (d, J=5.3 Hz, 1H), 8.33 (s, 1H), 7.09 (d, J=5.3 Hz, 1H), 3.95 (t, J=7.3. Hz, 2H), 1.76-1.63 (m, 3H), 1.02 (d, J=7.0 Hz, 6H).

Step 2. N-[(1S)-(Aminocarbonyl)-2,2-dimethylpropyl]-3-(3-methylbutyl)-2-oxo-2,3-dihydro-1H-imidazo[4,5-c]pyridine-1-carboxamide The title compound was prepared according to the procedure described in Step 4 of Example 1 from 3-(3-methylbutyl)-1,3-dihydro-2H-imidazo[4,5-c]pyridin-2-one.

$^1$H-NMR (300 MHz, CDCl$_3$) δ 9.34 (d, J=8.1 Hz, 1H), 8.43 (d, J=5.1 Hz, 1H), 8.38 (s, 1H), 8.04 (d, J=5.1 Hz, 1H), 5.80 (bs, 1H), 5.59 (bs, 1H), 4.20 (d, J=8.1. Hz, 1H), 4.00-3.90 (m, 2H), 1.76-1.65 (m, 3H), 1.15 (s, 9H), 1.02 (d, J=5.7 Hz, 6H).

MS (ESI) m/z 362 (M+H)$^+$

Anal. calcd. for $C_{18}H_{27}N_5O_3$ (+0.5$H_2O$): C, 58.36; H, 7.62; N, 18.91; O, 15.12. Found: C, 58.60; H, 7.45; N, 18.94.

Example 18

N-[(1S)-1-(Aminocarbonyl)-2,2-dimethylpropyl]-3-[2-(dimethylamino)ethyl]-4-methyl-2-oxo-2,3-dihydro-1H-benzimidazole-1-carboxamide

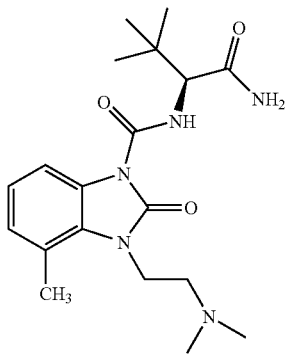

Step 1. 1-[2-(dimethylamino)ethyl]-7-methyl-1,3-dihydro-2H-benzimidazol-2-one The title compound was prepared according to the procedure described in Steps 1 to 3 of Example 1 from N,N-dimethylethylenediamine and 2-chloro-3-nitrotoluene.
MS (ESI) m/z 220 (M+H)+.

Step 2. N-[(1S)-1-(Aminocarbonyl)-2,2-dimethylpropyl]-3-[2-(dimethylamino)ethyl]-1'-4-methyl-2-oxo-2,3-dihydro-1H-benzimidazole-1-carboxamide The title compound was prepared according to the procedure described in Step 4 of Example 1 from 7-methyl-1-[2-(dimethylamino)ethyl-1,3-dihydro-2H-benzimidazol-2-one (Step 1) and L-tert-leucinamide.
$^1$H-NMR (270 MHz, CDCl$_3$) δ 9.57 (d, J=7.8 Hz, 1H), 8.10 (d, J=7.8 Hz, 1H), 7.05 (t, J=7.8 Hz, 1H), 6.96 (d, J=8.1 Hz, 1H), 5.93 (bs, 1H), 5.62 (bs, 1H), 4.27-4.17 (m, 3H), 2.68-2.58 (m, 5H), 2.35 (s, 6H), 1.15 (s, 9H).
MS (ESI) m/z 376 (M+H)+
Anal. calcd. for C$_{19}$H$_{29}$N$_5$O$_3$: C, 60.78; H, 7.79; N, 18.65; O, 12.78. Found: C, 60.67; H, 7.89; N, 18.48.

Example 19

N-[(1S)-1-methylpropyl]-3-[2-(dimethylamino)ethyl]-4-methyl-2-oxo-2,3-dihydro-1H-benzimidazole-1-carboxamide

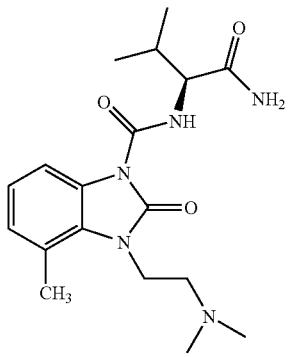

The title compound was prepared according to the procedure described in Step 4 of Example 1 from 7-methyl-1-[2-(dimethylamino)ethyl-1,3-dihydro-2H-benzimidazol-2-one (Step 1 of Example 18) and L-valinamide hydrochloride.
$^1$H-NMR (300 MHz, CDCl$_3$) δ 9.39 (d, J=8.1 Hz, 1H), 8.11 (d, J=8.1 Hz, 1H), 7.06 (d, J=8.1, Hz, 1H), 6.97 (d, J=7.2 Hz, 1H), 6.12 (bs, 1H), 5.50 (bs, 1H), 4.36 (dd, J=8.1, 5.1 Hz, 1H), 4.28-4.11 (m, 2H), 2.65-2.56 (m, 5H), 2.49-2.37 (m, 1H), 2.34 (s, 6H), 1.08 (d, J=3.0 Hz, 3H), 1.06 (d, J=3.0 Hz, 3H).
MS (ESI) m/z 362 (M+H)+
Anal. calcd. for C$_{18}$H$_{27}$N$_5$O$_3$(+0.7H$_2$O): C, 57.80; H, 7.65; N, 18.72; O, 15.83. Found: C, 57.96; H, 7.71; N, 18.35.

Example 20

N-((1S)-1-{[(2-Hydroxyethyl)amino]carbonyl}-2,2-dimethylpropyl)-3-(2-morpholin-4-ylethyl)-2-oxo-2,3-dihydro-1H-benzimidazole-1-carboxamide hydrochloride

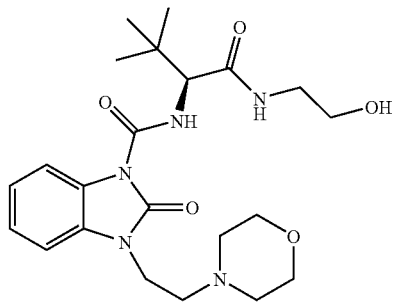

The title compound was prepared according to the procedure described in Step 4 of Example 1 from ethanolamine.
$^1$H-NMR (300 MHz, DMSO-d$_6$) δ 11.05 (bs, 1H), 9.14 (d, J=9.0 Hz, 1H), 8.30 (d, J=5.4 Hz, 1H), 8.06 (d, J=7.8, Hz, 1H), 7.51 (d, J=7.8 Hz, 1H), 7.30-7.17 (m, 2H), 4.42-4.37 (m, 2H), 4.32 (d, J=9.0 Hz, 1H), 3.80-3.70 (m, 2H), 3.94-3.65 (m, 6H), 3.25-3.06 (m, 4H), 0.98 (s, 9H).
MS (ESI) m/z 448 (M+H)+
Anal. calcd. for C$_{22}$H$_{33}$N$_5$O$_5$ (+1.0H$_2$O, 1.0HCl): C, 52.64; H, 7.23; N, 13.95; O, 19.12; Cl, 7.06. Found: C, 52.40; H, 7.48; N, 13.81.

Example 21

N-[(1S)-1-(Aminocarbonyl)-2,2-dimethylpropyl]-3-(2-morpholin-4-ylethyl)-2-oxo-2,3-dihydro-1H-imidazo[4,5-b]pyridine-1-carboxamide hydrochloride

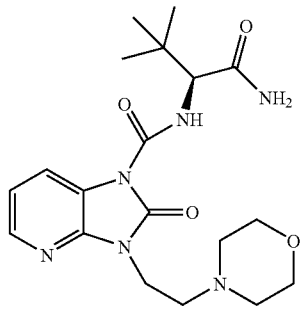

Step 1. 3-(2-morpholin-4-ylethyl)-2-oxo-2,3-dihydro-1H-imidazo[4,5-b]pyridine The title compound was prepared according to the procedure described in Steps 1 to 3 of Example 1 from 2-chloro-3-nitropyridine.

$^1$H-NMR (300 MHz, CDCl$_3$) δ 9.98 (bs, 1H), 8.07-8.03 (m, 1H), 7.28-7.21 (m, 1H), 6.98-6.94 (m, 1H), 4.17-4.13 (m, 2H), 3.67-3.64 (m, 4H), 2.83-2.79 (m, 2H), 2.60-2.57 (m, 4H).

MS (ESI) m/z 249 (M+H)$^+$, 247 (M−H)$^−$.

Step 2. N-[(1S)-(Aminocarbonyl)-2,2-dimethylpropyl]-3-(2-morpholin-4-ylethyl)-2-oxo-2,3-dihydro-1H-imidazo[4,5-b]pyridine-1-carboxamide hydrochloride The title compound was prepared according to the procedure described in Step 4 of Example 1 from 3-(2-morpholin-4-ylethyl)-2-oxo-2,3-dihydro-1H-imidazo[4,5-b]pyridine (Step 1) and L-tert-leucinamide.

$^1$H-NMR (300 MHz, DMSO-d$_6$) δ 11.40 (bs, 1H), 10.9 (bs, 1H), 8.93 (d, J=9.3 Hz, 1H), 8.22-8.14 (m, 1H), 7.72 (bs, 1H), 7.25-7.20 (m, 2H), 4.35 (t, J=5.4 Hz, 2H), 4.28 (d, J=9.0 Hz, 1H), 4.05-3.90 (m, 2H), 3.88-3.50 (m, 5H), 3.45-3.40 (m, 2H), 3.25-3.08 (m, 2H), 1.00 (s, 9H).

MS (ESI) m/z 405 (M+H)$^+$

Anal. calcd. for C$_{19}$H$_{28}$N$_6$O$_4$(+1.0H$_2$O, 1.0HCl): C, 49.72; H, 6.81; N, 18.31; O, 17.43; Cl, 7.72. Found: C, 50.05; H, 7.01; N, 18.04.

Example 22

N-[(1S)-1-(Aminocarbonyl)-2-methylpropyl]-3-(2-morpholin-4-ylethyl)-2-oxo-2,3-dihydro-1H-benzimidazole-1-carboxamide hydrochloride

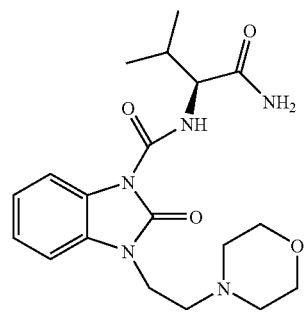

The title compound was prepared according to the procedure described in Step 4 of Example 1 from L-valinamide hydrochloride.

$^1$H-NMR (300 MHz, DMSO-d$_6$) δ 11.21 (bs, 1H), 9.00 (d, J=8.1 Hz, 1H), 8.04 (d, J=8.1 Hz, 1H), 7.67 (bs, 1H), 7.50 (d, J=7.2 Hz, 1H), 7.29-7.16 (m, 3H), 4.45-4.35 (m, 2H), 4.30 (dd, J=9.0, 5.1 Hz, 1H), 4.05-3.90 (m, 2H), 3.85-3.66 (m, 2H), 3.65-3.51 (m, 2H), 3.50-3.40 (m, 2H), 3.25-3.05 (m, 2H), 2.19-2.08 (m, 1H), 0.94 (d, J=6.6 Hz, 3H), 0.88 (d, J=6.6 Hz, 3H).

MS (ESI) m/z 390 (M+H)$^+$.

Anal. calcd. for C$_{19}$H$_{27}$N$_5$O$_4$ (+0.5H$_2$O, 1HCl, 0.2 C$_4$H$_8$O$_2$): C, 52.55; H, 6.82; N, 15.48; O, 17.32, Cl, 7.83. Found: C, 52.58; H, 6.81; N, 15.15.

Example 23

N-[(1S,2S)-1-(hydroxymethyl)-2-methylbutyl]-3-(2-morpholin-4-ylethyl)-2-oxo-2,3-dihydro-1H-benzimidazole-1-carboxamide

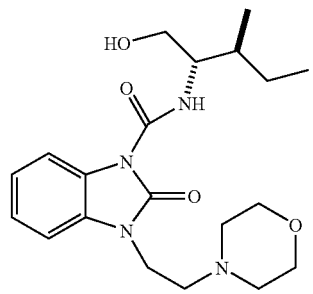

The title compound was prepared according to the procedure described in Step 4 of Example 1 from N-[(1S,2S)-1-(hydroxymethyl)-2-methylbutyl]amine.

MS (ESI) m/z 391 (M+H)$^+$.

Rt=1.09 min

Example 24

N-[(1S)-1-(hydroxymethyl)-2,2-dimethylpropyl]-3-(2-morpholin-4-ylethyl)-2-oxo-2,3-dihydro-1H-benzimidazole-1-carboxamide

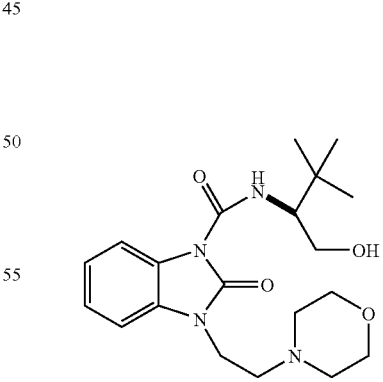

The title compound was prepared according to the procedure described in Step 4 of Example 1 from N-[(1S)-1-(hydroxymethyl)-2,2-dimethylpropyl]amine.

MS (ESI) m/z 391 (M+H)$^+$.

Rt=1.67 min

Example 25

N-[(1S)-(hydroxymethyl)-3-methylbutyl]-3-(2-morpholin-4-ylethyl)-2-oxo-2,3-dihydro-1H-benzimidazole-1-carboxamide

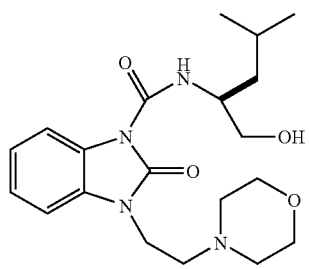

The title compound was prepared according to the procedure described in Step 4 of Example 1 from N-[(1S)-1-(hydroxymethyl)-3-methylbutyl]amine.

MS (ESI) m/z 391 (M+H)+.

Rt=1.76 min

Example 26

N-{1-[(dimethylamino)carbonyl]-1,3-dimethylbutyl}-3-(2-morpholin-4-ylethyl)-2-oxo-2,3-dihydro-1H-benzimidazole-1-carboxamide

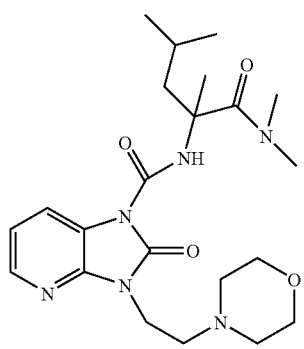

The title compound was prepared according to the procedure described in Step 4 of Example 1 from N-{1-[(dimethylamino)carbonyl]-1,3-dimethylbutyl}amine.

MS (ESI) m/z 446 (M+H)+.

Rt=1.74 min

Example 27

N-[(1S)-1-(Aminocarbonyl)-2,2-dimethylpropyl]-4-chloro-3-(2-morpholin-4-ylethyl)-2-oxo-2,3-dihydro-1H-benzimidazole-1-carboxamide

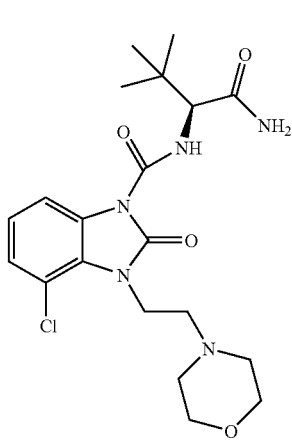

Step 1. 7-Chloro-1-(2-morpholin-4-ylethyl)-1,3-dihydro-2H-benzimidazol-2-one

The title compound was prepared according to the procedure described in Steps 1 to 3 of Example 1 from 1,2-dichloro-3-nitrobenzene.

$^1$H-NMR (300 MHz, DMSO-$d_6$) δ 11.2 (s, 1H), 7.05-6.87 (m, 3H), 4.23-4.10 (m, 2H), 3.59-3.48 (m, 4H), 2.62-2.37 (m, 6H).

Step 2. N-[(1S)-1-(Aminocarbonyl)-2,2-dimethylpropyl]-4-chloro-3-(2-morpholin-4-ylethyl)-2-oxo-2,3-dihydro-1H-benzimidazole-1-carboxamide The title compound was prepared according to the procedure described in Step 4 of Example 1 from 7-Chloro-1-(2-morpholin-4-ylethyl)-1,3-dihydro-2H-benzimidazol-2-one (Step 1).

$^1$H-NMR (300 MHz, CDCl$_3$) δ 9.51 (d, J=8.1 Hz, 1H), 8.18 (d, J=9.2 Hz, 1H), 7.20-7.03 (m, 2H), 5.89 (bs, 1H), 5.71 (bs, 1H), 4.44-4.34 (m, 2H), 4.21 (d, J=8.1 Hz, 1H), 3.70-3.60 (m, 4H), 2.83-2.44 (m, 6H), 1.14 (s, 9H).

Example 28

N-[(1S)-1-(Aminocarbonyl)-2,2-dimethylpropyl]-5-chloro-3-(2-morpholin-4-ylethyl)-2-oxo-2,3-dihydro-1H-benzimidazole-1-carboxamide

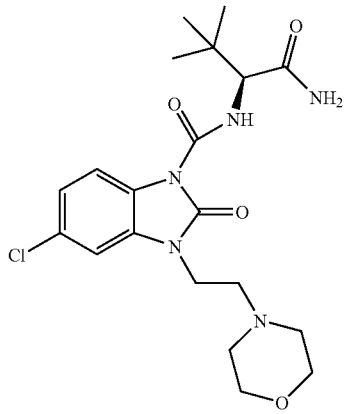

Step 1. 6-Chloro-1-(2-morpholin-4-ylethyl)-1,3-dihydro-2H-benzimidazol-2-one The title compound was prepared according to the procedure described in Steps 1 to 3 of Example 1 from 4-chloro-2-fluoronitrobenzene.

$^1$H-NMR (300 MHz, CDCl$_3$) δ 10.1 (s, 1H), 7.12-6.93 (m, 3H), 4.06-3.89 (m, 2H), 3.79-3.60 (m, 4H), 2.79-2.47 (m, 6H).

Step 2. N-[(1S)-1-(Aminocarbonyl)-2,2-dimethylpropyl]-5-chloro-3-(2-morpholin-4-ylethyl)-2-oxo-2,3-dihydro-1H-benzimidazole-1-carboxamide The title compound was prepared according to the procedure described in Step 4 of Example 1 from 6-Chloro-1-(2-morpholin-4-ylethyl)-1,3-dihydro-2H-benzimidazol-2-one (Step 1).

$^1$H-NMR (300 MHz, DMSO-d$_6$) δ 9.04 (d, J=9.2 Hz, 1H), 8.03 (d, J=8.6 Hz, 1H), 7.74-7.65 (m, 2H), 7.29-7.19 (m, 2H), 4.42-4.31 (m, 2H), 4.07 (d, J=8.6 Hz, 1H), 4.08-3.94 (m, 2H), 3.82-3.07 (m, 8H), 0.99 (s, 9H).

Example 29

N-[(1S)-1-(Aminocarbonyl)-2,2-dimethylpropyl]-3-[(4-hydroxytetrahydro-2H-pyran-4-yl)methyl]-2-oxo-2,3-dihydro-1H-benzimidazole-1-carboxamide

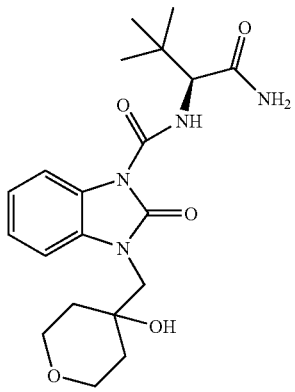

Step 1. 1-[(4-Hydroxytetrahydro-2H-pyran-4-yl)methyl]-1,3-dihydro-2H-benzimidazol-2-one The title compound was prepared according to the procedure described in Steps 1 to 3 of Example 1 from 4-{[(2-Nitrophenyl)amino]methyl}tetrahydro-2H-pyran-4-ol (WO 2004029026).

$^1$H-NMR (300 MHz, DMSO-d$_6$) δ 10.9 (bs, 1H), 7.28-7.20 (m, 1H), 7.01-6.94 (m, 3H), 4.76 (s, 1H), 3.73 (s, 2H), 3.66-3.51 (m, 4H), 1.69-1.35 (m, 4H).

Step 2. N-[(1S)-1-(Aminocarbonyl)-2,2-dimethylpropyl]-3-[(4-hydroxytetrahydro-2H-pyran-4-yl)methyl]-2-oxo-2,3-dihydro-1H-benzimidazole-1-carboxamide The title compound was prepared according to the procedure described in Step 4 of Example 1 from 1-[(4-Hydroxytetrahydro-2H-pyran-4-yl)methyl]-1,3-dihydro-2H-benzimidazol-2-one (Step 1).

$^1$H-NMR (300 MHz, DMSO-d$_6$) δ 9.23 (d, J=8.8 Hz, 1H), 8.04 (d, J=7.5 Hz, 1H), 7.71-7.63 (m, 1H), 7.44-7.36 (m, 1H), 7.26-7.07 (m, 3H), 4.78 (s, 1H), 4.27 (d, J=9.0 Hz, 1H), 3.91-3.47 (m, 6H), 1.74-1.36 (m, 4H), 0.99 (s, 9H).

Example 30

N-[(1S)-1-(Aminocarbonyl)-2,2-dimethylpropyl]-3-[2-(4-hydroxytetrahydro-2H-pyran-4-yl)ethyl]-2-oxo-2,3-dihydro-1H-benzimidazole-1-carboxamide

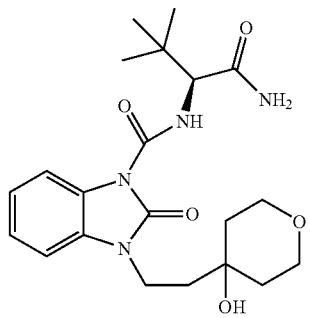

Step 1. 1,6-Dioxaspiro[2.5]octane-2-carbonitrile

To a mixture of tetrahydro-4H-pyran-4-one (5.0 g, 50 mmol) and chloroacetonitrile (3.8 g, 50 mmol) was dropwise added a solution of potassium tert-butoxide in tert-butanol (1.0 M, 50 mL). The reaction mixture was stirred overnight and quenched with water (100 mL). The whole was extracted with ethyl acetate (200 mL). The organic layer was washed with water and brine, dried over magnesium sulfate, filtered and concentrated in vacuo to afford the titled compound. (5.65 g)

$^1$H-NMR (300 MHz, CDCl$_3$) δ 3.94-3.79 (m, 4H), 3.35 (s, 1H); 2.17-2.03 (m, 1H), 1.97-1.76 (m, 2H), 1.65-1.53 (m, 1H).

Step 2. 4-(2-Aminoethyl)tetrahydro-2H-pyran-4-ol hydrochloride

A mixture of 1,6-dioxaspiro[2.5]octane-2-carbonitrile (3.0 g, 22 mmol) and 5% Pd on C (0.3 g) in methanol (40 mL) was stirred for 2 h. under hydrogen (3 kg/cm$^2$). After filtration through a pad of celite, the filtrate was concentrated in vacuo. The residue was dissolved with THF (50 mL). The solution was added dropwise to a mixture of lithium aluminum hydride (1.6 g, 43 mmol) and THF (100 mL) and the mixture was stirred for 2 h. at reflux temperature. After cooling to 0° C., Na$_2$SO$_4$-10H$_2$O (16 g) and KF (2.5 g) were added and the mixture was stirred overnight. After filtration, the filtrate was concentrated in vacuo. The residue was acidified with 4N-HCl in ethyl acetate and concentrated in vacuo. The residue was crystallized from ethanol-ether. The precipitate was filtered to afford the titled compound. (2.1 g)
$^1$H-NMR (300 MHz, DMSO-d$_6$) δ 8.19-7.78 (m, 4H), 3.81-3.35 (m, 4H), 2.98-2.77 (m, 2H), 1.81-1.34 (m, 6H).

Step 3. 1-[2-(4-Hydroxytetrahydro-2H-pyran-4-yl)ethyl]-1,3-dihydro-2H-benzimidazol-2-one The title compound was prepared according to the procedure described in Steps 1 to 3 of Example 1 from 4-(2-Aminoethyl)tetrahydro-2H-pyran-4-ol hydrochloride (Step 2).
$^1$H-NMR (300 MHz, DMSO-d$_6$) δ 10.8 (bs, 1H), 7.14-6.91 (m, 4H), 4.57 (s, 1H), 3.95-3.81 (m, 2H), 3.70-3.44 (m, 4H), 1.75-1.42 (m, 6H).

Step 4. N-[(1S)-1-(Aminocarbonyl)-2,2-dimethylpropyl]-3-[2-(4-hydroxytetrahydro-2H-pyran-4-yl)ethyl]-2-oxo-2,3-dihydro-1H-benzimidazole-1-carboxamide The title compound was prepared according to the procedure described in Step 4 of Example 1 from 1-[2-(4-Hydroxytetrahydro-2H-pyran-4-yl)ethyl]-1,3-dihydro-2H-benzimidazol-2-one (Step 3).
$^1$H-NMR (300 MHz, DMSO-d$_6$) δ 9.23 (d, J=9.2 Hz, 1H), 8.05 (d, J=7.9 Hz, 1H), 7.72-7.64 (m, 1H), 7.35-7.12 (m, 4H), 4.61 (s, 1H), 4.26 (d, J=9.2 Hz, 1H), 4.08-3.91 (m, 2H), 3.75-3.47 (m, 4H), 1.87-1.44 (m, 4H), 1.00 (s, 9H).

Example 31

N-[(1S)-1-(Aminocarbonyl)-2,2-dimethylpropyl]-3-[2-(ethylthio)ethyl]-2-oxo-2,3-dihydro-1H-benzimidazole-1-carboxamide

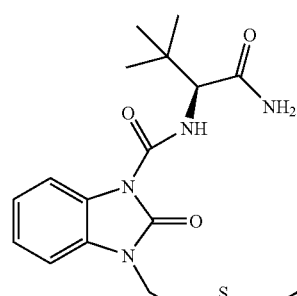

Step 1. 1-[2-(Ethylthio)ethyl]-1,3-dihydro-2H-benzimidazol-2-one

The title compound was prepared according to the procedure described in Steps 1 to 3 of Example 1 from 2-(ethylthio)ethanamine hydrochloride.
$^1$H-NMR (300 MHz, CDCl$_3$) δ 8.97 (bs, 1H), 7.17-6.96 (m, 4H), 4.14-4.02 (m, 2H), 2.95-2.84 (m, 2H), 1.69-1.35 (m, 4H), 2.63 (q, J=7.3 Hz, 2H), 1.28 (t, J=7.3 Hz, 3H)

Step 2. N-[(1S)-1-(Aminocarbonyl)-2,2-dimethylpropyl]-3-[2-(ethylthio)ethyl]-2-oxo-2,3-dihydro-1H-benzimidazole-1-carboxamide The title compound was prepared according to the procedure described in Step 4 of Example 1 from 1-[2-(Ethylthio)ethyl]-1,3-dihydro-2H-benzimidazol-2-one (Step 1).
$^1$H-NMR (300 MHz, DMSO-d$_6$) δ 9.20 (d, J=8.8 Hz, 1H), 8.05 (d, J=7.9 Hz, 1H), 7.73-7.65 (m, 1H), 7.42-7.11 (m, 4H), 4.27 (d, J=8.8 Hz, 1H), 4.15-4.04 (m, 2H), 2.95-2.83 (m, 2H), 2.65-2.54 (m, 2H), 1.21-1.13 (m, 3H), 0.99 (s, 9H).

Example 32

N-[(1S)-1-(Aminocarbonyl)-2,2-dimethylpropyl]-3-[2-(methylthio)ethyl]-2-oxo-2,3-dihydro-1H-benzimidazole-1-carboxamide

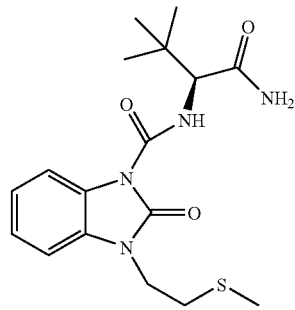

Step 1. 1-[2-(Methylthio)ethyl]-1,3-dihydro-2H-benzimidazol-2-one

The title compound was prepared according to the procedure described in Steps 1 to 3 of Example 1 from 2-(methylthio)ethanamine.
$^1$H-NMR (300 MHz, CDCl$_3$) δ 9.36 (bs, 1H), 7.17-6.99 (m, 4H), 4.18-4.04 (m, 2H), 2.94-2.81 (m, 2H), 2.20 (s, 3H).

Step 2. N-[(1S)-1-(Aminocarbonyl)-22-dimethylpropyl]-3-[2-(methylthio)ethyl]-2-oxo-2,3-dihydro-1H-benzimidazole-1-carboxamide The title compound was prepared according to the procedure described in Step 4 of Example 1 from 1-[2-(Methylthio)ethyl]-1,3-dihydro-2H-benzimidazol-2-one (Step 1).

¹H-NMR (300 MHz, DMSO-d₆) δ 9.19 (d, J=9.2 Hz, 1H), 8.06 (d, J=7.9 Hz, 1H), 7.72-7.64 (m, 1H), 7.42-7.12 (m, 4H), 4.27 (d, J=8.6 Hz, 1H), 4.17-4.06 (m, 2H), 2.90-2.81 (m, 2H), 2.14 (s, 3H), 1.00 (s, 9H).

Example 33

N-[(1S)-1-(aminocarbonyl)-2,2-dimethylpropyl]-3-[2-(methylsulfinyl)ethyl]-2-oxo-2,3-dihydro-1H-benzimidazole-1-carboxamide

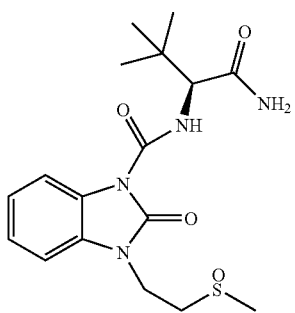

A mixture of N-[(1S)-1-(aminocarbonyl)-2,2-dimethylpropyl]-3-[2-(methylthio)ethyl]-2-oxo-2,3-dihydro-1H-benzimidazole-1-carboxamide (Example 32, 150 mg), m-chloroperbenzoic acid (70%, 170 mg) and NaHCO3 (150 mg) in dichloromethane (5 mL) was stirred overnight and quenched with sat. Na₂S₂O₃ aq. (25 mL) The whole was extracted with ethyl acetate (25 mL×2). The combined organic layers were washed with brine, dried over magnesium sulfate, filtrated and concentrated in vacuo. The residue was purified by preparative TLC to yield the titled compound. (180 mg)

¹H-NMR (300 MHz, CDCl₃) δ 9.39-9.29 (m, 1H), 8.12 (d, J=7.9 Hz, 1H), 7.31-7.11 (m, 3H), 6.46-6.36 (m, 1H), 6.19-6.07 (m, 1H), 4.43-4.32 (m, 2H), 4.28 (d, J=8.6 Hz, 1H), 3.33-2.99 (m, 2H), 2.67 (s, 3H), 1.13 (s, 9H).

Example 34

N-[(1S)-1-(Aminocarbonyl)-2,2-dimethylpropyl]-3-[2-(methylsulfonyl)ethyl]-2-oxo-2,3-dihydro-1H-benzimidazole-1-carboxamide

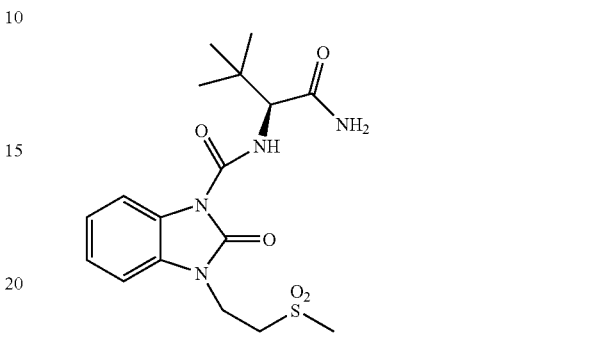

A mixture of N-[(1S)-1-(aminocarbonyl)-2,2-dimethylpropyl]-3-[2-(methylsulfinyl)ethyl]-2-oxo-2,3-dihydro-1H-benzimidazole-1-carboxamide (Example 33, 150 mg), m-chloroperbenzoic acid (70%, 170 mg) and NaHCO₃ (150 mg) in dichloromethane (5 mL) was stirred overnight and quenched with sat. Na2S2O3 aq. (25 mL) The whole was extracted with ethyl acetate (25 mL×2). The combined organic layers were washed with brine, dried over magnesium sulfate, filtrated and concentrated in vacuo. The residue was purified by preparative TLC to yield the titled compound. (100 mg)

¹H-NMR (300 MHz, DMSO-d₆) δ 9.14 (d, J=8.6 Hz, 1H), 8.06 (d, J=7.9 Hz, 1H), 7.74-7.65 (m, 1H), 7.43-7.15 (m, 4H), 4.40-4.24 (m, 3H), 3.72-3.53 (m, 2H), 3.11 (s, 3H), 1.00 (s, 9H).

Following Examples 35 to 90 were prepared according to the procedure described in Step 4 of Example 1.

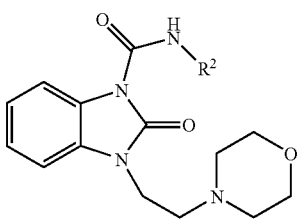

| Example 35 | Methyl N-{[3-(2-Morpholin-4-ylethyl)-2-oxo-2,3-dihydro-1H-benzimidazol-1-yl]carbonyl}-L-phenylalaninate |
|---|---|
| 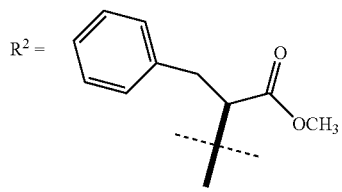 | ¹H-NMR (300 MHz, CDCl₃) δ 9.25 (d, J =7.5 Hz, 1 H), 8.17-8.14 (m, 1 H), 7.33-7.12 (m, 7 H), 7.03-7.00 (m, 1 H), 4.89 (dt, J = 7.5, 5.7 Hz, 1 H), 4.04-3.94 (m, 2 H), 3.74 (s, 3 H), 3.66 (t, J = 4.8 Hz, 4 H), 3.28 (dd, J = 13.8, 5.4 Hz, 1 H), 3.15 (dd, J = 13.8, 7.5 Hz, 1 H), 2.72-2.62 (m, 2 H), 2.57-2.47 (m, 4 H). MS (ESI) m/z 453 (M + H)⁺. |

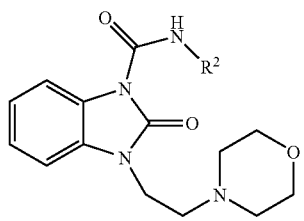

Example 36

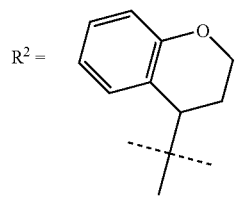
R² =

N-(3,4-Dihydro-2H-chromen-4-yl)-3-(2-morpholin-4-ylethyl)-2-oxo-2,3-dihydro-1H-benzimidazole-1-carboxamide hydrochloride $^1$H-NMR (300 MHz, CDCl$_3$) δ 13.81 (bs, 1 H), 8.87 (d, J = 7.5 Hz, 1 H), 8.24 (d, J = 7.5 Hz, 1 H), 7.57 (d, J = 7.5 Hz, 1 H), 7.34-7.18 (m, 4 H), 6.95-6.85 (m, 2 H), 5.26-5.20 (m, 1 H), 4.65-4.50 (m, 2 H), 4.37-3.92 (m, 6 H), 3.57-3.40 (m, 2 H), 3.35-3.22 (m, 2 H), 3.10-2.85 (m, 2 H), 2.40-2.30 (m, 1 H), 2.23-2.14 (m, 1 H).
MS (ESI) m/z 423 (M + H)$^+$.
Anal. calcd. for C$_{23}$H$_{26}$N$_4$O$_4$ (+0.6 H$_2$O, 1 HCl): C, 58.81; H, 6.05; N, 11.93; O, 15.67, Cl, 7.75. Found: C, 59.13; H, 6.23; N; 11.53.
IR (KBr)ν$_{max}$ 1728, 1537, 1489, 1385 cm$^{-1}$.

Example 37

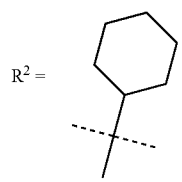
R² =

N-cyclohexyl-3-(2-morpholin-4-ylethyl)-2-oxo-2,3-dihydro-1H-benzimidazole-1-carboxamide MS (ESI) m/z 373 (M + H)$^+$.
Rt = 1.96 min Example 38

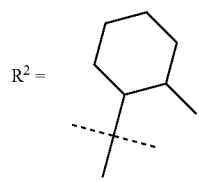
R² =

N-(2-methylcyclohexyl)-3-(2-morpholin-4-ylethyl)-2-oxo-2,3-dihydro-1H-benzimidazole-1-carboxamide MS (ESI) m/z 387 (M + H)$^+$.
Rt = 1.24 min Example 39

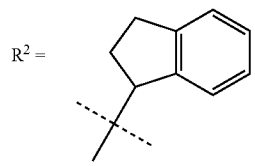
R² =

N-(2,3-dihydro-1H-inden-1-yl)-3-(2-morpholin-4-ylethyl)-2-oxo-2,3-dihydro-1H-benzimidazole-1-carboxamide MS (ESI) m/z 407 (M + H)$^+$.
Rt = 1.22 min Example 40

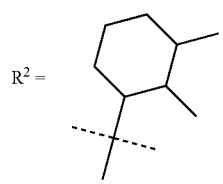
R² =

N-(2,3-dimethylcyclohexyl)-3-(2-morpholin-4-ylethyl)-2-oxo-2,3-dihydro-1H-benzimidazole-1-carboxamide MS (ESI) m/z 401 (M + H)$^+$.
Rt = 1.32 min -continued

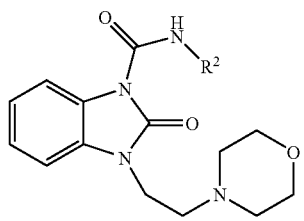

Example 41

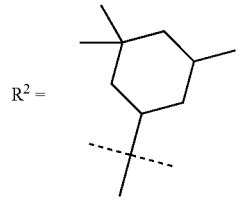

R² =

3-(2-morpholin-4-ylethyl)-2-oxo-N-(3,3,5-trimethylcyclohexyl)-2,3-dihydro-1H-benzimidazole-1-carboxamide MS (ESI) m/z 415 (M + H)⁺.
Rt = 1.37 min Example 42

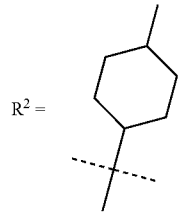

R² =

N-(4-methylcyclohexyl)-3-(2-morpholin-4-ylethyl)-2-oxo-2,3-dihydro-1H-benzimidazole-1-carboxamide MS (ESI) m/z 387 (M + H)⁺.
Rt = 1.26 min Example 43

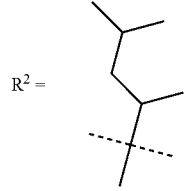

R² =

N-(1,3-dimethylbutyl)-3-(2-morpholin-4-ylethyl)-2-oxo-2,3-dihydro-1H-benzimidazole-1-carboxamide MS (ESI) m/z 375 (M + H)⁺.
Rt = 1.24 min Example 44

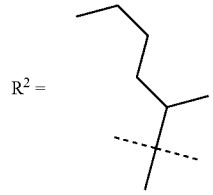

R² =

N-(1-methylpentyl)-3-(2-morpholin-4-ylethyl)-2-oxo-2,3-dihydro-1H-benzimidazole-1-carboxamide MS (ESI) m/z 375 (M + H)⁺.
Rt = 1.24 min Example 45

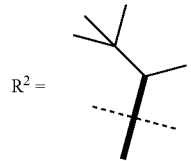

R² =

3-(2-morpholin-4-ylethyl)-2-oxo-N-[(1R)-1,2,2-trimethylpropyl]-2,3-dihydro-1H-benzimidazole-1-carboxamide MS (ESI) m/z 375 (M + H)⁺.
Rt = 1.21 min

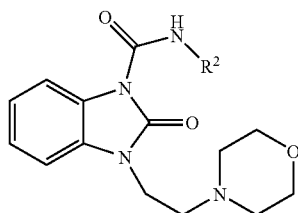

Example 46

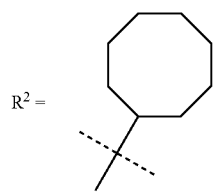

R² =

N-cyclooctyl-3-(2-morpholin-4-ylethyl)-2-oxo-2,3-dihydro-1H-benzimidazole-1-carboxamide MS (ESI) m/z 401 (M + H)⁺.
Rt = 1.31 min Example 47

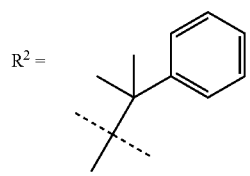

R² =

N-(1-methyl-1-phenylethyl)-3-(2-morpholin-4-ylethyl)-2-oxo-2,3-dihydro-1H-benzimidazole-1-carboxamide MS (ESI) m/z 409 (M + H)⁺.
Rt = 1.21 min Example 48

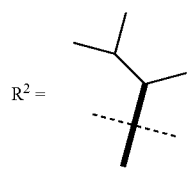

R² =

N-[(1R)-1,2-dimethylpropyl]-3-(2-morpholin-4-ylethyl)-2-oxo-2,3-dihydro-1H-benzimidazole-1-carboxamide MS (ESI) m/z 361 (M + H)⁺.
Rt = 1.17 min Example 49

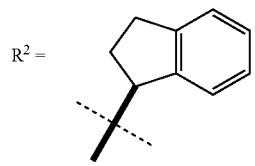

R² =

N-[(1S)-2,3-dihydro-1H-inden-1-yl]-3-(2-morpholin-4-ylethyl)-2-oxo-2,3-dihydro-1H-benzimidazole-1-carboxamide MS (ESI) m/z 407 (M + H)⁺.
Rt = 1.22 min Example 50

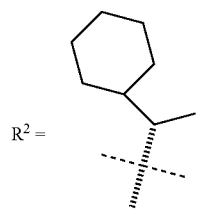

R² =

N-[(1S)-1-cyclohexylethyl]-3-(2-morpholin-4-ylethyl)-2-oxo-2,3-dihydro-1H-benzimidazole-1-carboxamide MS (ESI) m/z 401 (M + H)⁺.
Rt = 1.32 min -continued

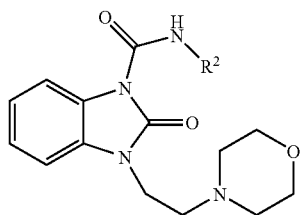

Example 51

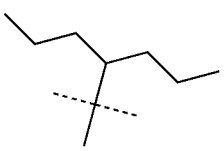
R² =

3-(2-morpholin-4-ylethyl)-2-oxo-N-(1-propylbutyl)-2,3-dihydro-1H-benzimidazole-1-carboxamide MS (ESI) m/z 389 (M + H)⁺.
Rt = 1.29 min Example 52

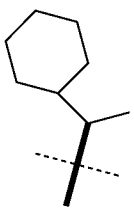
R² =

N-[(1R)-1-cyclohexylethyl]-3-(2-morpholin-4-ylethyl)-2-oxo-2,3-dihydro-1H-benzimidazole-1-carboxamide MS (ESI) m/z 401 (M + H)⁺.
Rt = 1.32 min Example 53

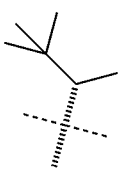
R² =

3-(2-morpholin-4-ylethyl)-2-oxo-N-[(1S)-1,2,2-trimethylpropyl]-2,3-dihydro-1H-benzimidazole-1-carboxamide MS (ESI) m/z 375 (M + H)⁺.
Rt = 1.21 min Example 54

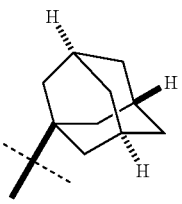
R² =

N-[(3S,5S,7S)-1-adamantyl]-3-(2-morpholin-4-ylethyl)-2-oxo-2,3-dihydro-1H-benzimidazole-1-carboxamide MS (ESI) m/z 425 (M + H)⁺.
Rt = 1.22 min Example 55

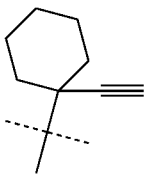
R² =

N-(1-ethynylcyclohexyl)-3-(2-morpholin-4-ylethyl)-2-oxo-2,3-dihydro-1H-benzimidazole-1-carboxamide MS (ESI) m/z 397 (M + H)⁺.
Rt = 1.20 min

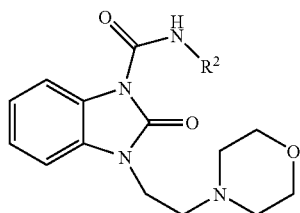

Example 56

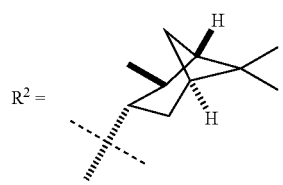
R² =

3-(2-morpholin-4-ylethyl)-2-oxo-N-[(1S,2R,3S,5R)-2,6,6-trimethylbicyclo[3.1.1]hept-3-yl]-2,3-dihydro-1H-benzimidazole-1-carboxamide MS (ESI) m/z 427 (M + H)⁺.
Rt = 1.38 min Example 57

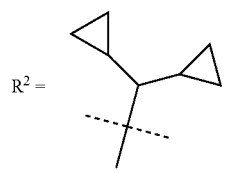
R² =

N-(dicyclopropylmethyl)-3-(2-morpholin-4-ylethyl)-2-oxo-2,3-dihydro-1H-benzimidazole-1-carboxamide MS (ESI) m/z 385 (M + H)⁺.
Rt = 1.20 min Example 58

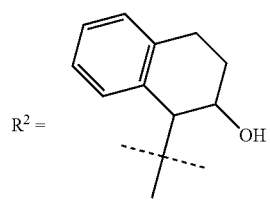
R² =

N-(2-hydroxy-1,2,3,4-tetrahydronaphthalen-1-yl)-3-(2-morpholin-4-ylethyl)-2-oxo-2,3-dihydro-1H-benzimidazole-1-carboxamide MS (ESI) m/z 437 (M + H)⁺.
Rt = 1.13 min Example 59

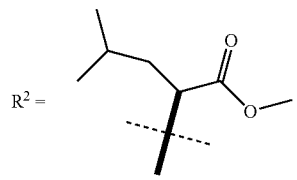
R² = methyl N-{[3-(2-morpholin-4-ylethyl)-2-oxo-2,3-dihydro-1H-benzimidazol-1-yl]carbonyl}-L-leucinate MS (ESI) m/z 419 (M + H)⁺.
Rt = 1.18 min Example 60

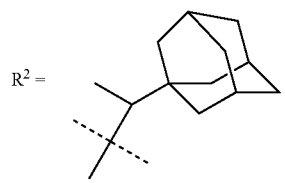
R² =

N-[1-(1-adamantyl)ethyl]-3-(2-morpholin-4-ylethyl)-2-oxo-2,3-dihydro-1H-benzimidazole-1-carboxamide MS (ESI) m/z 453 (M + H)⁺.
Rt = 1.44 min -continued

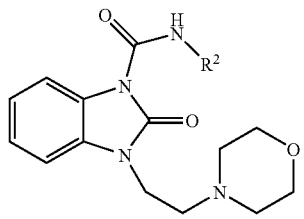

Example 61

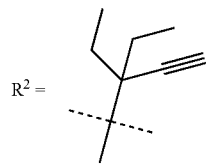

R² =

N-(1,1-diethylprop-2-yn-1-yl)-3-(2-morpholin-4-ylethyl)-2-oxo-2,3-dihydro-1H-benzimidazole-1-carboxamide MS (ESI) m/z 385 (M + H)⁺.
Rt = 1.21 min Example 62

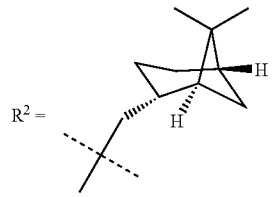

R² =

N-{[(1S,2R,5S)-6,6-dimethylbicyclo[3.1.1]hept-2-yl]methyl}-3-(2-morpholin-4-ylethyl)-2-oxo-2,3-dihydro-1H-benzimidazole-1-carboxamide MS (ESI) m/z 427 (M + H)⁺.
Rt = 1.38 min Example 63

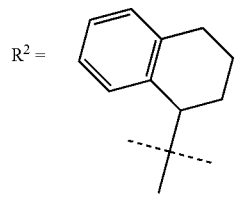

R² =

3-(2-morpholin-4-ylethyl)-2-oxo-N-(1,2,3,4-tetrahydronaphthalen-1-yl)-2,3-dihydro-1H-benzimidazole-1-carboxamide MS (ESI) m/z 421 (M + H)⁺.
Rt = 2.16 min Example 64

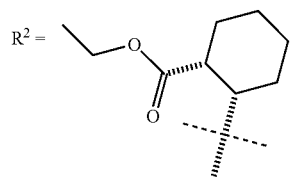

R² = ethyl (1R,2S)-2-({[3-(2-morpholin-4-ylethyl)-2-oxo-2,3-dihydro-1H-benzimidazol-1-yl]carbonyl}amino)cyclohexanecarboxylate MS (ESI) m/z 445 (M + H)⁺.
Rt = 1.98 min Example 65

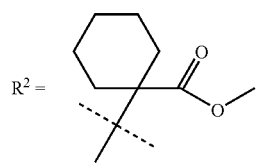

R² = methyl 1-({[3-(2-morpholin-4-ylethyl)-2-oxo-2,3-dihydro-1H-benzimidazol-1-yl]carbonyl}amino)cyclohexanecarboxylate MS (ESI) m/z 431 (M + H)⁺.
Rt = 1.88 min

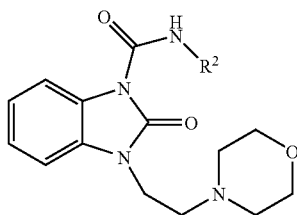

Example 66

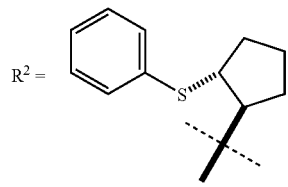
R² =

3-(2-morpholin-4-ylethyl)-2-oxo-N-[(1R,2R)-2-(phenylthio)cyclopentyl]-2,3-dihydro-1H-benzimidazole-1-carboxamide MS (ESI) m/z 467 (M + H)⁺.
Rt = 2.25 min Example 67

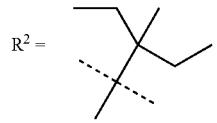
R² =

N-(1-ethyl-1-methylpropyl)-3-(2-morpholin-4-ylethyl)-2-oxo-2,3-dihydro-1H-benzimidazole-1-carboxamide MS (ESI) m/z 375 (M + H)⁺.
Rt = 1.36 min Example 68

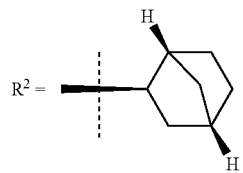
R² =

N-[(1R,2R,4S)-bicyclo[2.2.1]hept-2-yl]-3-(2-morpholin-4-ylethyl)-2-oxo-2,3-dihydro-1H-benzimidazole-1-carboxamide MS (ESI) m/z 385 (M + H)⁺.
Rt = 2.02

Example 69

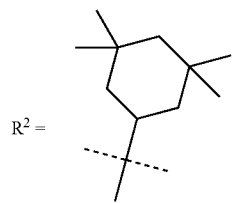
R² =

3-(2-morpholin-4-ylethyl)-2-oxo-N-(3,3,5,5-tetramethylcyclohexyl)-2,3-dihydro-1H-benzimidazole-1-carboxamide MS (ESI) m/z 429 (M + H)⁺.
Rt = 2.48 min Example 70

R² =

3-(2-morpholin-4-ylethyl)-2-oxo-N-(1,1,3,3-tetramethylbutyl)-2,3-dihydro-1H-benzimidazole-1-carboxamide MS (ESI) m/z 303 (M + H)⁺.
Rt = 2.35 min Example 71

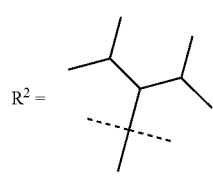
R² =

N-(1-isopropyl-2-methylpropyl)-3-(2-morpholin-4-ylethyl)-2-oxo-2,3-dihydro-1H-benzimidazole-1-carboxamide MS (ESI) m/z 389 (M + H)⁺.
Rt = 1.36 min -continued

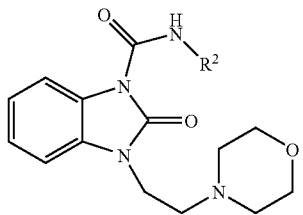

Example 72

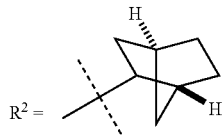

R² =

N-[(1S,4R)-bicyclo[2.2.1]hept-2-yl]-3-(2-morpholin-4-ylethyl)-2-oxo-2,3-dihydro-1H-benzimidazole-1-carboxamide MS (ESI) m/z 385 (M + H)⁺.
Rt = 2.00 min Example 73

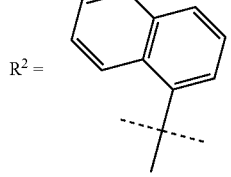

R² =

3-(2-morpholin-4-ylethyl)-N-1-naphthyl-2-oxo-2,3-dihydro-1H-benzimidaole-1-carboxamide $^1$H-NMR (300 MHz, CDCl$_3$) δ 11.50 (bs, 1 H), 8.37-8.34 (m, 1 H), 8.26 (d, J = 7.5 Hz, 1 H), 8.16 (d, J = 8.4 Hz, 1 H), 7.91-7.89 (m, 1 H), 7.71 (d, J = 8.3 Hz, 1 H), 7.63-7.51 (m, 3 H), 7.30-7.22 (m, 2 H), 7.13-7.10 (m, 1 H), 4.12 (t, J = 6.6 Hz, 2 H), 3.72-3.68 (m, 4 H), 2.77 (t, J = 6.6 Hz, 2 H), 2.57-2.60 (m, 4 H).
MS (ESI) m/z 417.2 (M + H)⁺.
Anal. calcd. for C$_{24}$H$_{24}$N$_4$O$_3$: C, 69.21; H, 5.81; N, 13.45; O, 11.52. Found: C, 69.35; H, 5.84; N; 13.49.
IR (KBr)ν$_{max}$ 2849, 1730, 1690, 1564, 1489, 1385 cm$^{-1}$.
mp 137.3, 128.3° C.

Example 74

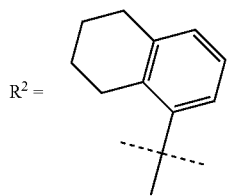

R² =

3-(2-morpholin-4-ylethyl)-2-oxo-N-(5,6,7,8-tetrahydonaphthalen-1-yl)-2,3-dihydro-1H-benzimidazole-1-carboxamide $^1$H-NMR (300 MHz, CDCl$_3$) δ 10.69 (bs, 1 H), 8.34-8.31 (m, 1 H), 7.93 (d, J = 8.0 Hz, 1 H), 7.27-7.15 (m, 3 H), 7.09-7.06 (m, 1 H), 6.93 (d, J = 7.7 Hz, 1 H), 4.06 (t, J = 6.8 Hz, 2 H), 3.69-3.66 (m, 4 H), 2.83-2.70 (m, 6 H), 2.57-2.54 (m, 4 H), 1.94-1.86 (m, 2 H), 1.82-1.74 (m, 2 H).
MS (ESI) m/z 421.2 (M + H)⁺.
Anal. calcd. for C$_{24}$H$_{28}$N$_4$O$_3$: C, 68.55; H, 6.71; N, 13.32; O, 11.41. Found: C, 68.34; H, 6.73; N; 13.12.
IR (KBr)ν$_{max}$ 2945, 1732, 1609, 1568, 1387, 1302, 1159, 1117 cm$^{-1}$.
mp 141.5° C.

Example 75

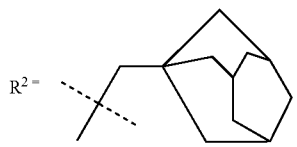

R² =

N-(1-adamantylmethyl)-3-(2-morpholin-4-ylethyl)-2-oxo-2,3-dihydro-1H-benzimidazole-1-carboxamide $^1$H-NMR (300 MHz, CDCl$_3$) δ 8.86-8.82 (m, 1 H), 8.26-8.23 (m, 1 H), 7.24-7.14 (m, 2 H), 7.05-7.02 (m, 1 H), 4.02 (t, J = 6.8 Hz, 2 H), 3.69-3.66 (m, 4 H), 3.13 (d, J = 6.0 Hz, 2 H), 2.70 (t, J = 6.8 Hz, 2 H), 2.55-2.52 (m, 4 H), 2.00 (bs, 3 H), 1.75-1.63 (m, 6 H), 1.59-1.58(m, 6 H).
MS (ESI) m/z 439.3 (M + H)⁺.
Anal. calcd. for C$_{25}$H$_{34}$N$_4$O$_3$: C, 68.47; H, 7.81; N, 12.78; O, 10.94. Found: C, 68.66; H, 7.82; N; 12.69.
IR (KBr)ν$_{max}$ 2907, 1730, 1558, 1393 cm$^{-1}$.
mp 142.0° C.

Example 76

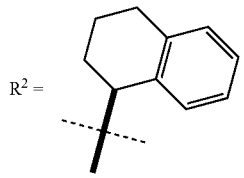

R² =

3-(2-morpholin-4-ylethyl)-2-oxo-N-[(1S)-1,2,3,4-tetrahydronaphthalen-1-yl]-2,3-dihydro-1H-benzimidazole-1-carboxamide hydrochloride $^1$H-NMR (300 MHz, CDCl$_3$) δ 13.86 (bs, 1 H), 8.82 (d, J = 8.4 Hz, 1 H), 8.27 (dd, J = 8.1, 1.5 Hz, 1 H), 7.58-7.55 (m, 1 H), 7.41-7.36 (m, 1 H), 7.32-7.11 (m, 4 H), 5.29-5.23 (m, 1 H), 4.61-4.57 (m, 2 H), 4.28-4.20 (m, 2 H), 3.99 (d, J = 11.7 Hz, 2 H),
3.49-3.45 (m, 2 H), 3.30-3.25 (m, 2 H), 2.93-2.75 (m, 4 H), 2.22-2.12 (m, 1 H), 2.03-1.87 (m, 3 H).
MS (ESI) m/z 421.3 (M + H)⁺.
Anal. calcd. for C$_{24}$H$_{28}$N$_4$O$_3$ (+0.4 H$_2$O, 1.0 HCl): C, 62.10; H, 6.47; N, 12.07; O, 11.72, Cl, 7.64. Found: C, 62.42; H, 6.56; N; 11.75.

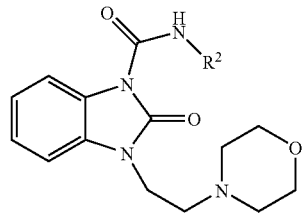

| Example 77 | 3-(2-morpholin-4-ylethyl)-2-oxo-N-[(1R)-1,2,3,4-tetrahydronaphthalen-1-yl]-2,3-dihydro-1H-benzimidazole-1-carboxamide hydrochloride |
|---|---|
| 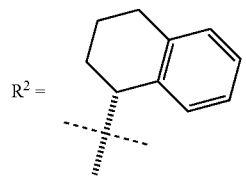<br>$R^2 =$ | $^1$H-NMR (300 MHz, CDCl$_3$) δ 13.90 (bs, 1 H), 8.82 (d, J = 8.1 Hz, 1 H), 8.27 (dd, J = 8.1, 1.2 Hz, 1 H), 7.59-7.56 (m, 1 H), 7.41-7.36 (m, 1 H), 7.32-7.11 (m, 4 H), 5.29-5.23 (m, 1 H), 4.62-4.57 (m, 2 H), 4.29-4.21 (m, 2 H), 4.01-3.98 (m, 2 H), 3.49-3.45 (m, 2 H), 3.30-3.25 (m, 2 H), 2.93-2.75 (m, 4 H), 2.22-2.12 (m, 1 H), 2.03-1.87 (m, 3 H).<br>MS (ESI) m/z 421.3 (M + H)$^+$.<br>Anal. calcd. for C$_{24}$H$_{28}$N$_4$O$_3$ (+0.2 H$_2$O, 1.0 HCl): C, 62.59; H, 6.43; N, 12.16; O, 11.12, Cl, 7.70. Found: C, 62.36; H, 6.59; N; 11.80. |
| Example 78 | N-isoquinolin-1-yl-3-(2-morpholin-4-ylethyl)-2-oxo-2,3-dihydro-1H-benzimidazole-1-carboxamide |
| 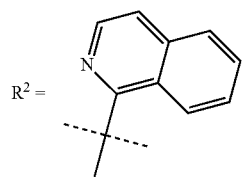<br>$R^2 =$ | $^1$H-NMR (300 MHz, CDCl$_3$) δ 11.97 (s, 1 H), 8.47 (d, J = 5.7 Hz, 1 H), 8.44-8.39 (m, 1 H), 8.23 (d, J = 8.7 Hz, 1 H), 7.88-7.85 (m, 1 H), 7.76-7.65 (m, 2 H), 7.53 (d, J = 5.7 Hz, 1 H), 7.31-7.21 (m, 2 H), 7.14-7.09 (m, 1 H), 4.12 (t, J = 6.6 Hz, 2 H), 3.71-3.68 (m, 4 H), 2.77 (t, J = 6.6 Hz, 2 H), 2.60-2.57 (m, 4 H).<br>MS (ESI) m/z 418.3 (M + H)$^+$.<br>Anal. calcd. for C$_{24}$H$_{23}$N$_5$O$_3$: C, 66.17; H, 5.55; N, 16.78; O, 11.50. Found: C, 66.13; H, 5.56; N; 16.62.<br>IR (KBr)ν$_{max}$ 2827, 1753, 1634, 1547, 1377 cm$^{-1}$.<br>mp 139.0° C. |
| Example 79 | Methyl N-{[4-methoxy-3-(2-morpholin-4-ylethyl)-2-oxo-2,3-dihydro-1H-benzimidazol-1-yl]carbonyl}-3-methyl-L-valinate |
| 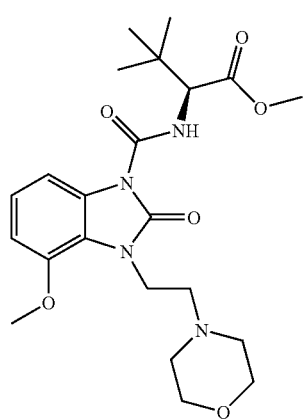 | $^1$H-NMR (300 MHz, CDCl$_3$) δ 9.54 (d, J = 8.4 Hz, 1 H), 7.86 (dd, J = 8.1, 0.6 Hz, 1 H), 7.08 (t, J = 8.1 Hz, 1 H), 6.76 (d, J = 8.1 Hz, 1 H), 4.43 (d, J = 8.4 Hz, 1 H), 4.31-4.17 (m, 2 H), 3.91 (s, 3 H), 3.76 (s, 3 H), 3.67 (t, J = 4.5 Hz, 4 H), 2.75-2.64 (m, 2 H), 2.59-2.50 (m, 4 H), 1.09 (s, 9 H),<br>MS (ESI) m/z 449 (M + H)$^+$.<br>Anal. calcd. for C$_{22}$H$_{32}$N$_4$O$_6$: C, 58.91; H, 7.19; N, 12.49; O, 21.40. Found: C, 58.78; H, 7.12; N; 12.35. |

-continued

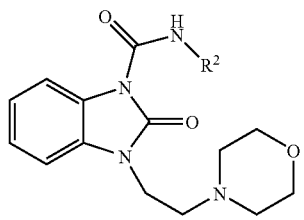

| Example 80 | N-[(1S)-1-(Aminocarbonyl)-2,2-dimethylpropyl]-4-methoxy-3-(2-morpholin-4-ylethyl)-2-oxo-2,3-dihydro-1H-benzimidazole-1-carboxamide |

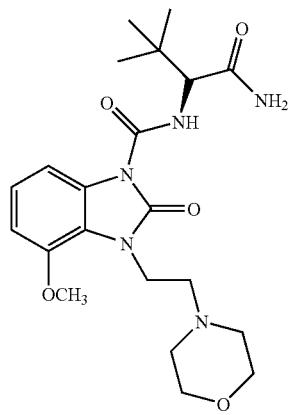

$^1$H-NMR (300 MHz, CDCl3) δ 9.58 (d, J = 7.8 Hz, 1 H), 7.84 (dd, J = 8.4, 0.9 Hz, 1 H), 7.08 (d, J = 8.4 Hz, 1 H),
6.77 (d, J = 8.4 Hz, 2 H), 5.96 (bs, 1 H), 5.66 (bs, 1 H),
4.32-4.15 (m, 3 H), 3.91 (s, 3 H), 3.67 (t, J = 4.5 Hz, 2 H), 2.76-2.62 (m, 2 H),
2.60-2.49 (m, 4 H), 1.14 (s, 9 H).
MS (ESI) m/z 434.4 (M + H)$^+$.
Anal. calcd. for C$_{21}$H$_{31}$N$_5$O$_5$ (+1 H$_2$O): C, 57.94; H, 7.22; N, 16.09; O, 18.74. Found: C, 57.77; H, 7.19; N; 15.72.
mp 210.9° C.

| Example 81 | N-[(1S)-1-(Aminocarbonyl)-2,2-dimethylpropyl]-2-oxo-3-(2-piperidin-1-ylethyl)-2,3-dihydro-1H-benzimidazole-1-carboxamide hydrochloride |

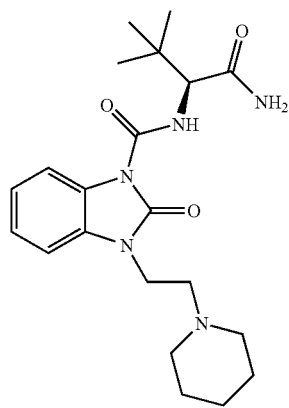

$^1$H-NMR (300 MHz, DMSO-d$_6$) δ 10.51 (bs, 1 H), 9.13 (d, J = 9.0 Hz, 1 H), 8.06 (dd,
J = 7.8, 0.9 Hz, 1 H), 7.70 (bs, 1 H), 7.53 (d, J = 7.8 Hz, 1 H), 7.31-7.16 (m, 3 H),
4.35-4.45 (m, 2 H), 4.27 (d, J = 9.0 Hz, 1 H), 3.70-3.51 (m, 2 H), 3.43-3.31 (m, 2 H),
3.05-2.87 (m, 2 H), 1.88-1.65 (m, 5 H), 1.47-1.30 (m, 1 H), 1.00 (s, 9 H).
MS (ESI) m/z 402.3 (M + H)$^+$.
Anal. calcd. for C$_{21}$H$_{31}$N$_5$O$_3$ (+1.0 H$_2$O, 1.0 HCl): C, 55.32; H, 7.52; N, 15.36; O, 14.04; Cl, 7.78. Found: C, 55.70; H, 7.69; N; 15.30.

| Example 82 | N-{(1S,2S)-1-[(dimethylamino)carbonyl]-2-methylbutyl}-2-oxo-3-(2-piperidin-1-ylethyl)-2,3-dihydro-1H-benzimidazole-1-carboxamide |

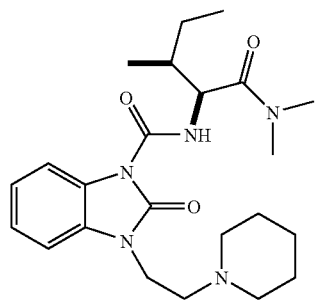

MS (ESI) m/z 430 (M + H)$^+$.
Rt = 1.07 min

-continued

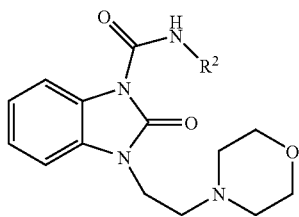

| Example 83 | N-{(1S,2S)-1-[(dimethylamino)carbonyl]-2-methylbutyl}-2-oxo-3-(2-thiomorpholin-4-ylethyl)-2,3-dihydro-1H-benzimidazole-1-carboxamide |

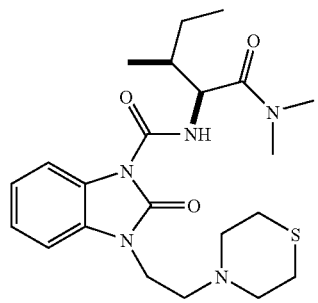

MS (ESI) m/z 448 (M + H)$^+$.
Rt = 1.06 min

| Example 84 | 4-methoxy-3-(2-morpholin-4-ylethyl)-N-1-naphthyl-2-oxo-2,3-dihydro-1H-benzimidazole-1-carboxamide |

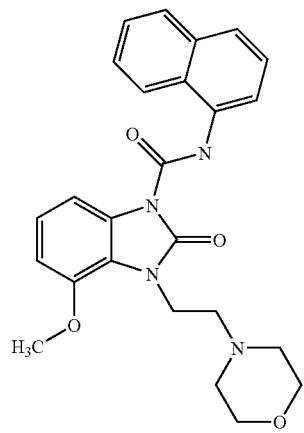

$^1$H-NMR (300 MHz, CDCl$_3$) δ 11.64 (bs, 1 H), 8.25 (dd, J = 7.5, 0.9 Hz, 1 H), 8.16 (d, J = 8.4 Hz, 1 H), 8.03 (dd, J = 8.25, 0.9 Hz, 1 H), 7.90-7.88 (m, 1 H), 7.70 (d, J = 8.4 Hz, 1 H), 7.63-7.50 (m, 3 H), 7.16 (t, J = 8.3 Hz, 1 H), 6.83-6.81 (m, 1 H), 4.34 (t, J = 6.8 Hz, 2 H), 3.94 (s, 3 H), 3.71-3.68 (m, 4 H), 2.75 (t, J = 6.8 Hz, 2 H), 2.60-2.57 (m, 4 H).
MS (ESI) m/z 447.2 (M + H)$^+$.
Anal. calcd. for C$_{25}$H$_{26}$N$_4$O$_4$: C, 67.25; H, 5.87; N, 12.55; O, 14.33. Found: C, 67.30; H, 6.01; N; 12.48.
IR (KBr)ν$_{max}$ 2959, 1734, 1690, 1572, 1387, 1234 cm$^{-1}$.
mp 170.9° C.

| Example 85 | N-1-naphthyl-2-oxo-3-(2-piperidin-1-ylethyl)-2,3-dihydro-1H-benzimidazole-1-carboxamide |

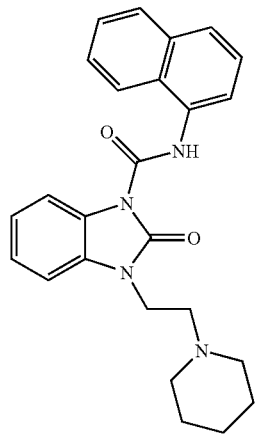

$^1$H-NMR (300 MHz, CDCl$_3$) δ 11.53 (bs, 1 H), 8.36-8.33 (m, 1 H), 8.26 (dd, J = 7.5, 0.9 Hz, 1 H), 8.17 (d, J = 8.7 Hz, 1 H), 7.91-7.88 (m, 1 H), 7.70 (d, J = 8.1 Hz, 1 H), 7.63-7.51 (m, 3 H), 7.30-7.20 (m, 2 H), 7.16-7.13 (m, 1 H), 4.16-4.07 (m, 2 H), 2.77-2.67 (m, 2 H), 2.58-2.46 (m, 4 H), 1.65-1.52 (m, 4 H), 1.50-1.39 (m, 2 H).
MS (ESI) m/z 415.3 (M + H)$^+$.
Anal. calcd. for C$_{25}$H$_{26}$N$_4$O$_2$: C, 72.44; H, 6.32; N, 13.52; O, 7.72. Found: C, 72.51; H, 6.41; N; 13.26.
IR (KBr)ν$_{max}$ 2941, 1734, 1572, 1379, 1261, 1163 cm$^{-1}$.
mp 145.7° C.

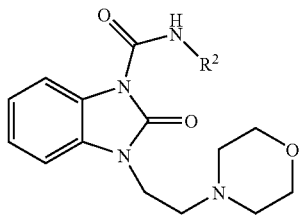

| Example 86 | 3-(2-morpholin-4-ylethyl)-2-oxo-N-(1,2,3,4-tetrahydronaphthalen-1-yl)-2,3-dihydro-1H-imidazo[4,5-b]pyridine-1-carboxamide hydrochloride |
|---|---|
| 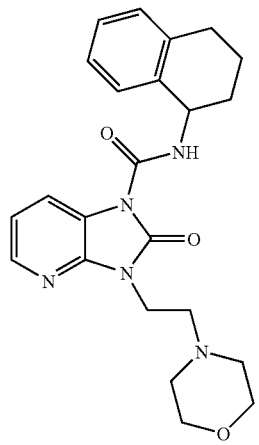 | $^1$H-NMR (300 MHz, CDCl$_3$) δ 13.59 (bs, 1 H), 8.57-8.52 (m, 2 H), 8.13 (d, J = 4.8 Hz, 1 H), 7.45-7.42 (m, 1 H), 7.29-7.12 (m, 3 H), 5.27-5.20 (m, 1 H), 4.63 (bs, 2 H), 4.32-4.22 (m, 2 H), 3.98-3.93 (m, 2 H), 3.74-3.70 (m, 2 H), 3.53 (bs, 2 H), 2.94-2.75 (m, 4 H), 2.25-2.15 (m, 1 H), 2.01-1.89 (m, 3 H). <br> MS (ESI) m/z 422.2 (M + H)$^+$. <br> Anal. calcd. for C$_{23}$H$_{27}$N$_5$O$_2$ (+2.0 HCl): C, 55.87; H, 5.91; N, 14.17; O, 9.71; Cl, 14.34. Found: C, 55.87; H, 5.99; N; 14.23. <br> IR (KBr)ν$_{max}$ 1736, 1535, 1394 cm$^{-1}$. |
| Example 87 | 4-methyl-3-(2-morpholin-4-ylethyl)-2-oxo-N-(1,2,3,4-tetrahydronaphthalen-1-yl)-2,3-dihydro-1H-benzimidazole-1-carboxamide hydrochloride |
| 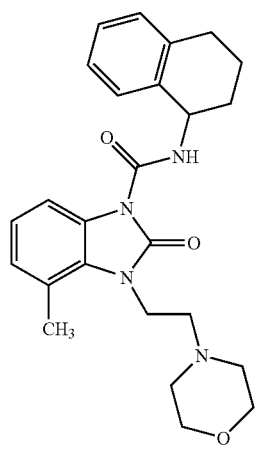 | $^1$H-NMR (300 MHz, CDCl$_3$) δ 14.98 (bs, 1 H), 8.94-8.92 (m, 1 H), 8.23 (d, J = 8.1 Hz, 1 H), 7.40-7.37 (m, 1 H), 7.21-7.17 (m, 2 H), 7.15-7.10 (m, 2 H), 7.01 (d, J = 7.2 Hz, 1 H), 5.29-5.23 (m, 1 H), 4.80-4.68 (m, 2 H), 4.34-4.26 (m, 2 H), 4.01-3.97 (m, 2 H), 3.60-3.48 (m, 2 H), 3.30-3.15 (m, 2 H), 3.05-2.90 (m, 2 H), 2.88-2.81 (m, 1 H), <br> 2.72 (s, 3 H), 2.19-2.13 (m, 1 H), 2.02-1.89 (m, 4 H). <br> MS (ESI) m/z 435.1 (M + H)$^+$. <br> Anal. calcd. for C$_{25}$H$_{30}$N$_4$O$_3$ (+1.0 HCl): C, 63.75; H, 6.63; N, 11.90; O, 10.19; Cl, 7.53. Found: C, 63.42; H, 6.64; N; 11.79. <br> IR (KBr)ν$_{max}$ 1724, 1537, 1452 cm$^{-1}$. |

-continued

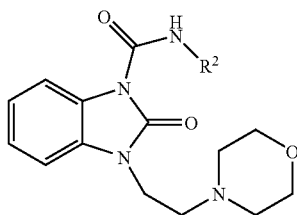

Example 88

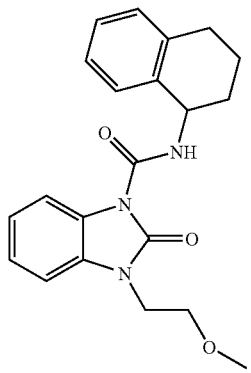

3-(2-methoxyethyl)-2-oxo-N-(1,2,3,4-tetrahydronaphthalen-1-yl)-2,3-dihydro-1H-benzimidazole-1-carboxamide $^1$H-NMR (300 MHz, CDCl$_3$) δ 9.07 (d, J = 7.5 Hz, 1 H), 8.29-8.26 (m, 1 H), 7.43-7.40 (m, 1 H), 7.28-7.10 (m, 6 H), 5.30-5.24 (m, 1 H), 4.03 (t, J = 5.4 Hz, 2 H), 3.66 (t, J = 5.4 Hz, 2 H), 3.32 (s, 3 H), 2.93-2.74 (m, 2 H), 2.21-2.11 (m, 1 H), 2.05-1.87 (m, 3 H).
MS (ESI) m/z 366.1 (M + H)$^+$.
Anal. calcd. for C$_{21}$H$_{23}$N$_3$O$_3$: C, 69.02; H, 6.34; N, 11.50; O, 13.13. Found: C, 69.08; H, 6.52; N; 11.51.
IR (KBr)ν$_{max}$ 1726, 1520, 1383, 1171 cm$^{-1}$.
mp 115.6° C.

Example 89

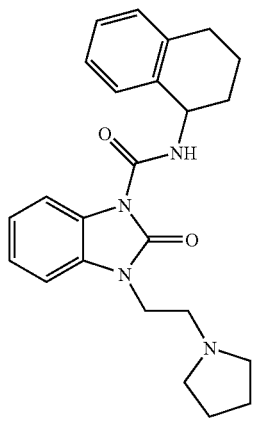

2-oxo-3-(2-pyrrolidin-1-ylethyl)-N-(1,2,3,4-tetrahydronaphthalen-1-yl)-2,3-dihydro-1H-benzimidazole-1-carboxamidehydrochloride $^1$H-NMR (300 MHz, CDCl$_3$) δ 13.19 (bs, 1 H), 8.84 (d, J = 8.4 Hz, 1 H), 8.27 (dd, J = 7.8, 0.9 Hz, 1 H), 7.58 (d, J = 7.2 Hz, 1 H), 7.41-7.38 (m, 1 H), 7.32-7.11 (m, 4 H), 5.29-5.23 (m, 1 H), 4.55-4.51 (m, 2 H), 3.78 (bs, 2 H), 3.89 (t, J = 7.2 Hz, 2 H), 2.91-2.77 (m, 4 H), 2.21-2.13 (m, 4 H), 2.03-1.71 (m, 4 H).
MS (ESI) m/z 405.2 (M + H)$^+$.
Anal. calcd. for C$_{24}$H$_{28}$N$_4$O$_2$ (+1.0 HCl, 0.3 H$_2$O): C, 64.58; H, 6.68; N, 12.55; O, 8.24; Cl, 7.94. Found: C, 64.67; H, 7.08; N; 12.56.
IR (KBr)ν$_{max}$ 1728, 1533, 1489, 1383 cm$^{-1}$.
mp 165.6° C.

Example 90

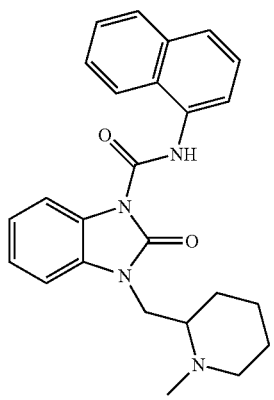

3-[(1-Methylpiperidin-2-yl)methyl]-N-1-naphthyl-2-oxo-2,3-dihydro-1H-benzimidazole-1-carboxamide hydrochloride $^1$H-NMR (300 MHz, CDCl$_3$) δ 12.98 (bs, 1 H), 11.24 (s, 1 H), 8.33 (dd, J = 7.8, 0.9
Hz, 1 H), 8.25 (dd, J = 7.8, 0.9 Hz, 1 H), 8.11 (d, J = 8.7 Hz, 1 H), 7.92-7.89 (m, 1 H),
7.73 (d, J = 8.1 Hz, 1 H), 7.63-7.52 (m, 4 H), 7.37-7.24 (m, 2 H), 4.72 (dd J = 14.7, 5.1 Hz, 1 H), 4.60-4.52 (m, 1 H), 3.57-3.45 (m, 2 H), 2.97
(s, 3 H), 2.90-2.81 (m, 1 H),
2.33-2.21 (m, 2 H), 2.01-1.86 (m, 3 H), 1.51-1.43 (m, 1 H).
MS (ESI) m/z 415.1 (M + H)$^+$.
Anal. calcd. for C$_{25}$H$_{26}$N$_4$O$_2$
(+0.7 H$_2$O, 1.0 HCl, 0.2 C$_4$H$_8$O$_2$) C, 64.40; H, 6.28; N,
11.64; O, 10.31; Cl, 7.37. Found: C, 64.56; H, 6.06; N; 11.32.
IR (KBr)ν$_{max}$ 1740, 1570, 1383 cm$^{-1}$.

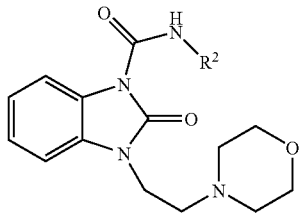

Following Examples 91 to 92 were prepared according to the procedure described in Example 3.

| Example 91 | N-[(1S,2S)-2-Methyl-1-(morpholin-4-ylcarbonyl)butyl]-3-(2-morpholin-4-ylethyl)-2-oxo-2,3-dihydro-1H-benzimidazole-1-carboxamide hydrochloride |

$^1$H-NMR (300 MHz, CDCl$_3$) δ 9.23 (d, J = 8.9 Hz, 1 H), 8.15 (d, J = 7.8 Hz, 1 H), 7.60-7.48 (m, 1 H), 7.31-7.17 (m, 2 H), 4.87 (dd, J = 8.37, 6.21 Hz, 1 H), 4.75-4.45 (m, 2 H), 4.35-3.95 (m, 4 H), 3.80-3.25 (m, 12 H), 3.07-2.87 (m, 2 H), 1.92-1.83 (m, 1 H), 1.70-1.55 (m, 1 H), 1.28-1.17 (m, 1 H), 1.04 (d, J = 6.75 Hz, 3 H), 0.94 (t, J = 7.3 Hz, 3 H).
MS (ESI) m/z 474 (M + H)$^+$.
Anal. calcd. for C$_{24}$H$_{35}$N$_5$O$_5$ (+1 H$_2$O, 1 HCl): C, 54.59; H, 7.25; N, 13.26; O, 18.18, Cl, 6.71. Found: C, 54.52; H, 7.16; N; 12.86.

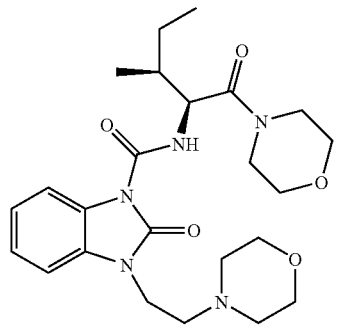

| Example 92 | N-[(1S)-2,2-Dimethyl-1-(pyrrolidin-1-ylcarbonyl)propyl]-3-(2-morpholin-4-ylethyl)-2-oxo-2,3-dihydro-1H-benzimidazole-1-carboxamide hydrochloride |

$^1$H-NMR (300 MHz, DMSO-d$_6$) δ 11.46 (bs, 1 H), 9.18 (d, J = 9.0 Hz, 1 H), 8.05 (d, J = 7.8 Hz, 1 H), 7.53 (d, J = 7.5 Hz, 1 H), 7.34-7.17 (m, 2 H), 4.60 (d, J = 9.0 Hz, 1 H), 4.40 (t, J = 6.3 Hz, 2 H), 4.06-3.98 (m, 2 H), 3.84-3.72 (m, 2 H), 3.70-3.28 (m, 12 H), 3.26-3.15 (m, 2 H), 1.95-1.87 (m, 2 H), 1.83-1.75 (m, 2 H), 1.02 (s, 9 H).
MS (ESI) m/z 458 (M + H)$^+$.
Anal. calcd. for C$_{24}$H$_{35}$N$_5$O$_4$ (+1 H$_2$O, 1 HCl): C, 56.30; H, 7.48; N, 13.68; O, 15.62, Cl, 6.92. Found: C, 56.53; H, 7.60; N; 13.35.

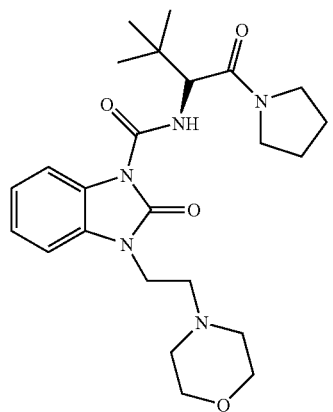

Example 93

N-[(1S)-2,2-dimethyl-(2-methyl-2H-tetrazol-5-yl)propyl]-3-(2-morpholin-4-ylethyl)-2-oxo-2,3-dihydro-1H-benzimidazole-1-carboxamide

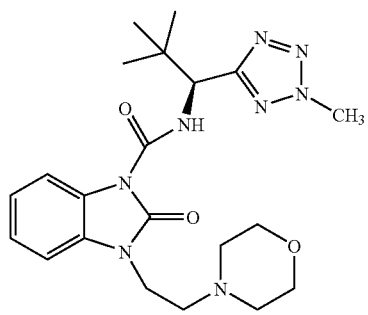

Step 1. benzyl [(1S)-2,2-dimethyl-1-(2H-tetrazol-5-yl)propyl]carbamate

The title compound was prepared according to the procedure described in the literature (Demko. Z. P.; Sharpless, K. B. *Org. Lett.* 2002, 4, 2525-2527.) from benzyl [(1S)-1-(aminocarbonyl)-2,2-dimethylpropyl]carbamate (Step 1 of Example 4).

MS (ESI) m/z 290 (M+H)$^+$, 288 (M−H)$^−$.

Step 2. benzyl [(1S)-2,2-dimethyl-1-(2-methyl-2H-tetrazol-5-yl)propyl]carbamate and benzyl [(1S)-2,2-dimethyl-1-(1-methyl-1H-tetrazol-5-yl)propyl]carbamate To a suspension of benzyl [(1S)-2,2-dimethyl-1-(2H-tetrazol-5-yl)propyl]carbamate (280 mg, 0.96 mmol), potassium carbonate (660 mg, 4.8 mmol) and methyl iodide (0.24 mL, 3.8 mmol) in acetone (5 mL) was stirred at 0° C. for 10 min and warmed to rt. After 4 h, the mixture was filtered and concentrated. The residue was purified by column chromatography on silica gel eluting with hexane/ethyl acetate (8/1-4/1-1/1) to afford 166 mg (57%) of benzyl [(1S)-2,2-dimethyl-1-(2-methyl-2H-tetrazol-5-yl)propyl]carbamate and 82 mg (28%) of benzyl [(1S)-2,2-dimethyl-1-(1-methyl-1H-tetrazol-5-yl)propyl]carbamate.

benzyl [(1S)-2,2-dimethyl-1-(2-methyl-2H-tetrazol-5-yl)propyl]carbamate $^1$H-NMR (300 MHz, CDCl$_3$) δ 7.40-7.28 (m, 5H), 5.59 (d, J=9.3 Hz, 1H), 5.12 (d, J=12.3 Hz, 1H), 5.06 (d, J=12.3 Hz, 1H), 5.00 (d, J=9.3 Hz, 1H), 4.32 (s, 3H), 0.97 (s, 9H).

MS (ESI) m/z 304 (M+H)$^+$.

benzyl [(1S)-2,2-dimethyl-1-(1-methyl-1H-tetrazol-5-yl)propyl]carbamate $^1$H-NMR (300 MHz, CDCl$_3$) δ 7.40-7.28 (m, 5H), 5.55 (d, J=9.6 Hz, 1H), 5.10 (d, J=12.6 Hz, 1H), 5.02 (d, J=12.6 Hz, 1H), 4.84 (d, J=9.6 Hz, 1H), 4.13 (s, 3H), 1.05 (s, 9H).

MS (ESI) m/z 304 (M+H)$^+$.

Step 3. N-[(1S)-2,2-dimethyl-1-(2-methyl-2H-tetrazol-5-yl)propyl]-3-(2-morpholin-4-ylethyl)-2-oxo-2,3-dihydro-1H-benzimidazole-1-carboxamide The titled compound was prepared according to the procedure described in Step 4 of example 1 from (1S)-2,2-dimethyl-1-(2-methyl-2H-tetrazol-5-yl)propan-1-amine which was prepared from benzyl [(1S)-2,2-dimethyl-1-(2-methyl-2H-tetrazol-5-yl)propyl]carbamate according to the procedure described in step 2 of example 4.

$^1$H-NMR (300 MHz, CDCl$_3$) δ 13.9 (bs, 1H), 9.55-9.32 (m, 1H), 8.22-8.01 (m, 1H), 7.68-7.43 (m, 1H), 7.35-7.05 (m, 1H), 5.24-5.15 (m, 1H), 4.78-4.47 (m, 2H), 4.40-3.85 (m, 7H), 3.62-3.18 (m, 4H), 3.12-2.80 (m, 2H), 1.08 (s, 9H).

MS (ESI) m/z 443 (M+H)$^+$.

Anal. calcd. for C$_{21}$H$_{30}$N$_8$O$_3$ (+0.5H$_2$O, 1.0HCl, 0.5 C$_4$H$_8$O$_2$): C, 51.92; H, 6.82; N, 21.06; O, 13.53; Cl, 6.66. Found: C, 51.73; H, 6.79; N, 21.20.

Example 94

N-[(1S)-2,2-dimethyl-1-(1-methyl-1H-tetrazol-5-yl)propyl]-3-(2-morpholin-4-ylethyl)-2-oxo-2,3-dihydro-1H-benzimidazole-1-carboxamide

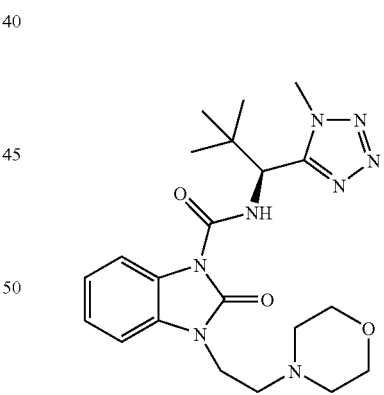

The titled compound was prepared according to the procedure described in Step 2 of Example 12 from (1S)-2,2-dimethyl-1-(1-methyl-1H-tetrazol-5-yl)propan-1-amine which was prepared from benzyl [(1S)-2,2-dimethyl-1-(1-methyl-1H-tetrazol-5-yl)propyl]carbamate according to the procedure described in Step 2 of Example 4.

$^1$H-NMR (300 MHz, CDCl$_3$) δ 9.72 (d, J=8.1 Hz, 1H), 8.06 (d, J=7.2 Hz, 1H), 7.23-7.00 (m, 4H), 5.09 (d, J=8.1 Hz, 1H), 4.22 (s, 3H), 4.07-3.95 (m, 2H), 3.73-3.61 (m, 4H), 2.75-2.44 (m, 6H), 1.17 (s, 9H).

MS (ESI) m/z 443 (M+H)$^+$.

Example 95

N-[(1S)-8-(aminocarbonyl)-2,2-dimethylpropyl]-3-(2-methyl-2-methylpropyl)-2-oxo-2,3-dihydro-1H-benzimidazole-1-carboxamide

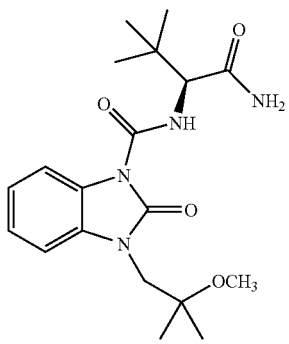

Step 1. 2-methoxy-2-methylpropan-1-amine

To a suspension of lithium aluminum hydride (2.1 g, 55 mmol) and diethyl ether (30 mL) at 0° C. was added a solution of 2-methoxy-2-methylpropanenitrile (prepared from 2.5 g (29 mmol) of 2-hydroxy-2-methylpropanenitrile according to the procedure in the literature (U.S. Pat. No. 4,864,051)) in diethyl ether (20 mL). The mixture was refluxed for 7 h. Then the reaction mixture was quenched by addition of water (2.1 mL), 15% NaOH (2.1 mL) and water (6.3 mL) at 0° C. and stirred at rt for 14 h. The mixture was filtered and concentrated in vacuo to give crude material (1.5 g).

$^1$H-NMR (300 MHz, CDCl$_3$) δ 3.20 (s, 3H), 2.65 (s, 2H), 1.14 (s, 9H).

Step 2. 1-(2-methoxy-2-methylpropyl)-1,3-dihydro-2H-benzimidazol-2-one

The title compound was prepared according to the procedure described in Steps 1, 2 and 3 of Example 1 from 2-methoxy-2-methylpropan-1-amine.

MS (ESI) m/z 221 (M+H)$^+$, 219 (M−H)$^−$.

Step 3. N-[(1S)-1-(aminocarbonyl)-2,2-dimethylpropyl]-3-(2-methyl-2-methylpropyl)-2-oxo-2,3-dihydro-1H-benzimidazole-1-carboxamide The title compound was prepared according to the procedure described in Step 2 of Example 12 without recrystallization.

$^1$H-NMR (300 MHz, CDCl$_3$) δ 9.49 (d, J=8.1 Hz, 1H), 8.16-8.11 (m, 1H), 7.31-7.23 (m, 1H), 7.22-7.10 (m, 2H), 5.97 (bs 1H), 5.65 (bs, 1H), 4.24 (d, J=8.1 Hz, 1H), 3.90 (d, J=14.4 Hz, 1H), 3.85 (d, J=14.4 Hz, 1H), 3.20 (s, 3H), 1.27 (s, 3H), 1.26 (s, 3H), 1.15 (s, 9H).

MS (ESI) m/z 377 (M+H)$^+$.

Example 96

N-[(1S)-1-(aminocarbonyl)-2,2-dimethylpropyl]-3-(2-hydroxy-2-methylpropyl)-2-oxo-2,3-dihydro-1H-benzimidazole-1-carboxamide

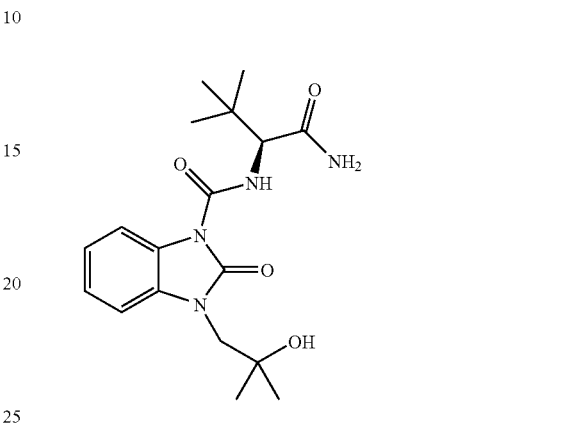

Step 1. 1-amino-2-methylpropan-2-ol hydrochloride

The title compound was prepared according to the procedure described in Step 1 of Example 95 from 2-hydroxy-2-methylpropanenitrile.

$^1$H-NMR (300 MHz, CDCl$_3$, the value of free form of the title compound) δ 4.39-3.96 (s, 1H), 2.61 (s, 2H), 1.17 (s, 6H).

Step 2. 1-(2-hydroxy-2-methylpropyl)-1,3-dihydro-2H-benzimidazol-2-one

The title compound was prepared according to the procedure described in Steps 1, 2 and 3 of Example 1 from 1-amino-2-methylpropan-2-ol hydrochloride.

$^1$H-NMR (300 MHz, CDCl$_3$) δ 10.43 (bs, 1H), 7.13-7.04 (m, 4H), 3.92 (s, 2H), 3.63 (s, 1H), 1.33 (s 6H).

MS (ESI) m/z 207 (M+H)$^+$, 205 (M−H)$^−$.

Step 3 N-[(1S)-1-(aminocarbonyl)-2,2-dimethylpropyl]-3-(2-hydroxy-2-methylpropyl)-2-oxo-2,3-dihydro-1H-benzimidazole-1-carboxamide The title compound was prepared according to the procedure described in Step 2 of Example 12.

$^1$H-NMR (300 MHz, CDCl$_3$) δ 9.40 (d, J=8.1 Hz, 1H), 8.21-8.15 (m, 1H), 7.22-7.15 (m, 3H), 5.84 (bs 1H), 5.54 (bs, 1H), 4.22 (d, J=8.1 Hz, 1H), 2.13 (s, 2H), 2.36 (s, 1H), 1.35 (s, 6H), 1.15 (s, 9H).

MS (ESI) m/z 363 (M+H)$^+$.

Anal. calcd. for $C_{18}H_{26}N_4O_4$ (+0.1H$_2$O): C, 59.36; H, 7.25; N, 15.38; O, 18.01. Found: C, 59.45; H, 7.25; N, 15.00.

Example 97

N-[(1S)-1-cyano-2,2-dimethylpropyl]-3-(2-morpholin-4-ylethyl)-2-oxo-2,3-dihydro-1H-benzimidazole-1-carboxamide

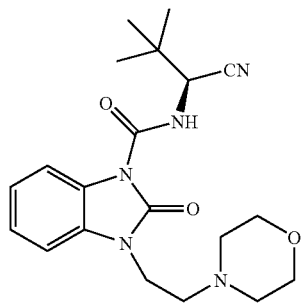

Step 1. benzyl [(1S)-1-cyano-2,2-dimethylpropyl]carbamate

The title compound was prepared according to the procedure described in the literature (Demko. Z. P.; Sharpless, K. B. *Org. Lett.* 2002, 4, 2525-2527.) from benzyl [(1S)-1-(aminocarbonyl)-2,2-dimethylpropyl]carbamate (Step 1 of Example 4).

MS (ESI) m/z 247 (M+H)$^+$.

Step 2. N-[(1S)-1-cyano-2,2-dimethylpropyl]-3-(2-morpholin-4-ylethyl)-2-oxo-2,3-dihydro-1H-benzimidazole-1-carboxamide The title compound was prepared according to the procedure described in Step 2 of Example 12 from (2S)-2-amino-3,3-dimethylbutanenitrile which was prepared from benzyl [(1S)-1-cyano-2,2-dimethylpropyl]carbamate according to the procedure described in Step 2 of Example 4.

$^1$H-NMR (300 MHz, CDCl$_3$) δ 9.45 (d, J=9.0 Hz, 1H), 8.20-8.16 (m, 1H), 7.28-7.18 (m, 2H), 7.09-7.03 (m 1H), 4.77 (d, J=9.0 Hz, 1H), 4.04-3.98 (m, 2H), 3.70-3.62 (m, 4H), 2.77-2.63 (m, 2H), 2.60-2.48 (m, 4H), 1.18 (s, 9H).

MS (ESI) m/z 386 (M+H)$^+$.

Anal. calcd. for C$_{20}$H$_{27}$N$_5$O$_3$: C, 62.32; H, 7.06; N, 18.17; O, 12.45. Found: C, 61.99; H, 7.01; N, 17.96.

Example 98

N-[(1S)-1-(aminocarbonyl)-2,2-dimethylpropyl]-5-methyl-3-(2-morpholin-4-ylethyl)-2-oxo-2,3-dihydro-1H-imidazo[4,5-b]pyridine-1-carboxamide

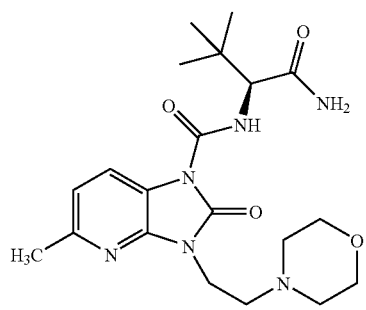

Step 1. 5-methyl-3-(2-morpholin-4-ylethyl)-1,3-dihydro-2H-imidazo[4 5-b]pyridin-2-one The title compound was prepared from 2-chloro-3-nitro-6-picoline according to the procedure described in Steps 1, 2 and 3 of Example 1.

$^1$H-NMR (300 MHz, CDCl$_3$) δ 9.94 (bs, 1H), 7.12 (d, J=7.5 Hz, 1H), 6.80 (d, J=7.5 Hz, 1H), 4.18-4.05 (m, 2H), 3.70-3.55 (m, 4H), 2.83-2.71 (m, 2H), 2.65-2.53 (m, 4H), 2.50 (s, 3H).

MS (ESI) m/z 263 (M+H)$^+$, 261 (M–H)$^−$.

Step 2. N-[(1S)-(aminocarbonyl)-2,2-dimethylpropyl]-5-methyl-3-(2-morpholin-4-ylethyl)-2-oxo-2,3-dihydro-1H-imidazo[4,5-b]pyridine-1-carboxamide (PF-03407918-01)

The title compound was prepared from 5-methyl-3-(2-morpholin-4-ylethyl)-1,3-dihydro-2H-imidazo[4,5-b]pyridin-2-one and L-tert-leucinamide according to the procedure described in Step 4 of Example 1.

$^1$H-NMR (300 MHz, DMSO-d$_6$) δ 11.29 (bs, 1H), 8.93 (d, J=8.7 Hz, 1H), 8.07 (d, J=7.8 Hz, 1H), 7.73 (bs, 1H), 7.26 (bs, 1H), 7.06 (d, J=7.8 Hz, 1H), 4.38-4.22 (m, 3H), 4.06-3.59 (m, 8H), 3.25-3.08 (m, 2H), 2.48 (s, 3H), 0.99 (s, 9H).

MS (ESI) m/z 419 (M+H)$^+$.

Anal. calcd. for C$_{20}$H$_{30}$N$_6$O$_4$ (0.6H$_2$O, 1.0HCl, 0.1 C$_4$H$_8$O$_2$): C, 51.63; H, 7.01; N, 17.71; O, 16.18; Cl, 7.47. Found: C, 51.88; H, 7.14; N, 17.48.

Example 99

N-[(1S)-1-(aminocarbonyl)-2-methylpropyl]-5-methyl-3-(2-morpholin-4-ylethyl)-2-oxo-2,3-dihydro-1H-imidazo[4,5-b]pyridine-1-carboxamide

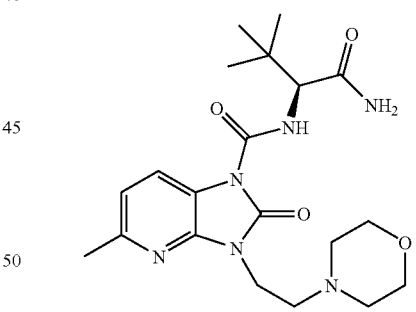

The title compound was prepared from 5-methyl-3-(2-morpholin-4-ylethyl)-1,3-dihydro-2H-imidazo[4,5-b]pyridin-2-one and L-valinamide hydrochloride according to the procedure described in Step 4 of Example 1.

$^1$H-NMR (300 MHz, DMSO-d$_6$) δ 11.22 (bs, 1H), 8.82 (d, J=8.7 Hz, 1H), 8.07 (d, J=7.8 Hz, 1H), 7.73 (bs, 1H), 7.28 (bs, 1H), 7.07 (d, J=7.8 Hz, 1H), 4.38-4.26 (m, 3H), 4.06-3.60 (m, 8H), 3.27-3.08 (m, 2H), 2.48 (s, 3H), 2.19-2.08 (m, 1H), 0.96 (d, J=7.2 Hz, 3H), 0.89 (d, J=6.6 Hz, 3H).

MS (ESI) m/z 405 (M+H)$^+$.

Anal. calcd. for C$_{19}$H$_{28}$N$_6$O$_4$ (0.5H$_2$O, 1.0HCl, 0.1 C$_4$H$_8$O$_2$): C, 50.79; H, 6.77; N, 18.32; O, 16.39; Cl, 7.73. Found: C, 50.46; H, 6.90; N, 17.93.

Example 100

N-[(1S)-2,2-dimethyl-1-(3-methyl-1,2,4-oxadiazol-5-yl)propyl]-3-[2-(4-morpholinyl)ethyl]-2-oxo-2,3-dihydro-1H-benzimidazole-1-carboxamide

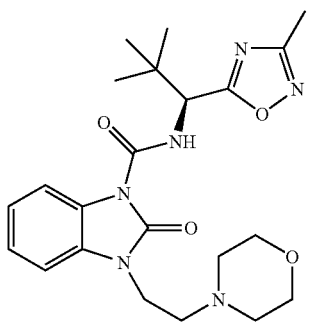

Step 1. E,Z mixture of N-[(1S)-1-[({[1-aminoethylidene]amino}oxy)carbonyl]-2,2-dimethylpropyl]-3-[2-(4-morpholinyl)ethyl]-2-oxo-2,3-dihydro-1H-benzimidazole-1-carboxamide To a solution of N-({3-[2-(4-morpholinyl)ethyl]-oxo-2,3-dihydro-1H-benzimidazol-1-yl}carbonyl)-L-tert-leucine (prepared according to the procedure described in step 1 of example 3 from methyl L-tert-leucinate hydrochloride) (0.18 g, 0.45 mmol) in DMF (1 mL) were added a solution of N-hydroxyethanimidamide (37 mg, 0.50 mmol, Hamze, A.; Hernandez, J.-F.; Fulcrand, P.; Martinez, J. *J. Org. Chem.* 2003, 68, 7316-7321.) in DMF (1 mL), triethylamine (0.26 mL, 1.8 mmol), HOBt (83 mg, 0.54 mmol) and WSC (0.10 g, 0.54 mmol) at rt. After 9 h, to this mixture were added N-hydroxyethanimidamide (20 mg, 0.26 mmol), triethylamine (0.10 mL, 0.70 mmol), HOBt (10 mg, 0.06 mmol) and WSC (20 mg, 0.10 mmol). After 13 h, the reaction was quenched by addition of sat. aq. sodium bicarbonate (10 mL) and extracted with ethyl acetate (20 mL×2). The combined organic layers were washed with water (10 mL×2), brine (20 mL) and dried over sodium sulfate, filtered and concentrated. The residue was purified by column chromatography on silica gel eluting with dichloromethane/methanol (10/1) to afford 0.12 g (57%) of the title compound.

MS (ESI) m/z 461 (M+H)$^+$.

Step 2. N-[(1S)-2,2-dimethyl-1-(3-methyl-1,2,4-oxadiazol-5-yl)propyl]-3-[2-(4-morpholinyl)ethyl]-2-oxo-2,3-dihydro-1H-benzimidazole-1-carboxamide To a solution of N-{(1S)-1-[({[aminoethylidene]amino}oxy)carbonyl]-2,2-dimethylpropyl}-3-[2-(4-morpholinyl)ethyl]-2-oxo-2,3-dihydro-1H-benzimidazole-1-carboxamide (0.11 g, 0.24 mmol) in toluene (5 mL) was added p-toluenesulfonic acid monohydrate (4 mg, 0.02 mmol) and the mixture was refluxed for 6 h. Then the reaction was cooled to rt and quenched by addition of water (10 mL) and extracted with ethyl acetate (20 mL×2). The combined organic layers were washed with brine (20 mL) and dried over sodium sulfate, filtered and concentrated. The residue was purified by preparative TLC eluting with dichloromethane/methanol (10/1) to afford 62 mg (58%) of the title compound. The subsequent recrystallization from ethyl acetate and hexane followed by filtration gave 48 mg of the title compound as white solid.

$^1$H-NMR (300 MHz, CDCl$_3$) δ9.68 (d, J=8.1 Hz, 1H), 8.15 (d, J=8.1 Hz, 1H), 7.30-7.11 (m, 2H), 7.08-7.01 (m, 1H), 5.18 (d, J=8.1 Hz, 1H), 4.09-4.00 (m, 2H), 3.72-3.63 (m, 4H), 2.75-2.67 (m, 2H), 2.61-2.48 (m, 4H), 2.41 (s, 3H), 1.12 (s, 9H).

MS (ESI) m/z 443 (M+H)$^+$.

Anal. calcd. for $C_{22}H_{30}N_6O_4$ (+0.2H$_2$O): C, 59.23; H, 6.87; N, 18.84; O, 15.06. Found: C, 59.14; H, 7.00; N, 18.50.

Example 101

N-[(1S)-1-(aminocarbonyl)-2,2-dimethylpropyl]-3-(3-hydroxy-3-methylbutyl)-2-oxo-2,3-dihydro-1H-benzimidazole-1-carboxamide

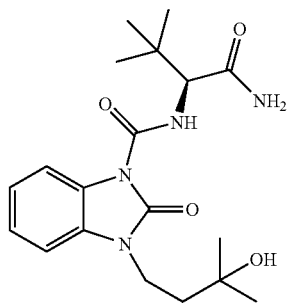

Step 1. 3-hydroxy-3-methylbutanenitrile

To a solution of 1-chloro-2-methylpropan-2-ol (17 g, 0.16 mol) in ethanol (320 mL) and water (55 mL) was added sodium cyanide (9.4 g, 0.19 mol) and the mixture was refluxed. After 3 h, the mixture was cooled to rt and concentrated in vacuo. To the residue was added water and extracted with ethyl acetate. The combined organic layers were dried over magnesium sulfate and concentrated to give 14 g (90%) of the title compound.

$^1$H-NMR (300 MHz, CDCl$_3$) δ 2.54 (s, 2H), 2.03 (s, 1H), 1.42 (s, 6H).

Step 2. 4-amino-2-methyl-2-butanol

To a solution of 3-hydroxy-3-methylbutanenitrile (16 g, 0.16 mol) in THF (350 mL) was added lithium aluminumhydride (12 g, 0.33 mol) slowly at 0° C. and the mixture was stirred for 4 h at 50° C. After cooling to 0° C., to the mixture were added sodium sulfate decahydrate and potassium fluoride. The mixture was stirred for 30 min at rt and filtered through a pad of celite. The filtrate was concentrated in vacuo to give 14 g (84%) of the title compound.

$^1$H-NMR (300 MHz, CDCl$_3$) δ 3.03 (t, J=6.8 Hz, 2H), 1.58 (t, J=6.8 Hz, 2H), 1.24 (s, 6H).

Step 3. 2-methyl-4-[(2-nitrophenyl)amino]-2-butanol

A solution of 1-fluoro-2-nitrobenzene (1.9 mL, 18 mmol), 4-amino-2-methyl-2-butanol (1.6 g, 15 mmol) and triethylamine (6.4 mL, 46 mmol) in THF (30 mL) was refluxed for 8 h. Then the reaction was quenched by addition of water (50 mL) and extracted with ethyl acetate (50 mL×2). The combined organic layers were washed with brine (50 mL) and dried over sodium sulfate, filtered and concentrated. The residue was purified by column chromatography on silica gel eluting with hexane/ethyl acetate (5/1-2/1) to afford 2.8 g (82%) of the title compound.

MS (ESI) m/z 225 (M+H)$^+$.

Step 4.
4-[(2-aminophenyl)amino]-2-methyl-2-butanol

The title compound was prepared according to the procedure described in step 2 of example 1 from 2-methyl-4-[(2-nitrophenyl)amino]-2-butanol.

MS (ESI) m/z 195 (M+H)$^+$.

Step 5. 1-(3-hydroxy-3-methylbutyl)-1,3-dihydro-2H-benzimidazol-2-one

The title compound was prepared according to the procedure described in step 3 of example 1 from 4-[(2-aminophenyl)amino]-2-methyl-2-butanol.

MS (ESI) m/z 221 (M+H)$^+$.

Step 6. N-[(1S)-1-(aminocarbonyl)-2,2-dimethylpropyl]-3-(3-hydroxy-3-methylbutyl)-2-oxo-2,3-dihydro-1H-benzimidazole-1-carboxamide To a solution of 1-(3-hydroxy-3-methylbutyl)-1,3-dihydro-2H-benzimidazol-2-one (0.25 g, 1.1 mmol) in 1,2-dichloroethane (30 mL) were added triethylamine (0.52 mL, 3.7 mmol) and 4-nitrophenyl chloroformate (0.27 g, 1.4 mmol) at 0° C. and the mixture was stirred for 4 h at rt. Then to this mixture was added a mixture of L-tert-leucinamide (0.18 g, 1.4 mmol) in 1,2-dichloroethane (5 mL) at 0° C. and stirred at rt. After 14 h, the reaction was quenched by addition of water (50 mL) and filtered and washed with water (30 mL) and dichloromethane (30 mL). The obtained solid was suspended in water (50 mL) and filtered. This procedure was repeated twice followed by recrystallization from methanol. The obtained solid was suspended in water (50 mL) again and filtered and this procedure was repeated twice. Then the solid was dissolved in methanol/dichloromethane and filtered and concentrated in vacuo. The obtained solid was then recrystallized from acetone to give 0.14 g (33%) of the title compound.

$^1$H-NMR (300 MHz, DMSO-d$_6$) δ 9.21 (d, J=9.0 Hz, 1H), 8.03 (d, J=7.2 Hz, 1H), 7.65 (bs, 1H), 7.25-7.12 (m, 4H), 4.50 (s, 1H), 4.33 (d, J=9.0 Hz, 1H), 3.96-3.93 (m, 2H), 1.77-1.71 (m, 2H), 1.17 (s, 6H), 0.98 (s, 9H).

MS (ESI) m/z 377 (M+H)$^+$.

Anal. calcd. for $C_{19}H_{28}N_4O_4$: C, 60.62; H, 7.50; N, 14.88; O, 17.00. Found: C, 60.46; H, 7.51; N, 14.59.

mp 247.7° C.

$[\alpha]_D^{23}$ +29.1 (c 0.11, methanol).

>99% ee

Example 102

N-{(1S)-1-[(dimethylamino)carbonyl]-2,2-dimethylpropyl}-4-methyl-3-[2-(methylthio)ethyl]-2-oxo-2,3-dihydro-1H-benzimidazole-1-carboxamide

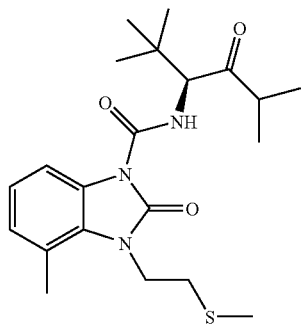

Step 1.
2-methyl-N-[2-(methylthio)ethyl]-6-nitroaniline

A mixture of 2-chloro-3-nitrotoluene (1.3 g, 7.3 mmol), 2-(methylthio)ethylamine (1.4 mL, 15 mmol) and N,N-diisopropylethylamine (5.0 mL, 29 mmol) in 1-methyl-2-pyrrolidinone (3.7 mL) was heated to 220° C. by microwave for 1 h. The mixture was diluted with ethyl acetate (0.10 L) and washed with water (50 mL×2), brine (50 mL), dried over sodium sulfate, filtered and concentrated to give a crude material. The another batch starting from 1.3 g of 2-chloro-3-nitrotoluene was combined to this crude material and the combined crude products were purified by column chromatography on silica gel eluting with hexane/ethyl acetate (3/1) to afford 2.6 g (77%) of the title compound.

MS (ESI) m/z 227 (M+H)$^+$.

Step 2. 7-methyl-1-[2-(methylthio)ethyl]-1,3-dihydro-2H-benzimidazol-2-one

To a solution of 2-methyl-N-[2-(methylthio)ethyl]-6-nitroaniline (2.6 g, 12 mmol) in ethanol (6.0 mL) was added a solution of Tin(II) chloride dihydrate (7.9 g, 35 mmol) in concd. hydrochloric acid (8.0 mL) at 0° C. and warmed to rt. After 4h, the reaction was quenched by addition of 6N sodium hydroxide (100 mL) and extracted with ethyl acetate (100 mL×2), dried over sodium sulfate, filtered and concentrated. The crude material was dissolved in THF (50 mL) and to this solution was added CDI (2.3 g, 14 mmol) and the mixture was stirred at rt. After 12 h, to the mixture was added CDI (1.5 g, 6.7 mmol) and the reaction mixture was refluxed for 5 h. Then the mixture was cooled to rt and evaporated to dryness. To this was added water (100 mL) and extracted with ethyl acetate (100 mL×2). The combined organic layers were washed with water (50 mL), brine (50 mL), dried over sodium sulfate, filtered and concentrated. The obtained material was dissolved in methanol (30 mL) and to this solution was added 2N sodium hydroxide (3 mL) and stirred at rt for 2 h. Then the mixture was quenched by addition of sat. aq. sodium bicarbonate (50 mL) and extracted with ethyl acetate (100 mL×2). The combined organic layers were washed with water (50 mL), brine (50 mL), dried over sodium sulfate, filtered and concentrated. The residue was purified by column chromatography on silica gel eluting with dichloromethane/methanol (20/1-10/1) to afford 1.8 g (69%) of the title compound.

MS (ESI) m/z 223 (M+H)$^+$.

Step 3. N-{(1S)-1-[(dimethylamino)carbonyl]-2,2-dimethylpropyl}-4-methyl-3-[2-(methylthio)ethyl]-2-oxo-2,3-dihydro-1H-benzimidazole-1-carboxamide To a solution of 7-methyl-1-[2-(methylthio)ethyl]-1,3-dihydro-2H-benzimidazol-2-one (0.21 g, 0.93 mmol) in 1,2- dichloroethane (5 mL) were added triethylamine (0.43 mL, 3.1 mmol) and 4-nitrophenyl chloroformate (0.23 g, 1.1 mmol) at 0° C. and the mixture was stirred at rt for 4 h. Then to this mixture was added a solution of N,N-dimethyl-tert-leucinamide (ca. 1.4 mmol, prepared according to the procedure described in steps 1 and 2 of example 3 from dimethylamine hydrochloride) in 1,2-dichloroethane (3 mL) at 0° C. and stirred rt. After 14 h, the reaction was quenched by addition of water (50 mL) and extracted with dichloromethane (50 mL×2). The combined organic layers were washed with water (30 mL×4), brine (30 mL), dried over sodium sulfate, filtered and concentrated in vacuo. The residue was purified by preparative TLC eluting with dichloromethane/methanol (10/1) to afford 0.31 g (83%) of the title compound.

$^1$H-NMR (300 MHz, CDCl$_3$) δ9.56 (d, J=9.0 Hz, 1H), 8.10 (d, J=7.8 Hz, 1H), 7.07-6.98 (m, 1H), 6.94 (d, J=7.5 Hz, 1H), 4.92 (d, J=9.0 Hz, 1H), 4.32-4.22 (m, 2H), 3.23 (s, 3H), 3.00 (s, 3H), 2.85-2.77 (m, 2H), 2.59 (s, 3H), 2.22 (s, 3H), 1.10 (s, 9H).

MS (ESI) m/z 407 (M+H)$^+$.

Anal. calcd. for C$_{20}$H$_{30}$N$_4$O$_3$S: C, 59.09; H, 7.44; N, 13.78; O, 11.81; S, 7.89. Found: C, 58.97; H, 7.45; N, 13.67.

Example 103

N-{(1S)-1-[(dimethylamino)carbonyl]-2,2-dimethylpropyl}-4-methyl-3-[2-(methylsulfonyl)ethyl]-2-oxo-2,3-dihydro-1H-benzimidazole-1-carboxamide

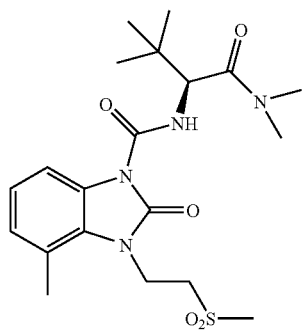

To a solution of N-{(1S)-1-[(dimethylamino)carbonyl]-2,2-dimethylpropyl}-4-methyl-3-[2-(methylthio)ethyl]-2-oxo-2,3-dihydro-1H-benzimidazole-1-carboxamide (EXAMPLE 102, 0.27 g, 0.67 mmol) in dichloromethane (22 mL) were added m-CPBA (0.57 g, 2.3 mmol) and sodium bicarbonate (0.15 g, 1.7 mmol) at rt and stirred for 14 h. Then the reaction was quenched by addition of sat. aq. sodium thiosulfate (50 mL) and the aqueous layer was extracted with dichloromethane (50 mL). The combined organic layers were washed with water (30 mL), brine (30 mL), dried over sodium sulfate, filtered and concentrated. The residue was purified by preparative TLC eluting with dichloromethane/methanol (10/1) to afford 0.19 g (66%) of the title compound. The obtained solid was then recrystallized from hexane/ethylacetate to give 164 mg of the title compound.

$^1$H-NMR (300 MHz, CDCl$_3$) δ9.45 (d, J=8.7 Hz, 1H), 8.11 (d, J=7.5 Hz, 1H), 7.10-7.05 (m, 1H), 6.98 (d, J=7.2 Hz, 1H), 4.92 (d, J=8.7 Hz, 1H), 4.66-4.55 (m, 2H), 3.53-3.44 (m, 2H), 3.22 (s, 3H), 3.04 (s, 3H), 2.99 (s, 3H), 2.64 (s, 3H), 1.10 (s, 9H).

MS (ESI) m/z 439 (M+H)$^+$.

Anal. calcd. for C$_{20}$H$_{30}$N$_4$O$_5$S: C, 54.78; H, 6.90; N, 12.78; O, 18.24; S, 7.31. Found: C, 54.42; H, 6.90; N, 12.50. mp 190.7° C.

Example 104

N-[(1S)-2,2-dimethylpropyl]-3-[2-(methylsulfonyl)ethyl]-2-oxo-2,3-dihydro-1H-benzimidazole-1-carboxamide

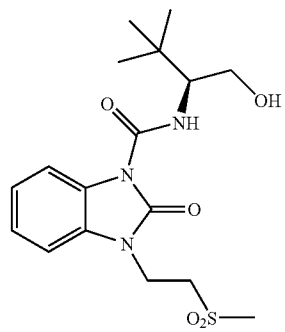

Step 1. N-[2-(methylthio)ethyl]-2-nitroaniline

The title compound was prepared according to the procedure described in step 1 of example 1 from 2-(methylthio)ethylamine.

MS (ESI) m/z 213 (M+H)$^+$.

Step 2. 1-[2-(methylthio)ethyl]-1,3-dihydro-2H-benzimidazol-2-one

The title compound was prepared according to the procedure described in step 2 of EXAMPLE 102.

MS (ESI) m/z 209 (M+H)$^+$.

Step 3. N-[(1S)-1-(hydroxymethyl)-2,2-dimethylpropyl]-3-[2-(methylsulfonyl)ethyl]-2-oxo-2,3-dihydro-1H-benzimidazole-1-carboxamide The title compound was prepared according to the procedure described in steps 3 of EXAMPLE 102 and EXAMPLE 103 starting from L-tert-leucinol.

$^1$H-NMR (270 MHz, CDCl$_3$) δ8.89 (d, J=8.4 Hz, 1H), 8.24-8.21 (m, 1H), 7.30-7.14 (m, 3H), 4.41 (t, J=7.3 Hz, 2H), 4.04-3.86 (m, 2H), 3.73-3.61 (m, 1H), 3.49 (t, J=7.3 Hz, 2H), 2.96 (s, 3H), 2.27-2.18 (m, 1H), 1.05 (s, 9H).

MS (ESI) m/z 384 (M+H)$^+$.

Anal. calcd. for C$_{17}$H$_{25}$N$_3$O$_5$S (+0.2H$_2$O): C, 52.75; H, 6.61; N, 10.86; O, 21.49; S, 8.28. Found: C, 52.44; H, 6.61; N, 10.68.

Example 105

N-[(1S)-2,2-dimethyl-1-(2-methyl-2H-tetrazol-5-yl)propyl]-3-(3-hydroxy-3-methylbutyl)-2-oxo-2,3-dihydro-1H-benzimidazole-1-carboxamide

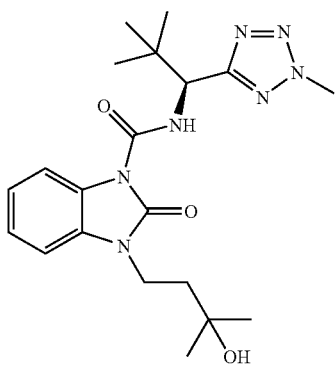

Step 1. benzyl[(1S)-2,2-dimethyl-1-(2H-tetrazol-5-yl)propyl]carbamate

The title compound was prepared according to the procedure described the literature (Olah, G. A. et al. *Synthesis* 1980, 657-658.; Demko, Z. P. and Sharpless, K. B. *Org. Lett.* 2002, 4, 2525-2527.) starting from benzyl [(1S)-1-(aminocarbonyl)-2,2-dimethylpropyl]carbamate.

MS (ESI) m/z 290 (M+H)$^+$.

Step 2. benzyl[(1S)-2,2-dimethyl-1-(2-methyl-2H-tetrazol-5-yl)propyl]carbamate A suspension of benzyl[(1S)-2,2-dimethyl-1-(2H-tetrazol-5-yl)propyl]carbamate (0.41 g, 1.4 mmol), potassium carbonate (1.0 g, 7.0 mmol) and methyl iodide (0.35 mL, 5.6 mmol) in acetone (7 mL) was stirred at 0° C. for 10 min and warmed to rt. After 5 h, the reaction mixture was filtered and concentrated. The residue was purified by column chromatography on silica gel eluting with hexane/ethyl acetate (8/1-4/1-1/1) to afford 0.29 g (68%) of the title compound.

MS (ESI) m/z 304 (M+H)$^+$.

Step 3. (1S)-2,2-dimethyl-1-(2-methyl-2H-tetrazol-5-yl)-1-propanamine

The title compound was prepared according to the procedure described in step 2 of example 3 starting from benzyl [(1S)-2,2-dimethyl-1-(2-methyl-2H-tetrazol-5-yl)propyl]carbamate.

MS (ESI) m/z 170 (M+H)$^+$.

Step 4. N-[(1S)-2,2-dimethyl-1-(2-methyl-2H-tetrazol-5-yl) propyl]-3-(3-hydroxy-3-methylbutyl)-2-oxo-2,3-dihydro-1H-benzimidazole-1-carboxamide The title compound was prepared according to the procedure described in step 4 of EXAMPLE 101 starting from 1-(3-hydroxy-3-methylbutyl)-1,3-dihydro-2H-benzimidazol-2-one and (1S)-2,2-dimethyl-1-(2-methyl-2H-tetrazol-5-yl)-1-propanamine.

$^1$H-NMR (300 MHz, CDCl$_3$) δ 9.67 (d, J=9.3 Hz, 1H), 8.16 (dd, J=7.2, 1.5 Hz, 1H), 7.23-7.12 (m, 2H), 7.06 (d, J=7.2 Hz, 1H), 5.30 (d, J=9.3 Hz, 1H), 4.34 (s, 3H), 4.11-4.06 (m, 2H), 1.95-1.90 (m, 2H), 1.34 (s, 6H), 1.08 (s, 9H).

MS (ESI) m/z 416 (M+H)$^+$.

Anal. calcd. for C$_{20}$H$_{29}$N$_7$O$_3$ (+0.1H$_2$O): C, 57.57; H, 7.05; N, 23.50; O, 11.89. Found: C, 57.29; H, 7.13; N, 23.10.

Example 106

N-[(1S)-2,2-dimethyl-1-(5-methyl-1,3,4-thiadiazol-2-yl)propyl]-3-(3-hydroxy-3-methylbutyl)-2-oxo-2,3-dihydro-1H-benzimidazole-a-carboxamide

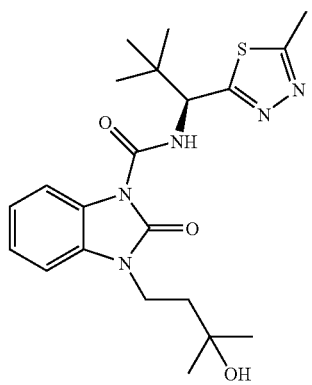

Step 1. benzyl{(1S)-2,2-dimethyl-1-(5-methyl-1,3,4-thiadiazol-2-yl)propyl}carbamate The title compound was prepared according to the procedure described in the literature (Alker, D. et al. *J. Med. Chem.* 1989, 32, 2381-2388.) starting from N-[(benzyloxy)carbonyl]-tert-leucine.

$^1$H-NMR (300 MHz, CDCl$_3$) δ 7.41-7.28 (m, 5H), 5.79-5.75 (m, 1H), 5.14-4.99 (m, 3H), 2.78 (s, 3H), 1.30 (s, 9H).

MS (ESI) m/z 320 (M+H)$^+$.

Step 2. (1S)-2,2-dimethyl-1-(5-methyl-1,3,4-thiadiazol-2-yl)-1-propanamine Hydrochloride A solution of benzyl{(1S)-2,2-dimethyl-1-(5-methyl-1,3,4-thiadiazol-2-yl)propyl}carbamate (ca. 0.6 mmol) in anhydrous hydrogen bromide in acetic acid (25% solution, 1 mL) was stirred at rt for 4 h. Then to this mixture was added ether (50 mL) (precipitate was observed.). The supernatant fluid was decanted. The process of wash with ether followed by decantation was repeated twice and the resultant solid was dried in vacuo to give the crude material of the title compound.

$^1$H-NMR (300 MHz, DMSO-d$_6$) δ 4.91-4.89 (m, 1H), 2.77 (s, 3H), 1.01 (s, 9H).

Step 3. N-[(1S)-2,2-dimethyl-1-(5-methyl-1,3,4-thiadiazol-2-yl)propyl]-3-(3-hydroxy-3-methylbutyl)-2-oxo-2,3-dihydro-1H-benzimidazole-a-carboxamide To a solution of 1-(3-hydroxy-3-methylbutyl)-1,3-dihydro-2H-benzimidazol-2-one (0.12 g, 0.55 mmol) in 1,2- dichloroethane (18 mL) were added triethylamine (0.25 mL, 1.8 mmol) and 4-nitrophenyl chloroformate (0.13 g, 0.66 mmol) at 0° C. and the mixture was stirred at rt for 4 h. Then to this mixture was added a suspension of (1S)-2,2-dimethyl-1-(5-methyl-1,3,4-thiadiazol-2-yl)-1-propanamine hydrochloride and triethylamine (0.2 mL, 1.4 mmol) in 1,2-dichloroethane (5 mL) at 0° C. and stirred rt. After 14 h, the reaction was quenched by addition of water (30 mL) and extracted with dichloromethane (30 mL×3). The combined organic layers were washed with water (30 mL×5), brine (30 mL), dried over sodium sulfate, filtered and concentrated in vacuo. The residue was purified by preparative TLC twice eluting with THF/hexane (1/1) and dichloromethane/methanol (10/1) respectively to afford 15 mg (6%) of the title compound.

$^1$H-NMR (300 MHz, CDCl$_3$) δ9.70 (d, J=10.2 Hz, 1H), 8.15 (d, J=9.0 Hz, 1H), 7.22-7.13 (m, 2H), 7.07 (d, J=8.7 Hz, 1H), 5.31 (d, J=9.0 Hz, 1H), 4.13-4.05 (m, 2H), 2.74 (s, 3H), 1.98-1.88 (m, 2H), 1.34 (s, 6H), 1.15 (s, 9H).

MS (ESI) m/z 432 (M+H)$^+$.

Example 107

N-[(1S)-(1-aminocarbonyl)-2,2-dimethylpropyl]-3-(3-amino-3-methylbutyl)-2-oxo-2,3-dihydro-1H-benzimidazole-1-carboxamide hydrochloride

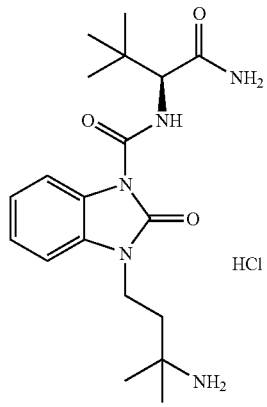

Step 1. N-[1,1-dimethyl-3-[(2-nitrophenyl)amino]propyl]formamide

To a mixture of 2-methyl-4-[(2-nitrophenyl)amino]butan-2-ol (1.7 g, 7.8 mmol) and trimethylsilyl cyanide (4.2 mL, 31 mmol) was added concd. sulfuric acid at −30° C. and the mixture was warmed up to rt. After stirring for 24 h, the reaction mixture was cooled to 0° C. and to the mixture was added water and stirred for 30 min at rt. The mixture was poured into aq. potassium carbonate and extracted with dichloromethane. The combined organic layers were dried over magnesium sulfate and concentrated in vacuo. The crude product was purified by column chromatography on silica gel eluting with dichloromethane/methanol (25/1) to give 1.3 g (66%) of the title compound.

$^1$H-NMR (300 MHz, CDCl$_3$) (a mixture of rotamers) δ 8.34-7.84 (m, 3H), 7.53-7.36 (m, 1H), 6.96-6.57 (m, 2H), 6.02 (bs, 0.2H), 5.35 (bs, 0.8H), 3.53-3.31 (m, 2H), 2.38-1.97 (m, 2H), 1.44 (s, 6H).

MS (ESI) m/z 252 (M+H)$^+$.

Step 2. N-[1,1-dimethyl-3-(2-oxo-2,3-dihydro-1H-benzimidazol-1-yl)propyl]formamide A mixture of N-{1,1-dimethyl-3-[(2-nitrophenyl)amino]propyl}formamide (1.3 g, 5.1 mmol) and palladium on charcoal (0.13 g) in THF (20 mL) was stirred under hydrogen atmosphere (4 atm) for 6 h. The mixture was filtered through a celite pad and the filtrate was concentrated in vacuo.

The obtained crude product was dissolved in THF (20 mL) and to this solution was added CDI (1.0 g, 6.2 mmol). After stirring for 16 h at rt, water was added to the solution. Then it was extracted with ethyl acetate. The combined organic layers were dried over magnesium sulfate and concentrated. The residue was purified by column chromatography on silica gel eluting with dichloromethane/methanol (25/1) to give 1.1 g of a mixture of the title compound and an impurity.

MS (ESI) m/z 248 (M+H)$^+$.

Step 3. 1-(3-amino-3-methylbutyl)-1,3-dihydro-2H-benzimidazol-2-one

A mixture of N-[1,1-dimethyl-3-(2-oxo-2,3-dihydro-1H-benzimidazol-1-yl)propyl]formamide (1.1 g) and hydrogen chloride-methanol (80-90% methanol, 18 mL) was stirred at rt for 50 h. The mixture was concentrated in vacuo and the residue was basified by aq. potassium carbonate and the mixture was extracted with dichloromethane. The combined organic layers were dried over sodium sulfate and concentrated to give 0.81 g (3.7 mmol, 73% for 3 steps) of the title compound.

$^1$H-NMR (300 MHz, CDCl$_3$) δ 7.14-6.97 (m, 4H), 4.02 (t, J=7.5 Hz, 2H), 1.83 (t, J=7.5 Hz, 2H), 1.22 (s, 6H).

MS (ESI) m/z 220 (M+H)$^+$.

Step 4. tert-butyl[1,1-dimethyl-3-(2-oxo-2,3-dihydro-1H-benzimidazol-1-yl)propyl]carbamate To a suspension of 1-(3-amino-3-methylbutyl)-1,3-dihydro-2H-benzimidazol-2-one (0.22 g, 1.0 mmol) in dichloromethane (2 mL) and THF (2 mL) were added triethylamine (0.28 mL, 2.0 mmol) and di-tert-butyl dicarbonate (0.24 g, 1.1 mmol) at rt. After stirring for 1.5 h, the mixture was diluted with ethyl acetate and washed with water and brine, dried over magnesium sulfate and concentrated in vacuo: The residue was purified by column chromatography on silica gel eluting with dichloromethane/methanol (25/1) to give 0.32 g (quantitative yield) of the title compound.

$^1$H-NMR (300 MHz, CDCl$_3$) δ 9.51 (bs, 1H), 7.19-6.95 (m, 4H), 3.93 (t, J=8.3 Hz, 2H), 3.49 (bs, 1H), 2.18 (t, J=8.3 Hz, 2H), 1.44 (s, 9H), 1.36 (s, 6H).

MS (ESI) m/z 320 (M+H)$^+$.

Step 5. tert-butyl{3-[3-({[(1S)-1-(aminocarbonyl)-2,2-dimethylpropyl]amino}carbonyl)-2-oxo-2,3-dihydro-1H-benzimidazol-1-yl]-1,1-dimethylpropyl}carbamate The title compound was prepared according to the procedure described in Step 4 of Example 1 from tert-butyl[1,1-dimethyl-3-(2-oxo-2,3-dihydro-1H-benzimidazol-1-yl)propyl]carbamate.

$^1$H-NMR (300 MHz, CDCl$_3$) δ 9.46 (d, J=9.0 Hz, 1H), 8.15 (d, J=6.0 Hz, 1H), 7.37-7.04 (m, 3H), 5.80 (bs, 1H), 5.42 (bs, 1H), 4.54 (s, 1H), 4.22 (d, J=9.0 Hz, 1H), 4.00-3.83 (m, 2H), 2.31-2.08 (m, 2H), 1.42 (s, 6H), 1.36 (s, 9H), 1.16 (s, 9H).

MS (ESI) m/z 476 (M+H)$^+$.

Step 6. N-[(1S)-(1-aminocarbonyl)-2,2-dimethylpropyl]-3-(3-amino-3-methylbutyl)-2-oxo-2,3-dihydro-1H-benzimidazole-1-carboxamide hydrochloride To a solution of tert-butyl{3-[3-({[(1S)-1-(aminocarbonyl)-2,2-dimethylpropyl]amino}carbonyl)-2-oxo-2,3-dihydro-1H-benzimidazol-1-yl]-1,1-dimethylpropyl}carbamate (0.23 g, 0.48 mmol) in methanol (1.5 mL) was added hydrogen chloride-methanol (80-90% methanol, 6 mL). After stirring at rt for 40 h, the reaction mixture was concentrated in vacuo. The residue was added a mixture of hexane and ethyl acetate and the precipitate was filtered and dried to give 0.18 g (88%) of the title compound.

$^1$H-NMR (DMSO-d$_6$) δ 9.19 (d, J=9.0 Hz, 1H), 8.16 (bs, 2H), 8.06 (d, J=6.0 Hz, 1H), 7.67 (bs, 1H), 7.41-7.10 (m, 4H), 4.27 (d, J=9.0 Hz, 1H), 4.02 (t, J=7.5 Hz, 2H), 1.98 (t, J=7.5 Hz, 2H), 1.36 (s, 6H), 1.00 (s, 9H).

MS (ESI) m/z 376 (M+H)$^+$.

Anal. calcd. for C$_{19}$H$_{29}$N$_5$O$_3$ (+3.0H$_2$O, 1.3HCl): C, 47.85; H, 7.67; N, 14.68; O, 20.13; Cl, 9.66. Found: C, 47.74; H, 7.43; N, 14.71.

Following Examples 108 to 149 were prepared according to the procedure described in step 4 of Example 1.

---

Example 108

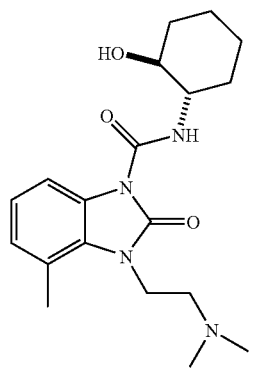

Rel-3-[2-(dimethylamino)ethyl]-N-[(1R,2S)-2-hydroxycyclohexyl]-4-methyl-2-oxo-2,3-dihydro-1H-benzimidazole-1-carboxamide $^1$H-NMR (300 MHz, DMSO) δ10.63 (bs, 1 H), 8.76 (d, J = 7.2 Hz, 1 H), 8.01 (d, J = 7.5 Hz, 1 H), 7.09-7.00 (m, 1 H), 4.88 (bs, 1 H), 4.45 (t, J = 6.6 Hz, 2 H), 3.55-3.45 (m, 1 H), 3.42 (t, J = 6.6 Hz, 2 H), 2.87 (s, 6 H), 2.59 (s, 3 H), 2.10-1.98 (m, 1 H), 1.93-1.80 (m, 1 H), 1.69-1.51 (m, 2 H), 1.36-1.15 (m, 4 H).
MS (ESI) m/z 361 (M + H)$^+$.
Anal. calcd. for C$_{19}$H$_{28}$N$_4$O$_3$ (+1 HCl•0.2 H$_2$O): C, 56.98; H, 7.40; N, 13.99; O, 12.78; Cl, 8.85. Found: C, 56.58; H, 7.41; N, 13.81.

Example 109

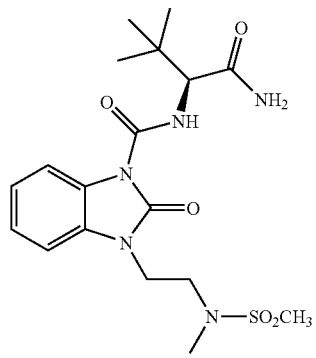

N-[(1S)-1-(aminocarbonyl)-2,2-dimethylpropyl]-3-{2-[methyl(methylsulfonyl)amino]ethyl}-2-oxo-2,3-dihydro-1H-benzimidazole-1-carboxamide $^1$H-NMR (270 MHz, CDCl$_3$) δ 9.38 (d, J = 7.8 Hz, 1 H), 8.17 (d, J = 7.3 Hz, 1 H), 7.31-7.16 (m, 3 H), 5.82 (bs, 1 H), 5.48 (bs, 1 H), 4.22 (d, J = 7.8 Hz, 1 H), 4.19-4.09 (m, 2 H), 3.53-3.45 (m, 2 H), 2.93 (s, 3 H), 2.80 (s, 3 H), 1.15 (s, 9 H).
MS (ESI) m/z 426 (M + H)$^+$.

Example 110

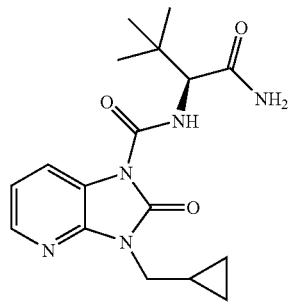

N-[(1S)-1-(aminocarbonyl)-2,2-dimethylpropyl]-3-(cyclopropylmethyl)-2-oxo-2,3-dihydro-1H-imidazo[4,5-b]pyridine-1-carboxamide $^1$H-NMR (300 MHz, DMSO-d$_6$) δ 9.01 (d, J = 9.0 Hz, 1 H), 8.21-8.15 (m, 2 H), 7.69 (bs, 1 H), 7.24-7.17 (m, 2 H), 4.26 (d, J = 9.0 Hz, 1 H), 3.86-3.65 (m, 2 H), 1.34-1.17 (m, 1 H), 0.99 (s, 9 H), 0.54-0.35 (m, 4 H).
MS (ESI) m/z 346 (M + H)$^+$.
Anal. calcd. for C$_{17}$H$_{23}$N$_5$O$_3$: C, 59.12; H, 6.71; N, 20.28; O, 13.90. Found: C, 58.73; H, 6.77; N; 19.93.

| Example 111 | N-[(1S)-1-(aminocarbonyl)-2,2-dimethylpropyl]-3-(cyclopropylmethyl)-4-methyl-2-oxo-2,3-dihydro-1H-imidazo[4,5-c]pyridine-1-carboxamide. |
|---|---|
| 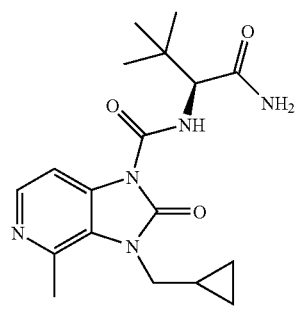 | $^1$H-NMR (300 MHz, CDCl$_3$) δ 9.46 (d, J = 8.1 Hz, 1 H), 8.30 (d, J = 5.7 Hz, 1 H), 8.02 (d, J = 5.7 Hz, 1 H), 5.75 (bs, 1 H), 5.52 (bs, 1 H), 4.19 (d, J = 8.1 Hz, 1 H), 4.08-3.95 (m, 2 H), 2.87 (s, 3 H), 1.25-1.02 (m, 10 H), 0.65-0.46 (m, 4 H).<br>MS (ESI) m/z 360 (M + H)$^+$.<br>Anal. calcd. for C$_{18}$H$_{25}$N$_6$O$_3$ (+0.7 H$_2$O) : C, 58.11; H, 7.15; N, 18.82; O, 15.91. Found: C, 58.24; H, 7.12; N, 18.45. |
| Example 112 | N-[(1S)-1-(aminocarbonyl)-2,2-dimethylpropyl]-2-oxo-3-(1,1,3,3-tetramethylbutyl)-2,3-dihydro-1H-benzimidazole-1-carboxamide |
| 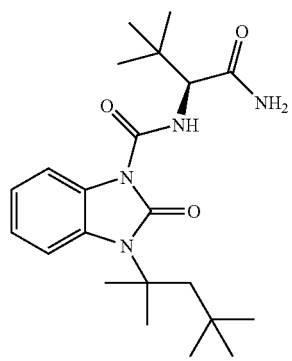 | $^1$H-NMR (270 MHz, CDCl$_3$) δ 9.72 (d, J = 7.8 Hz, 1 H), 8.29-8.25 (m, 1 H), 7.48-7.44 (m, 1 H), 7.16-7.09 (m, 2 H), 5.88 (bs, 1 H), 5.50 (bs, 1 H), 4.22 (d, J = 7.8 Hz, 1 H), 2.17 (d, J = 15.4 Hz, 1 H), 2.03 (d, J = 15.4 Hz, 1 H), 1.90 (s, 3 H), 1.89 (s, 3 H), 1.15 (s, 9 H), 0.88 (s, 9 H).<br>MS (EI) m/z 402 (M)$^+$.<br>Anal. calcd. for C$_{22}$H$_{34}$N$_4$O$_3$(+0.5 H$_2$O): C, 64.21; H, 8.57; N, 13.61; O, 13.61. Found: C, 64.54; H, 8.70; N, 13.44. |
| Example 113 | N-[(1S)-1-(aminocarbonyl)-2,2-dimethylpropyl]-6-methyl-3-[2-(4-morpholinyl)ethyl]-2-oxo-2,3-dihydro-1H-benzimidazole-1-carboxamide |
| 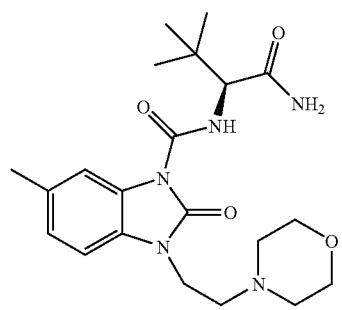 | $^1$H-NMR (270 MHz, DMSO-d$_6$) δ 10.74 (bs, 1 H), 9.08 (d, J = 9.2 Hz, 1 H), 7.86 (bs, 1 H), 7.64 (bs, 1 H), 7.31 (d, J = 7.8 Hz, 1 H), 7.16 (bs, 1 H), 7.04 (d, J = 7.8 Hz, 1 H), 4.35-4.25 (m, 2 H), 4.19 (d, J = 9.2 Hz, 1 H), 4.02-3.84 (m, 2 H), 3.80-3.35 (m, 6 H), 3.20-3.00 (m, 2 H), 2.32 (s, 3 H), 0.94 (s, 9 H).<br>MS (ESI) m/z 418 (M + H)$^+$.<br>Anal. calcd. for C$_{21}$H$_{31}$N$_5$O$_4$ (+1.0 HCl, 0.2 C$_4$H$_8$O$_2$, 1.2 H$_2$O): C, 53.09; H, 7.36; N, 14.20; O, 18.17; Cl, 7.19. Found: C, 53.04; H, 7.27; N, 14.26. |

| Example 114 | N-[(1S)-1-(aminocarbonyl)-2,2-dimethylpropyl]-3-[2-(dimethyl amino)ethyl]-2-oxo-4-(trifluoromethyl)-2,3-dihydro-1H-benzimidazole-1-carboxamide |
|---|---|
| 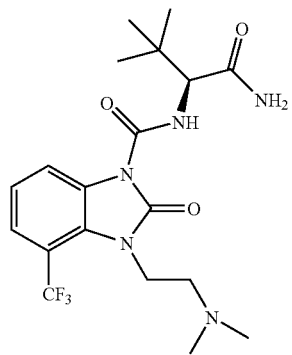 | $^1$H-NMR (300 MHz, CDCl$_3$) δ 9.20 (d, J = 8.7 Hz, 1 H), 8.47 (d, J = 8.1 Hz, 1 H), 7.68 (bs, 1 H), 7.59 (d, J = 8.1 Hz, 1 H), 7.37-7.29 (m, 1 H), 7.24 (bs, 1 H), 4.26 (d, J = 8.7 Hz, 1 H), 4.11-3.98 (m, 2 H), 3.41-3.25 (m, 2 H), 2.20 (s, 6 H), 0.98 (s, 9 H). MS (ESI) m/z 430 (M + H)$^+$. |
| Example 115 | N-[(1S)-1-(aminocarbonyl)-2,2-dimethylpropyl]-5-fluoro-3-[2-(4-morpholinyl)ethyl]-2-oxo-2,3-dihydro-1H-benzimidazole-1-carboxamide |
| 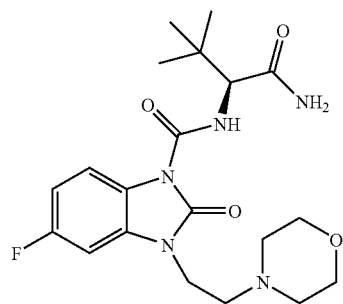 | $^1$H-NMR (300 MHz, DMSO-d$_6$) δ 11.03 (bs, 1 H), 9.00 (d, J = 9.6 Hz, 1 H), 8.02 (dd, J = 9.6, 5.4 Hz, 1 H), 7.69 (bs, 1 H), 7.54 (d, J = 7.5 Hz, 1 H), 7.22 (bs, 1 H), 7.03 (dt, J = 9.6, 3.0 Hz, 1 H), 4.42-4.30 (m, 2 H), 4.26 (d, J = 9.6 Hz, 1 H), 4.09-3.93 (m, 2 H), 3.85-3.42 (m, 6 H), 3.26-3.08 (m, 2 H), 0.99 (s, 9 H). MS (ESI) m/z 422 (M + H)$^+$. Anal. calcd. for C$_{20}$H$_{28}$N$_5$O$_4$F (+1.0 HCl, 0.1 C$_6$H$_{14}$, 0.5 H$_2$O): C, 52.03; H, 6.66; N, 14.73; O, 15.14; F, 4.00; Cl, 7.46. Found: C, 51.67; H, 6.81; N, 14.40. |
| Example 116 | N-[(1S)-1-(aminocarbonyl)-2,2-dimethylpropyl]-3-(3-hydroxy-3-methylbutyl)-4-methyl-2-oxo-2,3-dihydro-1H-benzimidazole-1-carboxamide |
| 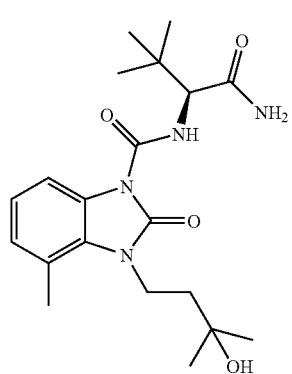 | $^1$H-NMR (300 MHz, DMSO-d$_6$) δ 9.34 (d, J = 9.0 Hz, 1 H), 7.98 (dd, J = 7.2, 2.1 Hz, 1 H), 7.66 (bs, 1 H), 7.20 (bs, 1 H), 7.06-6.99 (m, 2 H), 4.51 (s, 1 H), 4.24 (d, J = 9.0 Hz, 1 H), 4.20-4.09 (m, 2 H), 2.61 (s, 3 H), 1.79-1.70 (m, 2 H), 1.20 (s, 6 H), 0.99 (s, 9 H). MS (ESI) m/z 391 (M + H)$^+$. Anal. calcd. for C$_{20}$H$_{30}$N$_4$O$_4$: C, 61.52; H, 7.74; N, 14.35; O, 16.39. Found: C, 61.17; H, 7.71; N, 14.20. |

Example 117

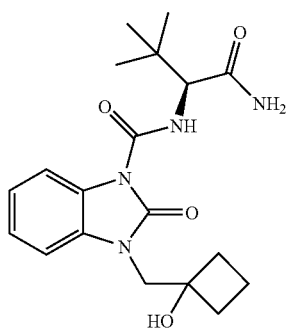

N-[(1S)-1-(aminocarbonyl)-2,2-dimethylpropyl]-3-(1-hydroxy cyclobutyl)methyl]-2-oxo-2,3-dihydro-1H-benzimidazole-1-carboxamide $^1$H-NMR (300 MHz, DMSO-d$_6$) δ 9.24 (d, J = 8.7 Hz, 1 H), 8.03 (d, J = 6.6 Hz, 1 H), 7.68 (bs, 1 H), 7.40 (bs, J = 8.1 Hz, 1 H), 7.22-7.10 (m, 3 H), 5.40 (s, 1 H), 4.27 (d, J = 8.7 Hz, 1 H), 4.01 (d, J = 15.0 Hz, 1 H), 3.94 (d, J = 15.0 Hz, 1 H), 2.20-2.14 (m, 2 H), 2.00-1.90 (m, 2 H), 1.71-1.58 (m, 2 H), 0.99 (s, 9 H).
MS (ESI) m/z 375 (M + H)$^+$.
Anal. calcd. for C$_{19}$H$_{26}$N$_4$O$_4$ (+0.1 H$_2$O): C, 60.65; H, 7.02; N, 14.89; O, 17.44. Found: C, 60.44; H, 7.03; N, 14.62.
mp 158° C.

Example 118

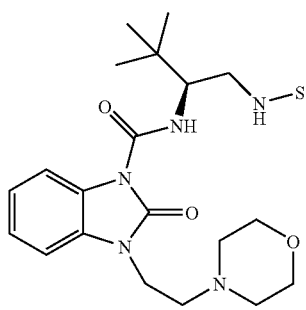

N-((1S)-2,2-dimethyl-1-{[(methylsulfonyl)amino]methyl}propyl)-3-[2-(4-morpholinyl)ethyl]-2-oxo-2,3-dihydro-1H-benzimidazolone-1-carboxamide $^1$H-NMR (300 MHz, CDCl$_3$) δ 9.07 (d, J = 8.7 Hz, 1 H), 8.20-8.17 (m, 1 H), 7.24-7.17 (m, 2 H), 7.07-7.04 (m, 1 H), 5.02-4.93 (m, 1 H), 4.07-3.89 (m, 3 H), 3.68-3.56 (m, 5 H), 3.15 (ddd, J = 12.3, 10.2, 4.2 Hz, 1 H), 2.97 (s, 3 H), 2.77-2.65 (m, 2 H), 2.63-2.47 (m, 4 H), 1.06 (s, 9 H).
MS (ESI) m/z 468 (M + H)$^+$.
Anal. calcd. for C$_{21}$H$_{33}$N$_5$O$_5$S: C, 53.33; H, 7.16; N, 14.81; O, 17.93; S, 6.78. Found: C, 53.12; H, 7.02; N, 14.68.

Example 119

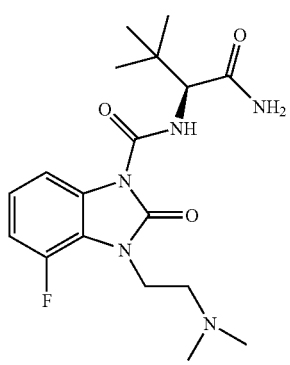

N-[(1S)-1-(aminocarbonyl)-2,2-dimethylpropyl]-3-[2-(dimethyl amino)ethyl]-4-fluoro-2-oxo-2,3-dihydro-1H-benzimidazole-1-carboxamide $^1$H-NMR (300 MHz, DMSO-d$_6$) δ 9.97 (bs, 1 H), 9.08 (d, J = 8.7 Hz, 1 H), 7.97-7.90 (m, 1 H), 7.70 (bs, 1 H), 7.28-7.14 (m, 3 H), 4.38-4.27 (m, 3 H), 3.54-3.42 (m, 2 H), 2.89 (s, 6 H), 0.99 (s, 9 H).
MS (ESI) m/z 380 (M + H)$^+$.
Anal. calcd. for C$_{18}$H$_{26}$N$_5$O$_3$F (+1.0 HCl, 0.5 IPA, 0.5 H$_2$O): C, 51.48; H, 7.09; N, 15.39; O, 14.07; F, 4.18; Cl, 7.79. Found: C, 51.71; H, 7.20; N, 15.19.

| Example 120 | 3-(3-hydroxy-3-methylbutyl)-N-[(1S)-1-(hydroxymethyl)-2,2-dimethylpropyl]-2-oxo-2,3-dihydro-1H-benzimidazole-1-carboxamide |

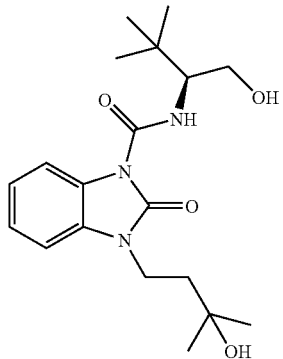

¹H-NMR (300 MHz, CDCl₃) δ 9.05 (d, J = 8.7 Hz, 1 H), 8.21 (dd, J = 7.2, 1.5 Hz, 1 H), 7.24-7.14 (m, 2 H), 7.06 (dd, J = 7.2, 1.5 Hz, 1 H), 4.09-3.88 (m, 4 H), 3.70-3.63 (m, 1 H), 2.41 (bs, 1 H), 1.94-1.89 (m, 2 H), 1.77 (bs, 1 H), 1.34 (s, 6 H), 1.05 (s, 9 H).
MS (ESI) m/z 364 (M + H)⁺.
Anal. calcd. for $C_{19}H_{29}N_3O_4$ (+0.3 $H_2O$): C, 61.87; H, 8.09; N, 11.39; O, 18.65. Found: C, 61.93; H, 8.18; N, 11.37.

| Example 121 | N-[(1S)-2,2-dimethyl-1-(1-methyl-1H-tetrazol-5-yl)propyl]-3-(3-hydroxy-3-methylbutyl)-2-oxo-2,3-dihydro-1H-benzimidazole-1-carboxamide |

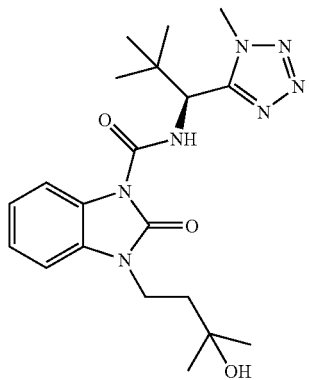

¹H-NMR (270 MHz, CDCl₃) δ 9.74-9.70 (m, 1 H), 8.06 (d, J = 8.1 Hz, 1 H), 7.23-7.05 (m, 3 H), 5.09 (d, J = 7.8 Hz, 1 H), 4.22 (s, 3 H), 4.09-4.03 (m, 2 H), 1.94-1.88 (m, 2 H), 1.34 (s, 3 H), 1.33 (s, 3 H), 1.17 (s, 9 H).
MS (ESI) m/z 416 (M + H)⁺.

| Example 122 | N-{(1S)-2,2-dimethyl-1-[(methylsulfonyl)methyl]propyl}-3-(3-hydroxy-3-methylbutyl)-2-oxo-2,3-dihydro-1H-benzimidazole-1-carboxamide |

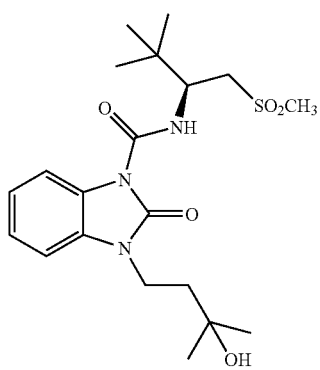

¹H-NMR (300 MHz, CDCl₃) δ 9.14 (d, J = 9.6 Hz, 1 H), 8.22 (d, J = 6.6 Hz, 1 H), 7.24-7.16 (m, 2 H), 7.09-7.07 (m, 1 H), 4.54-4.40 (m, 1 H), 4.15-3.97 (m, 2 H), 3.34 (d, J = 14.7 Hz, 1 H), 3.11 (dd, J = 14.7, 10.2 Hz, 1 H), 3.02 (s, 3 H), 1.94-1.89 (m, 2 H), 1.33 (s, 6 H), 1.05 (s, 9 H).
MS (ESI) m/z 426 (M + H)⁺.
Anal. calcd. for $C_{20}H_{31}N_3O_5S$ (+0.3 $H_2O$): C, 55.74; H, 7.39; N, 9.75; O, 19.68; S, 7.44. Found: C, 55.56; H, 7.42; N, 9.66.

Example 123

3-(3-hydroxy-3-methylbutyl)-N-[1-(hydroxymethyl)cyclopentyl-2-oxo-2,3-dihydro-1H-benzimidazole-1-carboxamide

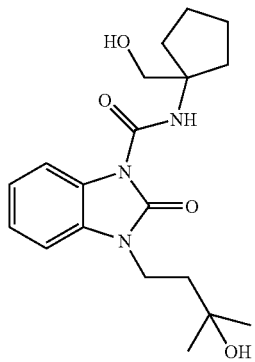

$^1$H-NMR (300 MHz, CDCl$_3$) δ 9.06 (s, 1 H), 8.18 (d, J = 7.2 Hz, 1 H), 7.25-7.14 (m, 2 H), 7.09-7.02 (m, 1 H), 4.09-3.93 (m, 3 H), 3.84-3.76 (m, 2 H), 1.94-1.66 (m, 10 H), 1.33 (s, 6 H).
MS (ESI) m/z 362 (M + H)$^+$.
Anal. calcd. for C$_{19}$H$_{27}$N$_4$O$_4$ : C, 62.51; H, 7.57; N, 11.51; O, 18.41. Found: C, 62.41; H, 7.60; N, 11.24.

Example 124

N-[1-(aminocarbonyl)-2,2-dimethylpropyl]-3-[(1-hydroxycyclohexyl)methyl]-2-oxo-2,3-dihydro-1H-benzimidazole-1-carboxamide

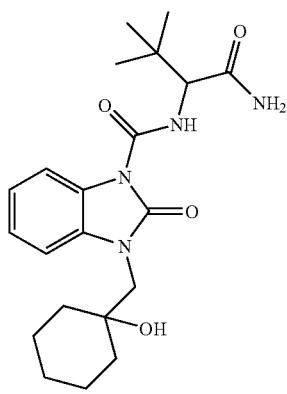

$^1$H-NMR (270 MHz, CDCl$_3$) δ 9.42 (d, J = 7.9 Hz, 1 H), 8.19-8.16 (m, 1 H), 7.22-7.07 (m, 3 H), 5.90 (br, 1 H), 5.58 (br, 1 H), 4.22 (d, J = 7.9 Hz, 1 H), 3.89 (s, 2 H), 2.28 (d, J = 3.3 Hz, 1 H), 1.14 (s, 9 H), 1.64-1.52 (m, 10 H)
MS (ESI) m/z 403 (M + H)$^+$.

Example 125

N-[1-(aminocarbonyl)-2,2-dimethylpropyl]-2-oxo-3-(tetrahydrofuran-2-ylmethyl)-2,3-dihydro-1H-benzimidazole-1-carboxamide

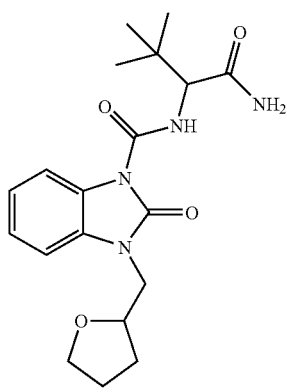

$^1$H-NMR (270 MHz, CDCl$_3$) δ 9.47-9.44 (m, 1 H), 8.17 (d, J = 7.3 Hz, 1 H), 7.24-7.13 (m, 3 H), 4.30-4.19 (m, 2 H), 4.08-3.70 (m, 4 H), 2.11-1.68 (m, 4 H), 1.15 (s, 9 H).
MS (ESI) m/z 375 (M + H)$^+$.

| | |
|---|---|
| Example 126 | N-[2,2-dimthyel-1-(pyrrolidin-1-ylmethyl)propyl]-3-(2-morpholin-4-ylethyl)-2-oxo-2,3-dihydro-1H-benzimidazole-1-carboxamide |
| 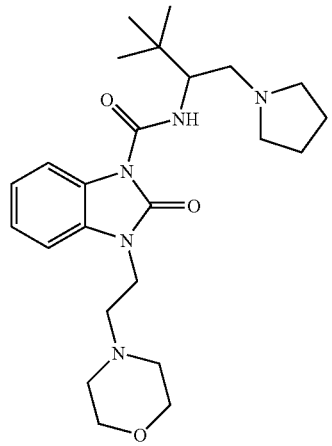 | $^1$H-NMR (270 MHz, CDCl$_3$) δ 8.87 (d, J = 9.9 Hz, 1 H), 8.24-8.21 (m, 1 H), 7.23-7.13 (m, 2 H), 7.05-7.01 (m, 1 H), 4.14-3.98 (m, 3 H), 3.67 (t, J = 4.6 Hz, 4 H), 3.00-2.66 (m, 8 H), 2.60-2.47 (m, 4 H), 1.76-1.89 (m, 4 H), 1.02 (s, 9 H). MS (ESI) m/z 444 (M + H)$^+$. |
| Example 127 | N-(1-acetyl-2,2-dimethylpropyl)-3-(2-morpholin-4-ylethyl)-2-oxo-2,3-dihydro-1H-benzimidazole-1-carboxamide |
| 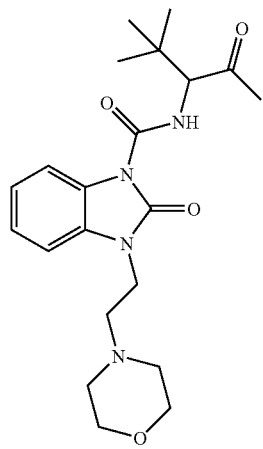 | $^1$H-NMR (300 MHz, CDCl$_3$) δ 9.37 (d, J = 7.3 Hz, 1 H), 8.09 (dd, J = 2.0, 7.3 1 H), 7.18-7.07 (m, 2 H), 6.99-6.96 (m, 1 H), 4.37 (d, J = 7.3 Hz, 1 H), 3.95 (t, J = 6.6 Hz, 2 H), 3.62-3.59 (m, 4 H), 2.63 (t, J = 6.6 Hz, 2 H), 2.54-2.41 (m, 4 H), 2.55 (s, 3 H), 1.04 (s, 9 H). MS (ESI) m/z 403 (M + H)$^+$. |
| Example 128 | N-[(1S)-1-(aminocarbonyl)-2,2-dimethylpropyl]-4-methyl-2-oxo-3-(2-pyrrolidin-1-ylethyl)-2,3-dihydro-1H-benzimidazole-1-carboxamide hydrochloride |
| 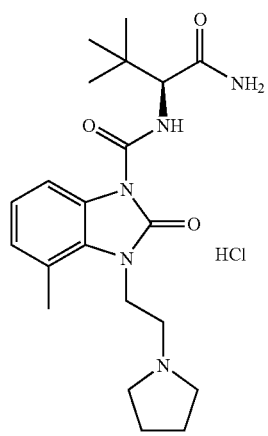 | $^1$H-NMR (270 MHz, CDCl$_3$) δ 13.1-12.8 (m, 1 H), 9.41-9.23 (m, 1 H), 8.13-7.94 (m, 1 H), 7.11-6.77 (m, 2 H), 6.31-6.05 (m, 1 H), 5.68-5.45 (m, 1 H), 4.90-4.40 (m, 2 H), 4.27-3.70 (m, 3 H), 3.17-2.80 (m, 1 H), 2.70 (bs, 3 H), 2.47-1.88 (m, 4 H), 1.22-0.81 (m, 13 H). MS (ESI) m/z 402 (M + H)$^+$. Anal. calcd. for C$_{21}$H$_{31}$N$_5$O$_3$ (+1.0 H$_2$O, 1.0 HCl): C, 55.32; H, 7.52; N, 15.36; O, 14.04; Cl, 7.78. Found: C, 55.53; H, 7.55; N; 15.08. |

Example 129

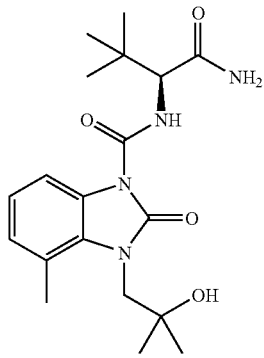

N-[(1S)-1-(aminocarbonyl)-2,2-dimethylpropyl]-3-(2-hydroxy-2-methylpropyl)-4-methyl-2-oxo-2,3-dihydro-1H-benzimidazole-1-carboxamide $^1$H-NMR (300 MHz, CDCl$_3$) δ 9.49 (d, J = 9.0 Hz, 1 H), 8.15 (d, J = 8.3 Hz, 1 H), 7.07 (dd, J = 8.3, 8.3 Hz, 1 H), 6.98 (d, J = 8.3 Hz, 1 H), 5.88 (bs, 1 H), 5.57 (bs, 1 H), 4.23 (s, 2 H), 4.21 (d, J = 9.0 Hz, 1 H), 3.05 (bs, 1 H), 2.63 (s, 3 H), 1.33 (s, 6 H), 1.14 (s, 9 H).
MS (ESI) m/z 377 (M + H)$^+$.
Anal. calcd. for C$_{19}$H$_{28}$N$_4$O$_4$ (+0.45 H$_2$O, 0.30 C$_3$H$_6$O, 0.10 C$_4$H$_8$O$_2$ HCl): C, 59.35; H, 7.73; N, 13.64; O, 19.28. Found: C, 58.95; H, 7.54; N; 13.61.

Example 130

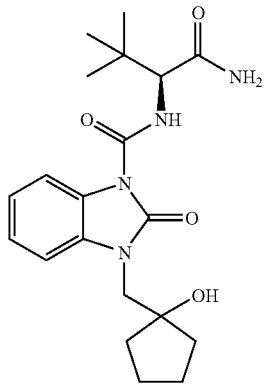

N-[(1S)-1-(aminocarbonyl)-2,2-dimethylpropyl]-3-[(1-hydroxycyclopentyl)methyl]-2-oxo-2,3-dihydro-1H-benzimidazole-1-carboxamide $^1$H-NMR (300 MHz, CDCl$_3$) δ 9.41 (d, J = 7.5 Hz, 1 H), 8.18 (d, J = 6.0 Hz, 1 H), 7.27-7.14 (m, 3 H), 5.84 (bs, 1 H), 5.50 (bs, 1 H), 4.22 (d, J = 7.5 Hz, 1 H), 4.04 (s, 2 H), 1.92-1.66 (m, 8 H), 1.14 (s, 9 H).
MS (ESI) m/z 389 (M + H)$^+$.
Anal. calcd. for C$_{20}$H$_{28}$N$_4$O$_4$ (+0.30 H$_2$O): C, 60.99; H, 7.32; N, 14.22; O, 17.47. Found: C, 60.62; H, 7.31; N; 13.94.

Example 131

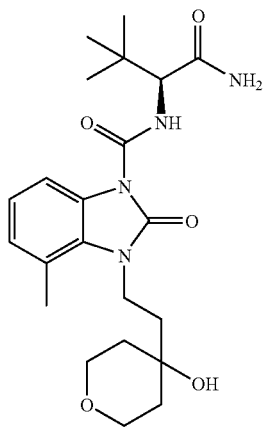

N-[(1S)-1-(aminocarbonyl)-2,2-dimethylpropyl]-3-[2-(4-hydroxytetrahyro-2H-pyran-4-yl)ethyl]-4-methyl-2-oxo-2,3-dihydro-1H-benzimidazole-1-carboxamide $^1$H-NMR (270 MHz, CDCl$_3$) δ 9.51 (d, J = 9.5 Hz, 1 H), 8.11 (d, J = 7.4 Hz, 1 H), 7.05 (dd, J = 7.4, 7.4 Hz, 1 H), 6.97 (d, J = 7.4 Hz, 1 H), 5.88 (bs, 1 H), 5.59 (bs, 1 H), 4.30 (m, 2 H), 4.22 (d, J = 9.5 Hz, 1 H), 3.89-3.67 (m, 4 H), 2.62 (s, 3 H), 2.17 (s, 1 H), 1.94 (t, J = 8.1 Hz, 2 H), 1.84-1.50 (m, 4 H), 1.14 (s, 9 H).
MS (ESI) m/z 433 (M + H)$^+$.

| Example 132 | N-[(1S)-1-(aminocarbonyl)-2,2-dimethylpropyl]-2-oxo-3-(tetrahydro-2H-pyran-4-ylmethyl)-2,3-dihydro-1H-benzimidazole-1-carboxamide |

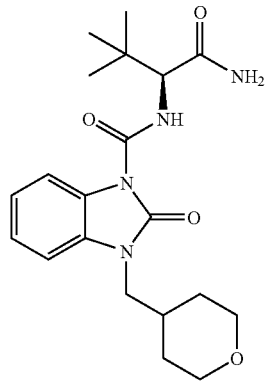

$^1$H-NMR (300 MHz, CDCl$_3$) δ 9.45 (d, J = 9.0 Hz, 1 H), 8.18 (d, J = 9.0 Hz, 1 H), 7.25-7.14 (m, 2 H), 7.03 (d, J = 9.0 Hz, 1 H), 5.98 (bs, 1 H), 5.73 (bs, 1 H), 4.24 (d, J = 9.0 Hz, 1 H), 4.05-3.89 (m, 2 H), 3.85-3.67 (m, 2 H), 3.41-3.30 (m, 2 H), 2.22-2.08 (m, 1 H), 1.68-1.35 (m, 4 H), 1.16 (s, 9 H).
MS (ESI) m/z 389 (M + H)$^+$.

| Example 133 | N-[(1S)-1-tert-butyl-3,3,3-trifluoro-2-hydroxypropyl]-3-(2-morpholin-4-ylethyl)-2-oxo-2,3-dihydro-1H-benzimidazole-1-carboxamide hydrochloride |

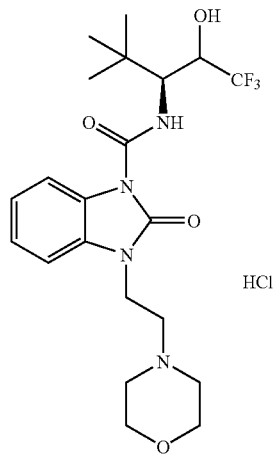

$^1$H-NMR (300 MHz, DMSO-d$_6$) δ 10.57 (bs, 1 H), 8.87 (d, J = 12.0 Hz, 1 H), 8.09 (d, J = 9.0 Hz, 1 H), 7.50 (d, J = 6.0 Hz, 1 H), 7.37-7.16 (m, 2 H), 6.59 (bs, 1 H), 4.51-3.93 (m, 5 H), 3.77-3.05 (m, 9 H), 1.02 (s, 9 H).
MS (ESI) m/z 459 (M + H)$^+$.
Anal. calcd. for C$_{21}$H$_{29}$F$_3$N$_4$O$_4$ (+2.1 H$_2$O, 1.0 HCl): C, 47.34; H, 6.47; N, 10.52; C, 18.32; F, 10.70; Cl, 6.65. Found: C, 47.03; H, 6.17; N; 10.19.

| Example 134 | N-[(1S)-1-tert-butyl-3,3,3-trifluoro-2-oxopropyl]-3-(2-morpholin-4-ylethyl)-2-oxo-2,3-dihydro-1H-benzimidazole-1-carboxamide |

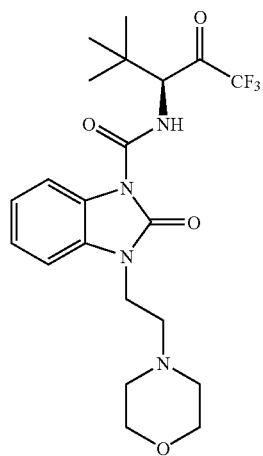

$^1$H-NMR (300 MHz, DMSO-d$_6$) δ 9.52 (d, J = 7.5 Hz, 1 H), 7.96 (d, J = 9.0 Hz, 1 H), 7.44-7.10 (m, 3 H), 4.88 (d, J = 7.5 Hz, 1 H), 4.04 (t, J = 6.0 Hz, 2 H), 3.59-3.41 (m, 4 H), 2.61 (t, J = 6.0 Hz, 2 H), 2.75-2.36 (m, 4 H), 1.08 (s, 9 H).
MS (ESI) m/z 457 (M + H)$^+$.
Anal. calcd. for C$_{21}$H$_{27}$F$_3$N$_4$O$_4$ (+2.1 H$_2$O, 1.0 HCl): C, 54.82; H, 6.00; N, 12.18; O, 14.61; F, 12.39. Found: C, 54.51; H, 5.95; N; 11.96.

Example 135

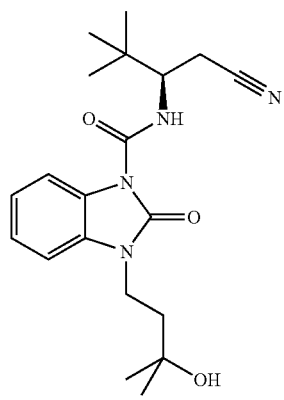

N-[(1R)-1-(cyanomethyl)-2,2-dimethylpropyl]-3-(3-hydroxy-3-methylbutyl)-2-oxo-2,3-dihydro-1H-benzimidazole-1-carboxamide $^1$H-NMR (300 MHz, CDCl$_3$) δ 9.22 (d, J = 9.0 Hz, 1 H), 8.22 (d, J = 9.0 Hz, 1 H), 7.30-7.08 (m, 3 H), 4.23-4.02 (m, 3 H), 2.81 (dd, J = 17.3, 6.0 Hz, 1 H), 2.56 (dd, J = 17.3, 7.5 Hz, 1 H), 1.93 (t, J = 7.5 Hz, 2 H), 1.34 (s, 6 H), 1.07 (s, 9 H).
MS (ESI) m/z 377 (M + H)$^+$.
Anal. calcd. for C$_{20}$H$_{28}$N$_4$O$_3$ (+1.0 H$_2$O): C, 61.52; H, 7.74; N, 14.35; O, 16.39. Found: C, 61.83; H, 7.47; N; 14.36.

Example 136

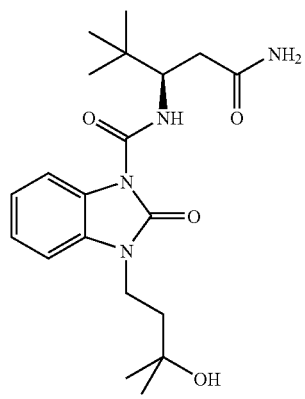

N-[(1R)-1-(2-amino-2-oxoethyl)-2,2-dimethylpropyl]-3-(3-hydroxy-3-methylbutyl)-2-oxo-2,3-dihydro-1H-benzimidazole-1-carboxamide $^1$H-NMR (300 MHz, CDCl$_3$) δ 9.08 (d, J = 10.8 Hz, 1 H), 8.20 (d, J = 8.1 Hz, 1 H), 7.41-7.02 (m, 3 H), 6.60 (bs, 1 H),
5.30 (bs, 1 H), 4.22-3.96 (m, 3 H), 2.72
(dd, J = 11.5, 4.1 Hz, 1 H), 2.40 (dd, J = 11.5, 5.4 Hz, 1 H), 1.92 (t, J = 8.1 Hz, 2 H), 1.34 (s, 6 H), 1.04 (s, 9 H).
MS (ESI) m/z 391 (M + H)$^+$.
HR-MS (FAB) Calcd. for C$_{20}$H$_{31}$N$_4$O$_4$: 391.2345. Found: 391.2343.

Example 137

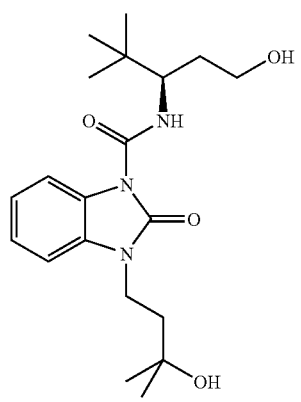

N-[(1R)-1-(2-hydroxyethyl)-2,2-dimethylpropyl]-3-(3-hydroxy-3-methylbutyl)-2-oxo-2,3-dihydro-1H-benzimidazole-1-carboxamide $^1$H-NMR (270 MHz, CDCl$_3$) δ 8.88 (d, J = 10.8 Hz, 1 H), 8.20 (d, J = 5.4 Hz, 1 H), 7.28-7.05 (m, 3 H), 4.11-3.97
(m, 3 H), 3.69-3.65 (m, 2 H), 3.31 (bs, 1 H),
2.12-1.98 (m, 1 H), 1.92 (t, J = 8.1 Hz, 2 H), 1.72-1.68 (m, 2 H), 1.34 (s, 6 H), 1.04 (s, 9 H).
MS (ESI) m/z 378 (M + H)$^+$.
Anal. calcd. for C$_{20}$H$_{31}$N$_4$O$_4$ (+0.8 H$_2$O): C, 61.30; H, 8.38; N, 10.72; O, 19.60. Found: C, 61.56; H, 8.06; N; 10.73.

| Example 138 | N-[(1S)-1-tert-butyl-2-hydroxy-2-methylpropyl]-3-(3-hydroxy-3-methylbutyl)-2-oxo-2,3-dihydro-1H-benzimidazole-1-carboxamide |
|---|---|
| 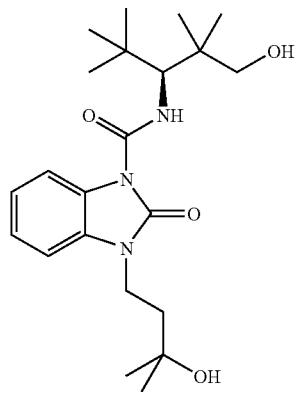 | $^1$H-NMR (300 MHz, CDCl$_3$) δ 8.25 (d, J = 9.0 Hz, 1 H), 7.35-7.04 (m, 4 H), 4.12-4.07 (m, 2 H), 3.84 (d, J = 9.0 Hz, 1 H), 1.94 (t, J = 9.0 Hz, 2 H), 1.70 (s, 1 H), 1.68 (s, 1 H), 1.42 (s, 3 H), 1.39 (s, 3 H), 1.35 (s, 6 H), 1.16 (s, 9 H). MS (ESI) m/z 392 (M + H)$^+$. Anal. calcd. for C$_{21}$H$_{33}$N$_3$O$_4$ (+0.5 H$_2$O): C, 62.98; H, 8.56; N, 10.49; O, 17.98. Found: C, 63.02; H, 8.38; N; 10.46. |
| Example 139 | N-[(1S)-1-(aminocarbonyl)-2,2-dimethylpropyl]-3-(2-dimethylamino)-2-methylprpyl]-2-oxo-2,3-dihydro-1H-benzimidazole-1-carboxamide hydrochloride |
| 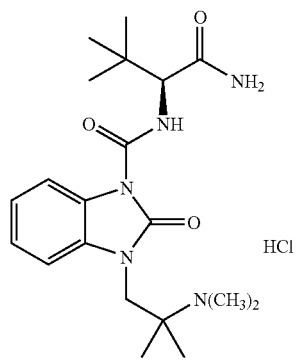 | $^1$H-NMR (300 MHz, DMSO-d$_6$) δ 11.07 (bs, 1 H), 9.13 (d, J = 9.0 Hz, 1 H), 8.08 (d, J = 6.0 Hz, 1 H), 7.72 (bs, 1 H), 7.59 (d, J = 6.0 Hz, 1 H), 7.41-7.04 (m, 3 H), 4.44-4.18 (m, 3 H), 2.84 (d, J = 3.0 Hz, 6 H), 1.41 (s, 6 H), 1.41 (s, 6 H), 1.00 (s, 9 H). MS (ESI) m/z 390 (M + H)$^+$. Anal. calcd. for C$_{20}$H$_{31}$N$_3$O$_4$ (+1.5 H$_2$O, 1.0 HCl, 0.2 C$_4$H$_8$O$_2$): C, 53.09; H, 7.84; N, 14.88; O, 16.66; Cl, 7.53. Found: C, 53.14; H, 7.77; N; 14.53. |
| Example 140 | N-[(1S)-2,2-dimethyl-1-(1,3,4-oxadiazol-2-yl)propyl]-3-(3-hydroxy-3-methylbutyl)-2-oxo-2,3-dihydro-1H-benzimidazole-1-carboxamide |
| 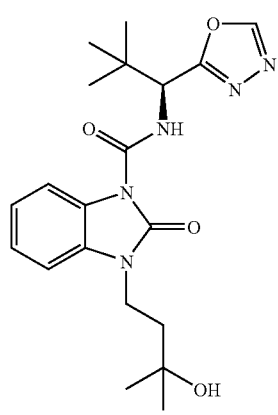 | $^1$H-NMR (270 MHz, CDCl$_3$) δ 9.69 (d, J = 8.1 Hz, 1 H), 8.39 (s, 1 H), 8.15 (d, J = 8.1 Hz, 1 H), 7.35-7.06 (m, 3 H), 5.27 (d, J = 8.1 Hz, 1 H), 4.16-4.03 (m, 2 H), 1.96-1.87 (m, 2 H), 1.34 (s, 6 H), 1.13 (s, 9 H). MS (ESI) m/z 402 (M + H)$^+$. HR-MS (FAB) Calcd. for C$_{20}$H$_{28}$N$_5$O$_4$ : 402.2141. Found: 402.2150. |

| | |
|---|---|
| Example 141 | N-{(1R)-2,2-dimethyl-1-[(2-methyl-2H-tetrazol-5-yl)methyl]propyl}-3-(3-hydroxy-3-methylbutyl)-2-oxo-2,3-dihydro-1H-benzimidazole-1-carboxamide |
| 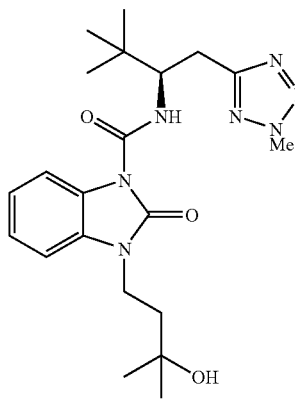 | $^1$H-NMR (300 MHz, CDCl$_3$) δ 8.95 (d, J = 9.0 Hz, 1 H), 8.09 (d, J = 9.0 Hz, 1 H), 7.36-6.99 (m, 3 H), 4.31-4.22 (m, 1 H), 4.22 (s, 3 H), 4.05 (t, J = 7.5 Hz, 2 H), 3.31 (dd, J = 15.0, 3.0 Hz, 1 H), 2.96 (dd, J = 15.0, 12.0 Hz, 1 H), 1.91 (t, J = 7.5 Hz, 2 H), 1.89 (s, 1 H), 1.33 (s, 6 H), 1.08 (s, 9 H).<br>MS (ESI) m/z 430 (M + H)$^+$.<br>HR-MS (FAB) Calcd. for C$_{21}$H$_{32}$N$_7$O$_3$: 430.2567. Found: 430.2580. |
| Example 142 | N-[(1S)-1-tert-butyl-3,3,3-trifluoro-2-oxopropyl]-3-(3-hydroxy-3-methyl butyl)-2-oxo-2,3-dihydro-1H-benzimidazole-1-carboxamide |
| 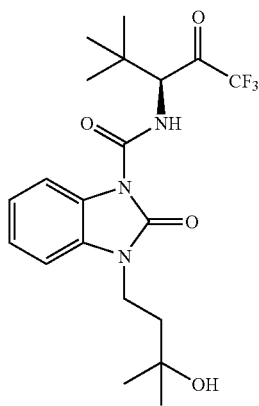 | $^1$H-NMR (300 MHz, CDCl$_3$) δ 9.53 (d, J = 7.5 Hz, 1 H), 8.15 (d, J = 6.0 Hz, 1 H), 7.24-7.02 (m, 3 H), 4.90 (d, J = 7.5 Hz, 1 H), 4.08 (t, J = 7.5 Hz, 2 H), 1.93 (t, J = 7.5 Hz, 2 H), 1.34 (s, 6 H), 1.15 (s, 9 H).<br>MS (ESI) m/z 430 (M + H)$^+$.<br>HR-MS (FAB) Calcd. for C$_{20}$H$_{27}$F$_3$N$_4$O$_4$: 430.1954. Found: 430.1962. |
| Example 143 | N-[(1S)-1-tert-butyl-3,3,3-trifluoro-2-oxopropyl]-3-[2-(methylsulfonyl)ethyl]-2-oxo-2,3-dihydro-1H-benzimidazole-1-carboxamide |
| 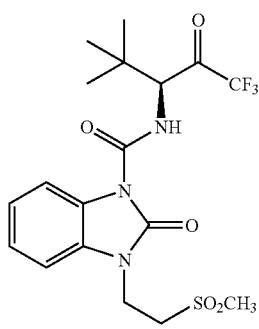 | $^1$H-NMR (300 MHz, CDCl$_3$) δ 9.36 (d, J = 7.5 Hz, 1 H), 8.17 (d, J = 9.0 Hz, 1 H), 7.35-7.16 (m, 3 H), 4.91 (d, J = 7.5 Hz, 1 H), 4.42 (t, J = 6.8 Hz, 2 H), 3.50 (t, J = 6.8 Hz, 2 H), 2.97 (s, 3 H), 1.15 (s, 9 H).<br>MS (ESI) m/z 450 (M + H)$^+$.<br>HR-MS (FAB) Calcd. for C$_{18}$H$_{23}$F$_3$N$_3$O$_5$S: 450.1311. Found: 450.1326. |

| Example 144 | N-[2,2-dimethyl-1-(1,3-oxazol-2-yl)propyl]-3-(3-hydroxy-3-methylbutyl)-2-oxo-2,3-dihydro-1H-benzimidazole-1-carboxamide |
|---|---|

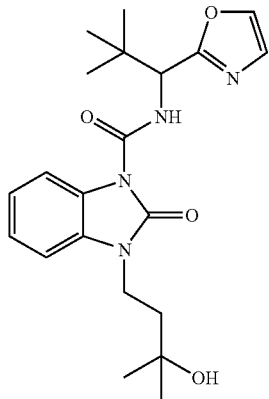

$^1$H-NMR (300 MHz, CDCl$_3$) δ 9.65 (d, J = 9.0 Hz, 1 H), 8.18 (d, J = 9.0 Hz, 1 H), 7.62 (s, 1 H), 7.27-7.02 (m, 4 H), 5.11 (d, J = 9.0 Hz, 1 H), 4.08 (t, J = 8.3 Hz, 2 H), 1.93 (t, J = 8.3 Hz, 2 H), 1.78 (bs, 1 H), 1.34 (s, 6 H), 1.08 (s, 9 H).
MS (ESI) m/z 401 (M + H)$^+$.
HR-MS (FAB) Calcd. for C$_{21}$H$_{29}$F$_3$N$_4$O$_4$: 401.2189. Found: 401.2189.

| Example 145 | N-[(1S)-1-(aminocarbonyl)-2,2-dimethylpropyl]3-[(4-hydroxytetrahydro-2H-pyran-4-yl)methyl]-4-methyl-2-oxo-2,3-dihydro-1H-benzimidazole-1-carboxamide |
|---|---|

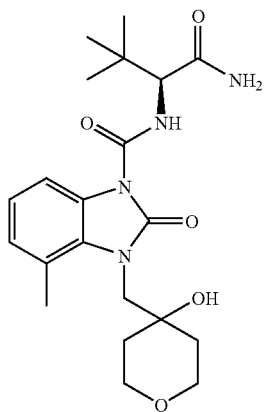

$^1$H-NMR (300 MHz, CDCl$_3$) δ 9.43 (d, J = 9.0 Hz, 1 H), 8.16 (d, J = 7.5 Hz, 1 H), 7.09 (dd, J = 7.5, 7.5 Hz, 1 H), 6.98 (d, J = 7.5 Hz, 1 H), 5.76 (bs, 1 H), 5.46 (bs, 1 H), 4.25 (s, 2 H), 4.20 (d, J = 9.0 Hz, 1 H), 3.86-3.71 (m, 5 H), 2.64 (s, 3 H), 1.91-1.70 (m, 2 H), 1.60-1.50 (m, 2 H), 1.14 (s, 9 H).
MS (ESI) m/z 419 (M + H)$^+$.
Anal. calcd. for C$_{21}$H$_{30}$N$_4$O$_5$ (+0.2 H$_2$O, 0.2 C$_4$H$_8$O$_2$, 0.1 C$_6$H$_{14}$): C, 58.14; H, 7.62; N, 12.11; O, 22.13. Found: C, 58.40; H, 7.22; N; 12.48.

| Example 146 | N-[(1S)-2,2-dimethyl-1-(2-methyl-2H-tetrazol-5-yl)propyl]-3-(3-methoxypropyl)-2-oxo-2,3-dihydro-1H-benzimidazole-1-carboxamide |
|---|---|

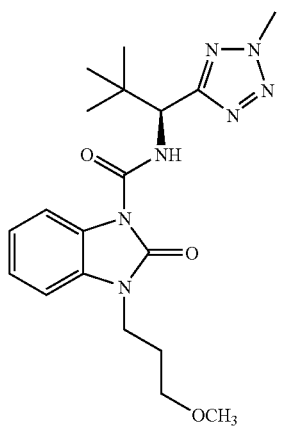

$^1$H-NMR (300 MHz, CDCl$_3$) δ 9.71 (d, J = 9.0 Hz, 1 H), 8.16 (d, J = 6.0 Hz, 1 H), 7.23-7.04 (m, 3 H), 5.30 (d, J = 9.0 Hz, 1 H), 4.34 (s, 3 H), 4.02 (t, J = 7.5 Hz, 2 H), 3.41 (t, J = 6.0 Hz, 2 H), 3.34 (s, 3 H), 2.12-1.97 (m, 2 H), 1.09 (s, 9 H).
MS (ESI) m/z 402 (M + H)$^+$.

Example 147

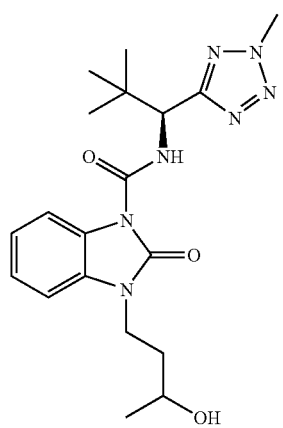

N-[(1S)-2,2-dimethyl-1-(2-methyl-2H-tetrazol-5-yl)propyl]-3-(3-hydroxybutyl)-2-oxo-2,3-dihydro-1H-benzimidazole-1-carboxamide (1:1)

$^1$H-NMR (300 MHz, CDCl$_3$) δ 9.67-9.52 (m, 1 H), 8.18 (d, J = 6.0 Hz, 1 H), 7.32-7.05 (m, 3 H), 5.30 (d, J = 9.0 Hz, 1 H), 4.39-4.17 (m, 4 H), 3.97-3.70 (m, 2 H), 2.80-2.70 (m, 1 H), 1.99-1.65 (m, 2 H), 1.29-1.18 (m, 3 H), 1.09 (s, 9 H).
MS (ESI) m/z 402 (M + H)$^+$.

Example 148

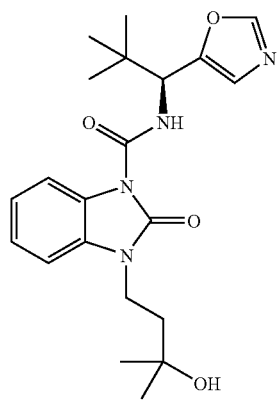

N-[(1S)-2,2-dimethyl-1-(1,3-oxazol-5-yl)propyl]-3-(3-hydroxy-3-methylbutyl)-2-oxo-2,3-dihydro-1H-benzimidazole-1-carboxamide $^1$H-NMR (300 MHz, CDCl$_3$) δ 9.52 (d, J = 9.0 Hz, 1 H), 8.18 (d, J = 9.0 Hz, 1 H), 7.84 (s, 1 H), 7.32-7.07 (m, 3 H), 7.00 (s, 1 H), 5.06 (d, J = 9.0 Hz, 1 H), 4.09 (t, J = 7.5 Hz, 2 H), 1.93 (t, J = 7.5 Hz, 2 H), 1.73 (bs, 1 H), 1.35 (s, 6 H), 1.07 (s, 9 H).
MS (ESI) m/z 401 (M + H)$^+$.

Example 149

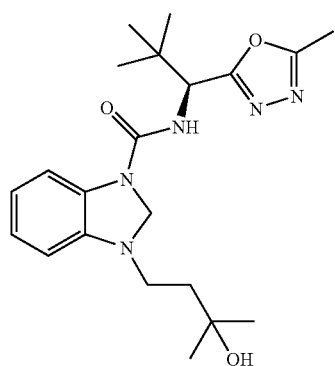

N-[(1S)-1-2,2-dimethyl-1-(5-methyl-1,3,4-oxadiazol-2-yl)propyl]-3-(3-hydroxy-3-methylbutyl)-2-oxo-2,3-dihydro-1H-benzimidazole-1-carboxamide $^1$H-NMR (300 MHz, CDCl$_3$) δ 9.61 (d, J = 8.7 Hz, 1 H), 8.15 (d, J = 7.2 Hz, 1 H), 7.23-7.14 (m, 2 H), 7.09-7.06 (m, 1 H), 5.17 (d, J = 8.7 Hz, 1 H), 4.10-4.05 (m, 2 H), 2.54 (s, 3 H), 1.95-1.90 (m, 2 H), 1.34 (s, 6 H), 1.12 (s, 9 H).
MS (ESI) m/z 416 (M + H)$^+$.
Anal. calcd. for C$_{21}$H$_{29}$N$_5$O$_4$: C, 60.71; H, 7.04; N, 16.86; O, 15.40. Found: C, 60.55; H, 7.04; N, 16.76.

Following Examples 150, to 151 were prepared according to the procedure described in Example 107.

| Example 150 | 1-[3-({[2,2-dimethyl-1-(2-methyl-2H-tetrazol-5-yl)propyl]amino}carbonyl)-7-methyl-2-oxo-2,3-dihydro-1H-benzimidazol-1-yl]-2-methylpropan-2-aminium formate |
|---|---|
| 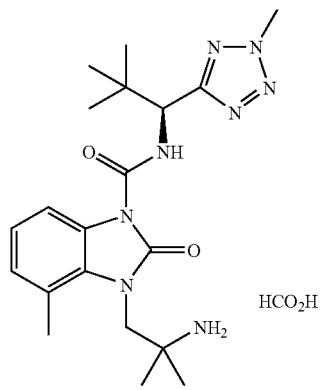 | $^1$H-NMR (300 MHz, CDCl$_3$) δ 9.60 (d, J = 9.0 Hz, 1 H), 8.34 (s, 1 H), 8.17 (d, J = 8.3 Hz, 1 H), 7.07 (dd, J = 8.3, 8.3 Hz, 1 H), 6.97 (d, J = 8.3 Hz, 1 H), 5.30 (d, J = 9.0 Hz, 1 H), 4.33 (bs, 5 H), 3.50 (s, 2 H), 2.60 (s, 3 H), 1.43 (s, 3 H), 1.40 (s, 3 H), 1.07 (s, 9 H). MS (ESI) m/z 415 (M + H)$^+$. |
| Example 151 | 4-[3-({[2,2-dimethyl-1-(2-methyl-2H-tetrazol-5-yl)propyl]amino}carbonyl)-7-methyl-2-oxo-2,3-dihydro-1H-benzimidazol-1-yl]-2-methylbutan-2-aminium formate |
| 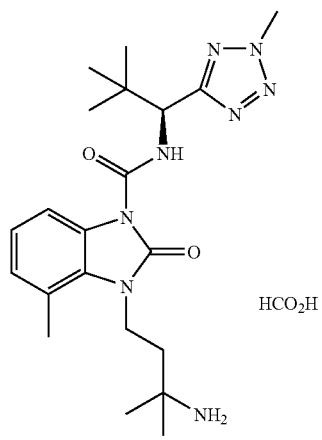 | $^1$H-NMR (300 MHz, CDCl$_3$) δ 9.75 (d, J = 9.0 Hz, 1 H), 8.40 (s, 1 H), 8.10 (d, J = 6.0 Hz, 1 H), 7.06-6.79 (m, 2 H), 5.30 (d, J = 9.0 Hz, 1 H), 4.34-4.20 (m, 2 H), 4.33 (s, 3 H), 3.25 (bs, 3 H), 2.58 (s, 3 H), 2.05 (t, J = 9.0 Hz, 2 H), 1.43 (s, 6 H), 1.06 (s, 9 H). MS (ESI) m/z 429 (M + H)$^+$. |

Following Examples 152 to 154 were prepared according to the procedure described in Example 102.

| Example 152 | N-[(1S)-1-(aminocarbonyl)-2,2-dimetylpropyl]-4-methyl-3-[2-(methylthio)ethyl]-2-oxo-2,3-dihydro-1H-benzimidazole-1-carboxamide |
|---|---|
| 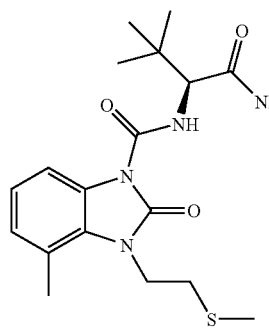 | $^1$H-NMR (300 MHz, CDCl$_3$) δ 9.54 (d, J = 8.1 Hz, 1 H), 8.11 (d, J = 7.5 Hz, 1 H), 7.06 (t, J = 7.5 Hz, 1 H), 6.97 (d, J = 7.5 Hz, 1 H), 5.82 (bs, 1 H), 5.49 (bs, 1 H), 4.33-4.27 (m, 2 H), 4.21 (d, J = 8.1 Hz, 1 H), 2.85-2.80 (m, 2 H), 2.59 (s, 3 H), 2.22 (s, 3 H), 1.14 (s, 9 H). MS (ESI) m/z 379 (M + H)$^+$. Anal. calcd. for C$_{18}$H$_{26}$N$_4$O$_3$S : C, 57.12; H, 6.92; N, 14.80; O, 12.68; S, 8.47. Found: C, 57.19; H, 6.93; N, 14.78. |

-continued

| | |
|---|---|
| Example 153 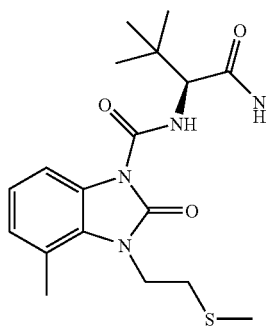 | N-{(1S)-2,2-dimethyl-1-[(methylamino)carbonyl]propyl}-4-methyl-3-[2-(methylthio)ethyl]-2-oxo-2,3-dihydro-1H-benzimidazole-1-carboxamide<br><br>$^1$H-NMR (300 MHz, CDCl$_3$) δ 9.56-9.46 (m, 1 H), 8.09 (d, J = 7.2 Hz, 1 H), 7.08-7.03 (m, 1 H), 6.96 (d, J = 7.5 Hz, 1 H), 5.81 (bs, 1 H), 4.32-4.27 (m, 2 H), 4.14 (d, J = 8.1 Hz, 1 H), 2.85-2.79 (m, 5 H), 2.59 (s, 3 H), 2.22 (s, 3 H), 1.11 (s, 9 H).<br>MS (ESI) m/z 393 (M + H)$^+$.<br>Anal. calcd. for C$_{19}$H$_{28}$N$_4$O$_3$S (+0.2 H$_2$O): C, 57.61; H, 7.23; N, 14.14; O, 12.92; S, 8.10. Found: C, 57.29; H, 7.21; N, 14.01. |
| Example 154 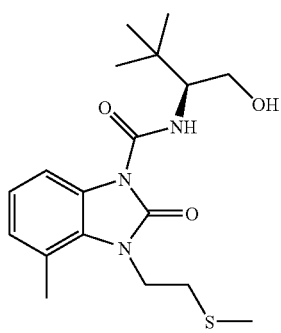 | N-[(1S)-1-(hydroxymethyl)-2,2-dimethylpropyl]-4-methyl-3-[2-(methylthio)ethyl]-2-oxo-2,3-dihydro-1H-benzimidazole-1-carboxamide<br><br>$^1$H-NMR (300 MHz, DMSO-d$_6$) δ 8.92 (d, J = 9.6 Hz, 1 H), 8.04-8.01 (m, 1 H), 7.08-7.00 (m, 2 H), 4.74-4.66 (m, 1 H), 4.27-4.23 (m, 2 H), 3.74-3.64 (m, 2 H), 3.51-3.43 (m, 1 H), 2.84-2.79 (m, 2 H), 2.59 (s, 1 H), 2.15 (s, 3 H), 0.95 (s, 9 H).<br>MS (ESI) m/z 366 (M + H)$^+$.<br>Anal. calcd. for C$_{18}$H$_{27}$N$_3$O$_3$S: C, 59.15; H, 7.45; N, 11.50; O, 13.13; S, 8.77. Found: C, 58.76; H, 7.39; N, 11.48. |

Following Examples 155 to 161 were prepared according to the procedure described in Example 103.

| | |
|---|---|
| Example 155 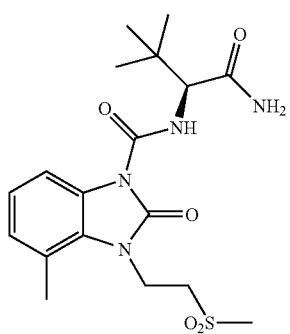 | N-{(1S)-1-(aminocarbonyl)-2,2-dimethylpropyl]-4-methyl-3-[2-(methylsulfonyl)ethyl]-2-oxo-2,3-dihydro-1H-benzimidazole-1-carboxamide<br><br>$^1$H-NMR (300 MHz, CDCl$_3$) δ 9.41 (d, J = 8.7 Hz, 1 H), 8.12 (d, J = 8.7 Hz, 1 H), 7.12-7.06 (m, 1 H), 7.00 (d, J = 8.1 Hz, 1 H), 5.75 (bs, 1 H), 5.48 (bs, 1 H), 4.66-4.61 (m, 2 H), 4.21 (d, J = 8.7 Hz, 1 H), 3.51-3.46 (m, 2 H), 3.04 (s, 3 H), 2.65 (s, 3 H), 1.14 (s, 9 H).<br>MS (ESI) m/z 411 (M + H)$^+$.<br>Anal. calcd. for C$_{18}$H$_{26}$N$_4$O$_5$S (+0.5 H$_2$O, 0.2 C$_4$H$_8$O$_2$): C, 51.66; H, 6.59; N, 12.82; O, 21.60; S, 7.34. Found: C, 51.96; H, 6.33; N, 12.89.<br>mp 177.5° C. 238.2° C. |

| Example 156 | N-{(1S)-2,2-dimethyl-1-[(methylamino)carbonyl]propyl}-4-methyl-3-[2-(methylsulfonyl)ethyl]-2-oxo-2,3-dihydro-1H-benzimidazole-1-carboxamide |

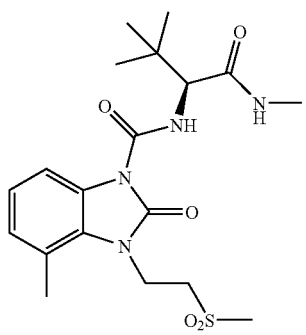

¹H-NMR (300 MHz, CDCl₃) δ 9.42 (d, J = 9.0 Hz, 1 H), 8.09 (d, J = 7.2 Hz, 1 H), 7.07 (t, J = 7.2 Hz, 1 H), 6.98 (d, J = 7.2 Hz, 1 H), 5.89-5.80 (m, 1 H), 4.65-4.57 (m, 2 H), 4.16 (d, J = 9.0 Hz, 1 H), 3.51-3.46 (m, 2 H), 3.04 (s, 3 H), 2.84 (d, J = 4.5 Hz, 3 H), 2.64 (s, 3 H), 1.11 (s, 9 H).
MS (ESI) m/z 425 (M + H)⁺.
Anal. calcd. for C₁₉H₂₈N₄O₅S (+0.2 H₂O): C, 53.08; H, 6.71; N, 13.03; O, 19.72; Cl, 7.46. Found: C, 52.76; H, 6.54; N, 12.64.

| Example 157 | N-[(1S)-1-(hydroxymethyl)-2,2-dimethylpropyl]-4-methyl-3-[2-(methylsulfonyl)ethyl]-2-oxo-2,3-dihydro-1H-benzimidazole-1-carboxamide |

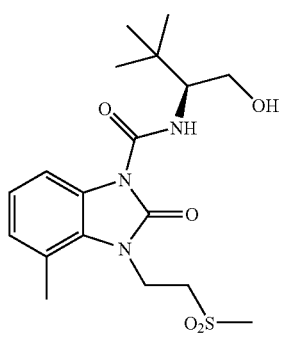

¹H-NMR (300 MHz, CDCl₃) δ 8.87 (d, J = 9.6 Hz, 1 H), 8.02 (dd, J = 7.2, 1.2 Hz, 1 H), 7.10-7.01 (m, 2 H), 4.72-4.69 (m, 1 H), 4.53-4.48 (m, 2 H), 3.74-3.59 (m, 4 H), 3.51-3.41 (m, 1 H), 3.12 (s, 3 H), 2.62 (s, 3 H), 0.95 (s, 9 H).
MS (ESI) m/z 398 (M + H)⁺.
Anal. calcd. for C₁₈H₂₇N₃O₅S (+0.1 H₂O): C, 54.14; H, 6.87; N, 10.52; O, 20.44; S, 8.03. Found: C, 53.90; H, 6.87; N, 10.26.

| Example 158 | rel-N-[(1R,2S)-2-hydroxycyclohexyl]-4-methyl-3-[2-(methylsulfonyl)ethyl]-2-oxo-2,3-dihydro-1H-benzimidazole-1-carboxamide |

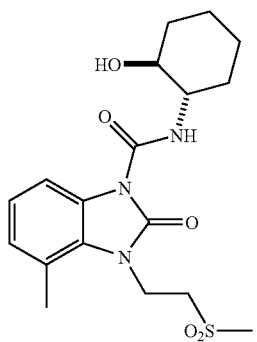

¹H-NMR (300 MHz, DMSO-d₆) δ 8.80 (d, J = 7.5 Hz, 1 H), 8.02-7.99 (m, 1 H), 7.09-7.01 (m, 2 H), 4.87 (d, J = 5.1 Hz, 1 H), 4.52-4.47 (m, 2 H), 3.66-3.45 (m, 3 H), 3.11 (s, 3 H), 2.61 (s, 3 H), 2.10-1.98 (m, 1 H), 1.92-1.80 (m, 1 H), 1.70-1.56 (m, 2 H), 1.36-1.20 (m, 4 H).
MS (ESI) m/z 396 (M + H)⁺.
Anal. calcd. for C₁₈H₂₅N₃O₅S (+0.3 H₂O): C, 53.93; H, 6.44; N, 10.48; O, 21.15; S, 8.00. Found: C, 53.66; H, 6.24; N, 10.36.
mp 152.3° C., 238.9° C.

| | |
|---|---|
| Example 159 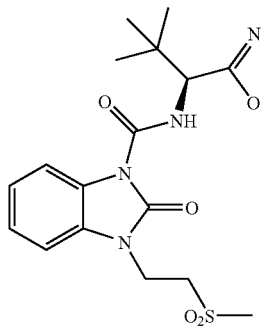 | N-[(1S)-2,2-dimethyl-1-(3-methyl-1,2,4-oxadiazol-5-yl)propyl]-3-[2-(methylsulfonyl)ethyl]-2-oxo-2,3-dihydro-1H-benzimidazole-<br><br>$^1$H-NMR (300 MHz, CDCl$_3$) δ 9.49 (d, J = 8.1 Hz, 1 H), 8.16 (d, J = 8.1 Hz, 1 H), 7.30-7.15 (m, 3 H), 5.17 (d, J = 8.1 Hz, 1 H), 4.45-4.40 (m, 2 H), 3.54-3.49 (m, 2 H), 2.98 (s, 3 H), 2.41 (s, 3 H), 1.12 (s, 9 H).<br>MS (ESI) m/z 436 (M + H)$^+$.<br>Anal. calcd. for C$_{19}$H$_{25}$N$_5$O$_5$S: C, 52.40; H, 5.79; N, 16.08; O, 18.37; S, 7.36. Found: C, 52.06; H, 5.75; N, 15.79<br>m.p 124.2° C. |
| Example 160 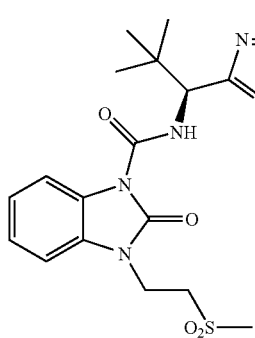 | N-[(1S)-2,2-dimethyl-1-(2-methyl-2H-tetrazol-5-yl)propyl]-3-[2-(methylsulfonyl)ethyl]-2-oxo-2,3-dihydro-1H-benzimidazole-1-carboxamide<br><br>$^1$H-NMR (300 MHz, CDCl$_3$) δ 9.56 (d, J = 8.7 Hz, 1 H), 8.18 (d, J = 7.5 Hz, 1 H), 7.28-7.14 (m, 3 H), 5.29 (d, J = 8.7 Hz, 1 H), 4.44-4.39 (m, 2 H), 4.34 (s, 3 H), 3.54-3.49 (m, 2 H), 2.97 (s, 3 H), 1.08 (s, 9 H).<br>MS (ESI) m/z 436 (M + H)$^+$.<br>Anal. calcd. for C$_{18}$H$_{25}$N$_7$O$_4$S (+0.1 H$_2$O): C, 49.44; H, 5.81; N, 22.42; O, 15.00; S, 7.33. Found: C, 49.18; H, 5.76; N, 22.09. |
| Example 161 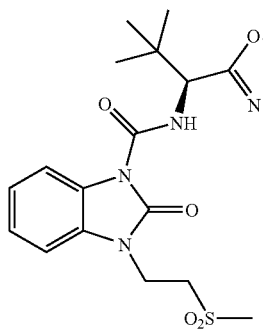 | N-[(1S)-2,2-dimethyl-1-(5-methyl-1,3,4-oxadiazol-2-yl)propyl]-3-[2-(methylsulfonyl)ethyl)-2-oxo-2,3-dihydro-1H-benzimidazole-1-carboxamide<br><br>$^1$H-NMR (300 MHz, CDCl$_3$) δ 9.46 (d, J = 10.2 Hz, 1 H), 8.18-8.15 (m, 1 H), 7.30-7.15 (m, 3 H), 5.15 (d, J = 10.2 Hz, 1 H), 4.45-4.39 (m, 2 H), 3.54-3.48 (m, 2 H), 2.98 (s, 3 H), 2.55 (s, 3 H), 1.12 (s, 9 H).<br>MS (ESI) m/z 436 (M + H)$^+$.<br>Anal. calcd. for C$_{19}$H$_{25}$N$_5$O$_5$S (+0.1 H$_2$O): C, 52.18; H, 5.81; N, 16.02; O, 18.66; S, 7.33. Found: C, 51.91; H, 5.70; N, 15.91. |

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A compound of the formula (I):

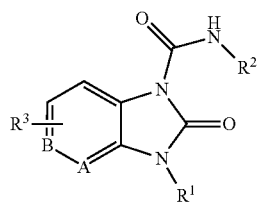

or a pharmaceutically acceptable salt thereof, wherein:
  A is a carbon atom;
  B is a carbon atom;
  $R^1$ is a $C_1$-$C_4$ alkyl group substituted with 1 to 3 substituents independently selected from the group consisting of a $C_1$-$C_4$ alkyl group, a hydroxy group, a $C_1$-$C_4$ alkoxy group, a mercapto group, a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a di($C_1$-$C_4$ alkyl)amino group, a ($C_1$-$C_4$alkyl)($C_1$-$C_4$ alkylsulfonyl) amino group, a cycloalkyl group, and a heterocyclyl group; wherein the cycloalkyl group is optionally substituted with 1 to 3 substituents selected from the group consisting of a hydroxy group, a $C_1$-$C_4$ alkoxy group and a $C_1$-$C_4$ alkyl group; and wherein the heterocyclyl group is optionally substituted with 1 to 3 substituents selected from the group consisting of a hydroxy group, a $C_1$-$C_4$ alkoxy group and a $C_1$-$C_4$ alkyl group;
  $R^2$ is selected from the group consisting of a cycloalkyl group, a $C_6$-$C_{10}$ aryl group, and a $C_1$-$C_{10}$ alkyl group; wherein the cycloalkyl group is optionally substituted with 1 to 4 substituents selected from the group consisting of a hydroxy group, a $C_1$-$C_4$ hydroxyalkyl group, a $C_1$-$C_4$ alkoxy group, a $C_6$-$C_{10}$ aryloxy group, a mercapto group, a $C_1$-$C_4$ alkylthio group, a $C_6$-$C_{10}$ arylthio group, a carboxy group, a $C_1$-$C_4$ alkoxycarbonyl group, a $C_1$-$C_4$ alkyl group, a $C_2$-$C_4$ alkenyl group and a $C_2$-$C_4$ alkynyl group; wherein the $C_6$-$C_{10}$ aryl group is optionally substituted with 1 to 3 substituents selected from the group consisting of a hydroxy group and a $C_1$-$C_4$ alkyl group; and wherein the $C_1$-$C_{10}$ alkyl group is optionally substituted with 1 to 3 substituents independently selected from the group consisting of a cyano group, a hydroxy group, a trifluoromethyl group, a $C_2$-$C_4$ alkenyl group, a $C_2$-$C_4$ alkynyl group, a $C_1$-$C_4$ alkoxy group, a $C_6$-$C_{10}$ aryloxy group, a mercapto group, a $C_1$-$C_4$ alkylthio group, a $C_1$-$C_4$ alkylsulfinyl group, a $C_1$-$C_4$ alkylsulfonyl group, a $C_1$-$C_4$ alkyisulfonylamino group, a $C_6$-$C_{10}$ arylthio group, a carboxy group, a $C_1$-$C_4$ alkyl-carbonyl group, a trifluoromethyl-carbonyl group, a $C_1$-$C_4$ alkoxy carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl)amino-carbonyl group, a ($C_1$-$C_4$ hydroxyalkyl)($C_1$-$C_4$ alkyl)amino-carbonyl group, a cycloalkyl group, and a $C_6$-$C_{10}$ aryl group; and
  $R^3$ is a hydrogen atom, a halogen atom, a hydroxy group, a $C_1$-$C_4$ alkyl group, $C_1$-$C_4$ haloalkyl group or a $C_1$-$C_4$ alkoxy group.

2. The compound or the pharmaceutically acceptable salt as claimed in claim 1, wherein
  $R^1$ is a $C_1$-$C_4$ alkyl group substituted with 1 to 3 substituents independently selected from the group consisting of a $C_1$-$C_4$ alkyl group, a hydroxy group, a $C_1$-$C_4$ alkoxy group, an amino group, a $C_1$-$C_4$ alkylamino group, a di($C_1$-$C_4$ alkyl)amino group, a ($C_1$-$C_4$ alkyl)($C_1$-$C_4$ alkylsulfonyl)amino group, a cycloalkyl group, and a heterocyclyl group; wherein the cycloalkyl group is optionally substituted with 1 to 3 substituents selected from the group consisting of a hydroxy group, a $C_1$-$C_4$ alkoxy group and a $C_1$-$C_4$ alkyl group; and wherein the heterocyclyl group is optionally substituted with 1 to 3 substituents selected from the group consisting of a hydroxy group, a $C_1$-$C_4$ alkoxy group and a $C_1$-$C_4$ alkyl group;
  $R^2$ is a cycloalkyl group or a $C_1$-$C_{10}$ alkyl; wherein the cycloalkyl group is substituted with 1 to 3 substituents selected from the group consisting of a hydroxy group, a $C_1$-$C_4$ hydroxyalkyl group, a carboxy group, and a $C_1$-$C_4$ alkoxy-carbonyl group; and wherein the $C_1$-$C_{10}$ alkyl group is substituted with 1 to 3 substituents independently selected from the group consisting of a cyano group, a hydroxy group, a trifluoromethyl group, a $C_2$-$C_4$ alkenyl group, a $C_2$-$C_4$ alkynyl group, a $C_1$-$C_4$ alkoxy group, a $C_6$-$C_{10}$ aryloxy group, a mercapto group, a $C_1$-$C_4$ alkylthio group, a $C_1$-$C_4$ alkylsulfinyl group, a $C_1$-$C_4$ alkylsulfonyl group, a $C_1$-$C_4$ alkylsulfonylamino group, a $C_6$-$C_{10}$ arylthio group, a carboxy group, a $C_1$-$C_4$alkyl-carbonyl group, a trifluoromethyl-carbonyl group, a $C_1$-$C_4$ alkoxy-carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl)amino-carbonyl group, a ($C_1$-$C_4$ hydroxyalkyl)($C_1$-$C_4$ alkyl)amino-carbonyl group, a heterocyclyl-carbonyl group, a cycloalkyl group, and a $C_6$-$C_{10}$ aryl group; and
  $R^3$ is a hydrogen atom, a halogen atom, a $C_1$-$C_4$ alkyl group or a $C_1$-$C_4$ alkoxy group.

3. The compound or the pharmaceutically acceptable salt as claimed in claim 2, wherein
  $R^1$ is a $C_1$-$C_2$ alkyl group substituted with 1 to 3 substituents independently selected from the group consisting of a $C_1$-$C_2$ alkyl group, a hydroxy group, a $C_1$-$C_4$ alkoxy group, an amino group, a $C_1$-$C_4$ alkylamino group, a di($C_1$-$C_4$ alkyl)amino group, a ($C_1$-$C_4$ alkyl)($C_1$-$C_4$ alkylsulfonyl)amino group, a cycloalkyl group; and a heterocyclyl group; wherein the cycloalkyl group is optionally substituted with 1 to 3 substituents selected from the group consisting of a hydroxy group, a $C_1$-$C_4$ alkoxy group and a $C_1$-$C_4$ alkyl group; and wherein the heterocyclyl group is optionally substituted with 1 to 3 substituents selected from the group consisting of a hydroxy group, a $C_1$-$C_4$ alkoxy group and a $C_1$-$C_4$ alkyl group;
  $R^2$ is a $C_1$-$C_6$ alkyl group substituted with 1 to 2 substituents independently selected from the group consisting of a hydroxy group, a trifluoromethyl group, a $C_1$-$C_4$ alkylsulfonyl group, a $C_1$-$C_4$ alkylsulfonylamino group, a $C_1$-$C_4$alkyl-carbonyl group, a trifluoromethyl-carbonyl group, a $C_1$-$C_4$ alkoxy-carbonyl group, an amino carbonyl group, a $C_1$-$C_4$ alkylamino-carbonyl group, a $C_1$-$C_4$ hydroxyalkylamino-carbonyl group, a di($C_1$-$C_4$ alkyl) amino-carbonyl group, and a ($C_1$-$C_4$ hydroxyalkyl)($C_1$-$C_4$ alkyl)amino-carbonyl group; and
  $R^3$ is a hydrogen atom, a fluorine atom or a $C_1$-$C_2$ alkyl group.

4. A pharmaceutical composition comprising the compound or the pharmaceutically acceptable salt thereof, as claimed in claim 1 and a pharmaceutically acceptable carrier.

5. The compound as claimed in claim 1 that is:
  N-[(1S,2S)-1-(Aminocarbonyl)-2-methylbutyl]-3-(2-morpholin-4-ylethyl)-2-oxo-2,3-dihydro-1H-benzimidazole-1-carboxamide;
  Methyl N-{[3-(2-Morpholin-4-ylethyl)2-oxo-2,3-dihydro-1H-benzimidazole-1-y]carbonyl}-L-isoleucinate;
  N-{(1S,2S)-1-[(Dimethylamino)carbonyl]-2-methylbutyl}-3-(2-morpholin-4-ylethyl)-2-oxo-2,3-dihydro-1H-benzimidazol-1-carboxamide;
  N-[(1S)-1-(Aminocarbonyl)2,2-dimethylpropyl]-3-(2-morpholin-4-ylethyl)-2-oxo-2,3-dihydro-1H-benzimidazole-1-carboxamide;
  Methyl 3-methyl-N-{[3-(2-morpholin-4-ylethyl)-2-oxo-2,3-dihydro-1H-benzimidazol-1-yl]carbonyl}-L-valinate;

N-{(1S)-2,2-Dimethyl-1-[(methylamino)carbonyl]propyl-3-(2-morpholin-4-ylethyl)-2-oxo-2,3-dihydro-1H-benzimidazole-1-carboxamide;
N-{(1S)-1-[(Dimethylamino)carbonyl]-2,2-dimethylpropyl}-3-(2-morpholin-4-ylethyl)-2-oxo-2,3-dihydro-1H-benzimidazole-1-carboxamide;
N-[(1S,2S)-1-(Aminocarbonyl)-2-methylbutyl]-2-oxo-3-(2-piperidin-1-ylethyl)-2,3-dihydro-1H-benzimidazole-1-carboxamide;
N-[(1S,2S)-1-(Aminocarbonyl)-2-methylbutyl]-4-methoxy-3-(2-morpholin-4-ylethyl)-2-oxo-2,3-dihydro-1H-benzimidazole-1-carboxamide;
N-[(1S)-1-(Aminocarbonyl)-2,2-dimethylpropyl]-2-oxo-3-[2-(tetrahydro-2H-pyran-4-yl)ethyl]-2,3-dihydro-1H-benzimidazole-1-carboxamide;
N-[(1S)-1-(Aminocarbonyl)-2,2-dimethylpropyl]-3-(cyclopropylmethyl)-2-oxo-2,3-dihydro-1H-benzimidazole-1-carboxamide;
N-[(1S)-1-(Aminocarbonyl)-2,2-dimethylpropyl]-3-(3-methylbutyl)-2-oxo-2,3-dihydro-1H-benzimidazole-1-carboxamide;
N-[(1S)-1-(Aminocarbonyl)-2,2-dimethylpropyl]-3-(3,3-dimethylbutyl)-2-oxo-2,3-dihydro-1H-benzimidazole-1-carboxamide;
N-[(1S)-1-(Aminocarbonyl)-2,2-dimethylpropyl]-3-[(1-methylpiperidin-2-yl)methyl]-2-oxo-2,3-dihydro-1H-benzimidazole-1-carboxamide;
N-[(1S)-1-(Aminocarbonyl)-2,2-dimethylpropyl]-4-methyl-3-(2-morpholin-4-ylethyl)-2-oxo-2,3-dihydro-1H-benzimidazole-1-carboxamide;
N-[(1S)-1-(Aminocarbonyl)-2,2-dimethylpropyl]-5-methyl-3-(2-morpholin-4-ylethyl)-2-oxo-2,3-dihydro-1H-benzimidazole-1-carboxamide;
N-[(1S)-1-(Aminocarbonyl)-2,2-dimethylpropyl]-3-[2-(dimethylamino)ethyl]-4-methyl-2-oxo-2,3-dihydro-1H-benzimidazole-1-carboxamide;
N-[(1S)-1-Aminocarbonyl)-2-methylpropyl]-3-[2-(dimethylamino)ethyl]-4-methyl-2-oxo-2,3-dihydro-1H-benzimidazole-1-carboxamide;
N-((1S)-1-{[(2-Hydroxyethyl)amino]carbonyl}-2,2-dimethylpropyl)-3-(2-morpholin-4-ylethyl)-2-oxo-2,3-dihydro-1H-benzimidazole-1-carboxamide;
N-[(1S)-1-(Aminocarbonyl)-2-methylpropyl]-3-(2-morpholin-4-ylethyl)-2-oxo-2,3-dihydro-1H-benzimidazole-1-carboxamide;
N-[(1S,2S)-1-(hydroxymethyl)-2-methylbutyl]-3-(2-morpholin-4-ylethyl)-2-oxo-2,3-dihydro-1H-benzimidazole-1-carboxamide;
N-[(1S)-1-(hydroxymethyl)-2,2-dimethylpropyl]-3-(2-morpholin-4-ylethyl)-2-oxo-2,3-dihydro-1H-benzimidazole-1-carboxamide;
N-[(1S)-1-(hydroxymethyl)-3-methylbutyl]-3-(2-morpholin-4-ylethyl)-2-oxo-2,3-dihydro-1 H-benzimidazole-1-carboxamide;
N-{1-[(dimethylamino)carbonyl]-1,3-dimethylbutyl}-3-(2-morpholin-4-ylethyl)-2-oxo-2,3-dihydro-1H-benzimidazole-1-carboxamide;
N-[(1S)-1-(Aminocarbonyl)-2,2-dimethylpropyl]-4-chloro-3-(2-morpholin-4-ylethyl)-2-oxo-2,3-dihydro-1H-benzimidazole-1-carboxamide;
N-[(1S)-1-(Aminocarbonyl)-2,2-dimethylpropyl]-5-chloro-3-(2-morpholin-4-ylethyl)-2-oxo-2,3-dihydro-1H-benzimidazole-1-carboxamide;
N-[(1S)-1-(Aminocarbonyl)-2,2-dimethylpropyl]-3-[(4-hydroxytetrahydro-2H-pyran-4-yl)methyl]-2-oxo-2,3-dihydro-1H-benzimidazole-1-carboxamide;
N-[(1S)-1-(Aminocarbonyl)-2,2-dimethylpropyl]-3-[2-(4-hydroxytetrahydro-2H-pyran-4-yl)ethyl]-2-oxo-2,3-dihydro-1H-benzimidazole-1-carboxamide;
N-[(1S)-1-(Aminocarbonyl)-2,2-dimethylpropyl]-3-[2-(ethylthio)ethyl]-2-oxo-2,3-dihydro-1H-benzimidazole-1-carboxamide;
N-[(1S)-1-(Aminocarbonyl)-2,2-dimethylpropyl]-3-[2-(methylthio)ethyl]-2-oxo-2,3-dihydro-1H-benzimidazole-1-carboxamide;
N-[(1S)-1-(aminocarbonyl)-2,2-dimethylpropyl]-3-[2-(methylsulfinyl)ethyl]-2-oxo-2,3-dihydro-1H-benzimidazole-1-carboxamide;
N-[(1S)-1-(Aminocarbonyl)-2,2-dimethylpropyl]-3-[2-(methylsulfonyl)ethyl]-2-oxo-2,3-dihydro-1H-benzimidazole-1-carboxamide
Methyl N-{[3-(2-Morpholin-4-ylethyl)-2-oxo-2,3-dihydro-1H-benzimidazole-1-yl]carbonyl}-L-phenylalaninate;
N-cyclohexyl-3-(2-morpholin-4-ylethyl)-2-oxo-2,3-dihydro-1H-benzimidazole-1-carboxamide;
N-(2-methylcyclohexyl)-3-(2-morpholin-4-ylethyl)-2-oxo-2,3-dihydro-1H-benzimidazole-1-carboxamide;
N-(2,3-dimethylcyclohexyl)-3-(2-morpholin-4-ylethyl)-2-oxo-2,3-dihydro-1H-benzimidazole-1-carboxamide;
3-(2-morpholin-4-ylethyl)-2-oxo-N-(3,3,5-trimethylcyclohexyl)-2,3-dihydro-1H-benzimidazole-1-carboxamide;
N-(4-methylcyclohexyl)-3-(2-morpholin-4-ylethyl)-2-oxo-2,3-dihydro-1H-benzimidazole-1-carboxamide;
N-(1,3-dimethylbutyl)-3-(2-morpholin-4-ylethyl)-2-oxo-2,3-dihydro-1H-benzimidazole-1-carboxamide;
N-(1-methylpentyl)-3-(2-morpholin-4-ylethyl)-2-oxo-2,3-dihydro-1H-benzimidazole-1-carboxamide;
3-(2-morpholin-4-ylethyl)-2-oxo-N-[(1R)-1,2,2-trimethylpropyl]-2,3-dihydro-1H-benzimidazole-1-carboxamide;
N-cyclooctyl-3-(2-morpholin-4-ylethyl)-2-oxo-2,3-dihydro-1H-benzimidazole-1-carboxamide;
N-(1-methyl-1-phenylethyl)-3-(2-morpholin-4-ylethyl)-2-oxo-2,3-dihydro-1H-benzimidazole-1-carboxamide;
N-[(1R)-1,2-dimethylpropyl]-3-(2-morpholin-4-ylethyl)-2-oxo-2,3-dihydro-1H-benzimidazole-1-carboxamide;
N-[(1S)-1-cyclohexylethyl]-3-(2-morpholin-4-ylethyl)-2-oxo-2,3-dihydro-1H-benzimidazole-1-carboxamide;
3-(2-morpholin-4-ylethyl)-2-oxo-N-(1-propylbutyl)-2,3-dihydro-1H-benzimidazole-1-carboxamide;
N-[(1R)-1-cyclohexylethyl]-3-(2-morpholin-4-ylethyl)-2-oxo-2,3-dihydro-1H-benzimidazole-1-carboxamide;
3-(2-morpholin-4-ylethyl)-2-oxo-N-[(1S)-1,2,2-trimethylpropyl]-2,3-dihydro-1H-benzimidazole-1-carboxamide;
N-[(3S,5S,7S)-1-adamantyl]-3-(2-morpholin-4-ylethyl)-2-oxo-2,3-dihydro-1H-benzimidazole-1-carboxamide;
N-(1-ethynylcyclohexyl)-3-(2-morpholin-4-ylethyl)-2-oxo-2,3-dihydro-1H-benzimidazole-1-carboxamide;
3-(2-morpholin-4-ylethyl)-2-oxo-N-[(1S,2R,3S,5R)-2,6,6-trimethylbicyclo[3.1.1]hept-3-yl]-2,3-dihydro-1H-benzimidazole-1-carboxamide;
N-(dicyclopropylmethyl)-3-(2-morpholin-4-ylethyl)-2-oxo-2,3-dihydro-1H-benzimidazole-1-carboxamide;
methyl N-{[3-(2-morpholin-4-ylethyl)-2-oxo-2,3-dihydro-1H-benzimidazol-1-yl]carbonyl}-L-leucinate;
N-[1-(1-adamantyl)ethyl]-3-(2-morpholin-4-ylethyl)-2-oxo-2,3-dihydro-1H-benzimidazole-1-carboxamide;
N-(1,1-diethylprop-2-yn-1-yl)-3-(2-morpholin-4-ylethyl)-2-oxo-2,3-dihydro-1H-benzimidazole-1-carboxamide;

N-{[(1S,2R,5S)-6,6-dimethylbicyclo[3.1.1]hept-2-yl]methyl}-3-(2-morpholin-4-ylethyl)-2-oxo-2,3-dihydro-1H-benzimidazole-1-carboxamide;

ethyl (1R,2S)-2-({[3-(2-morpholin-4-ylethyl)-2-oxo-2,3-dihydro-1H-benzimidazol-1-yl]carbonyl}amino)cyclohexanecarboxylate;

methyl 1-({[3-(2-morpholin-4-ylethyl)-2-oxo-2,3-dihydro-1H-benzimidazol-1-yl]carbonyl}amino)cyclohexanecarboxylate;

3-(2-morpholin-4-ylethyl)-2-oxo-N-[(1R,2R)-2-(phenylthio)cyclopentyl]-2,3-dihydro-1H-benzimidazole-1-carboxamide;

N-(1-ethyl-1-methylpropyl)-3-(2-morpholin-4-ylethyl)-2-oxo-2,3-dihydro-1H-benzimidazole-1-carboxamide;

N-[(1R,2R,4S)-bicyclo[2.2.1]hept-2-yl]-3-(2-morpholin-4-ylethyl)-2-oxo-2,3-dihydro-1H-benzimidazole-1-carboxamide;

3-(2-morpholin-4-ylethyl)-2-oxo-N-(3,3,5,5-tetramethylcyclohexyl)-2,3-dihydro-1H-benzimidazole-1-carboxamide;

3-(2-morpholin-4-ylethyl)-2-oxo-N-(1,1,3,3-tetramethylbutyl)-2,3-dihydro-1H-benzimidazole-1-carboxamide;

N-(1-isopropyl-2-methylpropyl)-3-(2-morpholin-4-ylethyl)-2-oxo-2,3-dihydro-1H-benzimidazole-1-carboxamide;

N-[(1S,4R)-bicyclo[2.2.1]hept-2-yl]-3-(2-morpholin-4-ylethyl)-2-oxo-2,3-dihydro-1H-benzimidazole-1-carboxamide;

3-(2-morpholin-4-ylethyl)-N-1-naphthyl-2-oxo-2,3-dihydro-1H-benzimidaole-1-carboxamide;

N-(1-adamantylmethyl)-3-(2-morpholin-4-ylethyl)-2-oxo-2,3-dihydro-1H-benzimidazole-1-carboxamide;

Methyl N-{[4-methoxy-3-(2-morpholin-4-ylethyl)-2-oxo-2,3-dihydro-1H-benzimidazol-1-yl]carbonyl}-3-methyl-L-valinate;

N-[(1S)-1-(Aminocarbonyl)-2,2-dimethylpropyl]-4-methoxy-3-(2-morpholin-4-ylethyl)-2-oxo-2,3-dihydro-1H-benzimidazole-1-carboxamide;

N-[(1S)-1-(Aminocarbonyl)-2,2-dimethylpropyl]-2-oxo-3-(2-piperidin-1-ylethyl)-2,3-dihydro-1H-benzimidazole-1-carboxamide;

N-{(1S,2S)-1-[(dimethylamino)carbonyl]-2-methylbutyl}-2-oxo-3-(2-piperidin-1-ylethyl)-2,3-dihydro-1H-benzimidazole-1-carboxamide;

N-{(1S,2S)-1-[(dimethylamino)carbonyl]-2-methylbutyl}-2-oxo-3-(2-thiomorpholin-4-ylethyl)-2,3-dihydro-1H-benzimidazole-1-carboxamide;

4-methoxy-3-(2-morpholin-4-ylethyl)-N-1-naphthyl-2-oxo-2,3-dihydro-1H-benzimidazole-1-carboxamide;

N-1-naphthyl-2-oxo-3-(2-piperidin-1-ylethyl)-2,3-dihydro-1H-benzimidazole-1-carboxamide;

3-[(1-Methylpiperidin-2-yl(methyl)-N-1-naphthyl-2-oxo-2,3-dihydro-1H-benzimidazole-1-carboxamide;

N-[(1S)-1-(aminocarbonyl)-2,2-dimethylpropyl]-3-(2-methyl-2-methylpropyl)-2-oxo-2,3-dihydro-1H-benzimidazole-1-carboxamide;

N-[(1S)-1-(aminocarbonyl)-2,2-dimethylpropyl]-3-(2-hydroxy-2-methylpropyl)-2-oxo-2,3-dihydro-1H-benzimidazole-1-carboxamide;

N-[(1S)-1-cyano-2,2-dimethylpropyl]-3-(2-morpholin-4-ylethyl)-2-oxo-2,3-dihydro-1H-benzimidazole-1-carboxamide;

N-[(1S)-1-(aminocarbonyl)-2,2-dimethylpropyl]-3-(3-hydroxy-3-methylbutyl)-2-oxo-2,3-dihydro-1H-benzimidazole-1-carboxamide;

N-{(1S)-1-[(dimethylamino)carbonyl]-2,2-dimethylpropyl}-4-methyl-3-[2-(methylthio)ethyl]-2-oxo-2,3-dihydro-1H-benzimidazole-1-carboxamide;

N-{(1S)-1-[(dimethylamino)carbonyl]-2,2-dimethylpropyl}-4-methyl-3-[2-(methylsulfonyl)ethyl]-2-oxo-2,3-dihydro-1H-benzimidazole-1-carboxamide;

N-[(1S)-2,2-dimethylpropyl]-3[2-(methylsulfonyl)ethyl]-2-oxo-2,3-dihydro-1H-benzimidazole-1-carboxamide;

N-[(1S)-(1-aminocarbonyl)-2,2-dimethylpropyl]-3-(3-amino-3-methylbutyl)-2-oxo-2,3-dihydro-1H-benzimidazole-1-carboxamide;

Rel-3-[2-(dimethylamino)ethyl]-N-[(1R,2S)-2-hydroxycyclohexyl]-4-methyl-2-oxo-2,3-dihydro-1H-benzimidazole-1-carboxamide;

N-[(1S)-1-(aminocarbonyl)-2,2-dimethylpropyl]-3-{2-[methyl(methylsulfonyl)amino]ethyl}-2-oxo-2,3-dihydro-1H-benzimidazole-1-carboxamide;

N-[(1S)-1-(aminocarbonyl)-2,2-dimethylpropyl]-2-oxo-3-(1,1,3,3-tetramethylbutyl)-2,3-dihydro-1H-benzimidazole-1-carboxamide;

N-[(1S)-1-(aminocarbonyl)-2,2-dimethylpropyl]-6-methyl-3-[2-(4-morpholinyl)ethyl]-2-oxo-2,3-dihydro-1H-benzimidazole-1-carboxamide;

N-[(1S)-1-(aminocarbonyl)-2,2-dimethylpropyl]-3[2-(dimethylamino)ethyl]-2-oxo-4-(trifluoromethyl)-2,3-dihydro-1H-benzimidazole-1-carboxamide;

N-[(1S)-1-(aminocarbonyl)-2,2-dimethylpropyl]-5-fluoro-3[2-(4-morpholinyl)ethyl]-2-oxo-2,3-dihydro-1H-benzimidazole-1-carboxamide;

N-[(1S)-1-(aminocarbonyl)-2,2-dimethylpropyl]-3-(3-hydroxy-3-methylbutyl)-4-methyl-2-oxo-2,3-dihydro-1H-benzimidazole-1-carboxamide;

N-[(1S)-1-(aminocarbonyl)-2,2-dimethylpropyl]-3-(1-hydroxycyclobutyl)methyl]-2-oxo-2,3-dihydro-1H-benzimidazole-1-carboxamide;

N-((1S)-2,2-dimethyl-1-{[(methylsulfonyl)amino]methyl}propyl)-3-[2-(4-morpholinyl)ethyl]-2-oxo-2,3-dihydro-1H-benzimidazolone-1-carboxamide;

N-[(1S)-1-(aminocarbonyl)-2,2-dimethylpropyl]-3-[2-(dimethylamino)ethyl]-4-fluoro-2-oxo-2,3-dihydro-1H-benzimidazole-1-carboxamide;

3-(3-hydroxy-3-methylbutyl)-N-[(1S)-1-(hydroxymethyl)-2,2-dimethylpropyl]-2-oxo-2,3-dihydro-1H-benzimidazole-1-carboxamide;

N-{(1S)-2,2-dimethyl-1-[(methylsulfonyl)methyl]propyl}-3-(3-hydroxy-3-methylbutyl)-2-oxo-2,3-dihydro-1H-benzimidazole-1-carboxamide;

3-(3-hydroxy-3-methylbutyl)-N-[1-(hydroxymethyl)cyclopentyl-2-oxo-2,3-dihydro-1H-benzimidazole-1-carboxamide;

N-[1-(aminocarbonyl)-2,2-dimethylpropyl]-3-[(1-hydroxycyclohexyl)methyl]-2-oxo-2,3-dihydro-1H-benzimidazole-1-carboxamide;

N-[1-(aminocarbonyl)-2,2-dimethylpropyl]-2-oxo-3-(tetrahydrofuran-2-ylmethyl)-2,3-dihydro-1H-benzimidazole-1-carboxamide;

N-(1-acetyl-2,2-dimethylpropyl)-3-(2-morpholin-4-ylethyl)-2-oxo-2,3-dihydro-1H-benzimidazole-1-carboxamide;

N-[(1S)-1-(aminocarbonyl)-2,2-dimethylpropyl]-4-methyl-2-oxo-3-(2-pyrrolidin-1-ylethyl)-2,3-dihydro-1H-benzimidazole-1-carboxamide;

N-[(1S)-1-(aminocarbonyl)-2,2-dimethylpropyl]-3-(2-hydroxy-2-methylpropyl)-4-methyl-2-oxo-2,3-dihydro-1H-benzimidazole-1-carboxamide;

N-[(1S)-1-(aminocarbonyl)-2,2-dimethylpropyl]-3-[(1-hydroxycyclopentyl)methyl]-2-oxo-2,3-dihydro-1H-benzimidazole-1-carboxamide;

N-[(1S)-1-(aminocarbonyl)-2,2-dimethylpropyl]-3[2-(4-hydroxytetrahyro-2H-pyran-4-yl)ethyl]-4-methyl-2-oxo-2,3-dihydro-1H-benzimidazole-1-carboxamide;

N-[(1S)-1-(aminocarbonyl)-2,2-dimethylpropyl]-2-oxo-3-(tetrahydro-2H-pyran-4-ylmethyl)-2,3-dihydro-1H-benzimidazole-1-carboxamide;

N-[(1S)-1-tert-butyl-3,3,3-trifluoro-2-hydroxypropyl]-3-(2-morpholin-4-ylethyl)-2-oxo-2,3-dihydro-1H-benzimidazole-1-carboxamide hydrochloride;

N-[(1S)-1-tert-butyl-3,3,3-trifluoro-2-oxopropyl]-3-(2-morpholin-4-ylethyl)-2-oxo-2,3-dihydro-1H-benzimidazole-1-carboxamide;

N-[(1R)-1-(cyanomethyl)-2,2-dimethylpropyl]-3-(3-hydroxy-3-methylbutyl)-2-oxo-2,3-dihydro-1H-benzimidazole-1-carboxamide;

N-[(1R)-1-(2-amino-2-oxoethyl)-2,2-dimethylpropyl]-3-(3-hydroxy-3-methylbutyl)-2-oxo-2,3-dihydro-1H-benzimidazole-1-carboxamide;

N-[(1R)-1-(2-hydroxyethyl)-2,2-dimethylpropyl]-3-(3-hydroxy-3-methyl butyl)-2-oxo-2,3-dihydro-1H-benzimidazole-1-carboxamide;

N-[(1S)-1-tert-butyl-2-hydroxy-2-methylpropyl]-3-(3-hydroxy-3-methylbutyl)-2-oxo-2,3-dihydro-1H-benzimidazole-1-carboxamide;

N-[(1S)-1-(aminocarbonyl)-2,2-dimethylpropyl]-3-(2-dimethylamino)-2-methylpropyl]-2-oxo-2,3-dihydro-1H-benzimidazole-1-carboxamide;

N-[(1S)-1-tert-butyl-3,3,3-trifluoro-2-oxopropyl]-3-(3-hydroxy-3-methyl butyl)-2-oxo-2,3-dihydro-1H-benzimidazole-1-carboxamide;

N-[(1S)-1-tert-butyl-3,3,3-trifluoro-2-oxopropyl]-3[2-(methylsulfonyl)ethyl]-2-oxo-2,3-dihydro-1H-benzimidazole-1-carboxamide;

N-[(1S)-1-(aminocarbonyl)-2,2-dimethylpropyl]3-[(4-hydroxytetrahydro-2H-pyran-4-yl)methyl]-4-methyl-2-oxo-2,3-dihydro-1H-benzimidazole-1-carboxamide;

N-[(1S)-1-(aminocarbonyl)-2,2-dimethylpropyl]-4-methyl-3-[2-(methylthio)ethyl]-2-oxo-2,3-dihydro-1H-benzimidazole-1-carboxamide;

N-{(1S)-2,2-dimethyl-1-[(methylamino)carbonyl]propyl}-4-methyl-3-[2-(methylthio)ethyl]-2-oxo-2,3-dihydro-1H-benzimidazole-1-carboxamide;

N-[(1S)-1-(hydroxymethyl)-2,2-dimethylpropyl]-4-methyl-3-[2-(methylthio)ethyl-2-oxo-2,3-dihydro-1H-benzimidazole-1-carboxamide;

N-{(1S)-1-(aminocarbonyl)-2,2-dimethylpropyl}-4-methyl-3-[2-(methylsulfonyl)ethyl]-2-oxo-2,3-dihydro-1H-benzimidazole-1-carboxamide;

N-{(1S)-2,2-dimethyl-1-[(methylamino)carbonyl]propyl}-4-methyl-3-[2-(methylsulfonyl)ethyl]-2-oxo-2,3-dihydro-1H-benzimidazole-1-carboxamide;

N-[(1S)-1-(hydroxymethyl)-2,2-dimethylpropyl]-4-methyl-3-[2-(methylsulfonyl)ethyl-2-oxo-2,3-dihydro-1H-benzimidazole-1-carboxamide;

rel-N-[(1R,2S)-2-hydroxycyclohexyl]-4-methyl-3-[2-(methylsulfonyl)ethyl]-2-oxo-2,3-dihydro-1H-benzimidazole-1-carboxamide;

or a pharmaceutically acceptable salt thereof.

\* \* \* \* \*